(12) United States Patent
Saxon

(10) Patent No.: US 7,879,324 B2
(45) Date of Patent: Feb. 1, 2011

(54) FUSION MOLECULES AND METHODS FOR TREATMENT OF IMMUNE DISEASES

(75) Inventor: Andrew Saxon, Santa Monica, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 12/404,012

(22) Filed: Mar. 13, 2009

(65) Prior Publication Data

US 2009/0317389 A1    Dec. 24, 2009

Related U.S. Application Data

(60) Division of application No. 10/000,439, filed on Oct. 24, 2001, now Pat. No. 7,534,440, which is a continuation-in-part of application No. 09/847,208, filed on May 1, 2001, now Pat. No. 7,265,208.

(51) Int. Cl.
*A61K 39/00* (2006.01)
*C07K 16/46* (2006.01)

(52) U.S. Cl. ............... 424/134.1; 424/143.1; 424/185.1; 424/192.1; 424/275.1

(58) Field of Classification Search ................... None
See application file for complete search history.

(56) References Cited

U.S. PATENT DOCUMENTS

| | | | |
|---|---|---|---|
| 4,902,495 A | 2/1990 | Kaliner et al. | |
| 5,017,693 A | 5/1991 | Hylarides et al. | 530/390 |
| 5,116,964 A | 5/1992 | Capon et al. | |
| 5,141,648 A | 8/1992 | Hylarides et al. | 210/635 |
| 5,329,028 A | 7/1994 | Ashkenazi et al. | 548/548 |
| 5,336,603 A | 8/1994 | Capon et al. | |
| 5,358,710 A | 10/1994 | Sehon et al. | 424/178.1 |
| 5,420,247 A | 5/1995 | Gearing et al. | 530/350 |
| 5,512,283 A | 4/1996 | Byers et al. | 424/171.1 |
| 5,558,869 A | 9/1996 | Burks, Jr. et al. | 424/276.1 |
| 5,560,915 A | 10/1996 | Patterson et al. | 424/275.1 |
| 5,563,250 A | 10/1996 | Hylarides et al. | 536/4.1 |
| 5,565,335 A | 10/1996 | Capon et al. | 435/69.7 |
| 5,637,454 A | 6/1997 | Harley | 435/5 |
| 5,645,820 A | 7/1997 | Hafler et al. | 424/41 |
| 5,672,683 A | 9/1997 | Friden et al. | 530/350 |
| 5,736,507 A | 4/1998 | Boots et al. | 514/2 |
| 5,811,265 A | 9/1998 | Quertermous et al. | 435/69.3 |
| 5,827,516 A | 10/1998 | Urban et al. | 424/93.2 |
| 5,843,449 A | 12/1998 | Boots et al. | 424/185.1 |
| 5,858,980 A | 1/1999 | Weiner et al. | |
| 5,869,093 A | 2/1999 | Weiner et al. | 424/451 |
| 5,880,103 A | 3/1999 | Urban et al. | 514/44 |
| 5,925,351 A | 7/1999 | Browning et al. | |
| 5,945,294 A | 8/1999 | Frank et al. | |
| 5,965,605 A | 10/1999 | Cheng et al. | 514/454 |
| 5,973,121 A | 10/1999 | Burks, Jr. et al. | |
| 5,977,307 A | 11/1999 | Friden et al. | 530/350 |
| 6,043,345 A | 3/2000 | Saxon et al. | 530/387.1 |
| 6,093,699 A | 7/2000 | Sehon et al. | 514/44 |
| 6,103,697 A | 8/2000 | Bergstrand et al. | 514/14 |
| 6,214,974 B1 | 4/2001 | Rosenblum et al. | 530/391.9 |
| 6,228,373 B1 | 5/2001 | Bergstrand et al. | 424/278.1 |
| 6,228,374 B1 | 5/2001 | Bergstrand et al. | 424/278.1 |
| 6,287,792 B1 | 9/2001 | Pardridge et al. | 435/7.5 |
| 6,372,250 B1 | 4/2002 | Pardridge et al. | 424/450 |
| 7,265,208 B2 * | 9/2007 | Saxon et al. | 530/387.1 |
| 7,488,804 B2 * | 2/2009 | Saxon et al. | 530/387.3 |
| 7,534,440 B2 * | 5/2009 | Saxon | 424/192.1 |
| 2001/0053770 A1 | 12/2001 | Thomas et al. | 514/44 |
| 2003/0049237 A1 | 3/2003 | Bannon et al. | 424/93.21 |
| 2003/0077282 A1 | 4/2003 | Bigler et al. | 424/144.1 |
| 2004/0198961 A1 | 10/2004 | An et al. | 530/391.1 |
| 2005/0250934 A1 | 11/2005 | Wang et al. | 530/387.1 |
| 2006/0171942 A1 * | 8/2006 | Saxon et al. | 424/133.1 |
| 2009/0136493 A1 * | 5/2009 | Saxon et al. | 424/133.1 |

FOREIGN PATENT DOCUMENTS

WO    WO 88/09344    * 12/1988

(Continued)

OTHER PUBLICATIONS

Ngo et al, The Protein Folding Problem and Tertiary Structure Prediction, pp. 491-495, 1994.*

(Continued)

*Primary Examiner*—Phuong Huynh
(74) *Attorney, Agent, or Firm*—James A. Fox; Ginger R. Dreger; Arnold & Porter LLP

(57) ABSTRACT

The invention concerns bifunctional fusion molecules, and novel, safer and more efficacious methods for the treatment of immune disorders resulting from excessive or unwanted immune responses. The invention provides methods for the suppression of type I hypersensitive (i.e., IgE-mediated) allergic conditions, methods for the prevention of anaphylactic responses that occur as a result of traditional peptide immunotherapies for allergic and autoimmune disorders, and provides novel methods for the treatment of autoimmune conditions, where the methods have reduced risk of triggering an anaphylactic response. The invention provides novel therapeutic approaches for the treatment of allergic responses, including the prevention of anaphylactic response that can occur from environmental allergen exposure. The invention also provides methods for the treatment of autoimmune disorders such as multiple sclerosis, autoimmune type I diabetes mellitus, and rheumatoid arthritis. The invention also provides methods for preventing anaphylactic response during traditional antigen therapies.

12 Claims, 11 Drawing Sheets

FOREIGN PATENT DOCUMENTS

| | | | |
|---|---|---|---|
| WO | WO 95/14779 | | 6/1995 |
| WO | WO 95/26365 | | 10/1995 |
| WO | WO 96/12740 | | 5/1996 |
| WO | WO 96/16086 | | 5/1996 |
| WO | WO 96/22024 | | 7/1996 |
| WO | WO 96/26961 | * | 9/1996 |
| WO | WO 96/40789 | | 12/1996 |
| WO | WO 99/02709 | | 1/1999 |
| WO | WO 99/02710 | | 1/1999 |
| WO | WO 99/02711 | | 1/1999 |
| WO | WO 99/57241 | | 11/1999 |
| WO | WO 99/67293 | | 12/1999 |
| WO | WO 00/01732 | | 1/2000 |
| WO | WO 00/05254 | | 3/2000 |
| WO | WO 02/102320 A2 | | 12/2002 |
| WO | WO 02/102320 A3 | | 12/2002 |

OTHER PUBLICATIONS

Stryer et al, In Biochemistry, Third edition, W H Freeman Company, New York, pp. 31-33, 1998.*

Hellman et al, Adv Exp Med Biol 409: 337-342, Sep. 1996.*

Terada et al, Clinical Immunology 120(1): 45-56, 2006.*

Tangley et al, A therapy for cat allergies, Thanks to mice, the New York time, pp. 1-2, Apr. 5, 2005.*

Saxon et al, J Allergy Clin Immunol 121: 320-325, 2008.*

Zhang et al, Immunol Allergy Clin North Am 27(1): 93-103, Feb. 2007.*

Zhu et al, Nat Med 11(4): 446-449, Epub Mar. 27, 2005.*

American Autoimmune Related Diseases Association, Questions and Answers, pp. 1-4, Jul. 26, 2001 (http://www.aarda.org/questions_and_answers.html).

Alvarez-Fernandez, Marcia, et al., "Inhibition of Mammalian Legumain by Some Cystatins Is Due to a Novel Second Reactive Site", The Journal of Biological Chemistry, vol. 274, No. 27, Issue of Jul. 2, pp. 19195-19203, 1999.

Resources for Health Professionals: Anaphylaxis, pp. 1-10, Sep. 18, 2001 (http://www.worldallergy.org/professional/allergy_update/anap.../anaphylaxissynopsis.shtm).

Ansari, AA, et al., "Epitope Mapping of the Branched Chain Alpha-Ketoacid Dehydrogenase Dihydrolipoyl Transacylase (BCKD-E2) Protein that Reacts with Sera from Patients with Idiopathic Dilated Cardiomyopathy", (abstract), J Immunol, 153(10):4754-65 Nov. 15, 1994.

AroTec Diagnostics Limited—β2-Glycoprotein 1 (human), pp. 1-3, Jul. 12, 2001 (http://webnz.com/arotec/masa5002.htm).

AroTec Diagnostics Limited—Myeloperoxidase (pANCA) Antigen, pp. 1-3, Jul. 12, 2001 (http://webnz.com/arotec/masa5009.htm).

AroTec Diagnostics Limited—Proteinase 3 (cANCA) Antigen, pp. 1-3, Jul. 12, 2001 (http://webnz.com/arotec/masa5008.htm).

AroTec Diagnostics Limited—La (SSB) Antigen, pp. 1-3, Jul. 12, 2001 (http://webnz.com/arotec/masa5010.htm).

AroTec Diagnostics Limited—Ro (SSA) Antigen, pp. 1-3, Jul. 11, 2001 (http://webnz.com/arotec/masa5011.htm).

AroTec Diagnostics Limited—Sm Antigen, pp. 1-3, Jul. 12, 2001 (http://webnz.com/arotec/masa5007.htm).

AroTec Diagnostics Limited—RNP/Sm Antigen, pp. 1-3, Jul. 12, 2001 (http://webnz.com/arotec/masa5006.htm).

AroTec Diagnostics Limited—Scl-70 Antigen, pp. 1-3, Jul. 12, 2001 (http://webnz.com/arotec/masa5001.htm).

AroTec Diagnostics Limited—Parietal Cell Antigen (H/K-ATPase), pp. 1-3, Jul. 12, 2001 (http://webnz.com/arotec/masa5004.htm).

AroTec Diagnostics Limited—Jo-1 Antigen, pp. 1-2, Jul. 11, 2001 (http://webnz.com/arotec/masa5005.htm).

"Autoantigen Sequences", pp. 1-3, Jul. 11, 2001 (http://129.206.51.31/mb/ana_base.html).

"Autoimmune Disease: Rapid Progress in our Understanding of Immune Function Promises More Effective Treatments for Autoimmune Disorders", Nature Biotechnology, vol. 18, pp. 1T7-1T9, Supplement 2000.

Barker RN, et al., "Red Blood Cell Glycophorins as B and T-cell Antigents in Canine Autoimmune Haemolytic Anaemia", (abstract) Vet Immunol Immunopathol, 47(3-4):225-38, Aug. 1995.

"Alphaβ-Crystallin in Multiple Sclerosis", J. Immunol, vol. 129-135, pp. 1-5, Jul. 20, 2001 (http://www.albany.net/~tjc/crystalline.html).

Bajramovic, JJ, et al., "Presentation of αB-Crystallin to T Cells in Active Multiple Sclerosis Lesions: An Early Event Following Inflammatory Demyelination", The American Association of Immunologists, vol. 164, pp. 4359-4366, 2000.

Bigazzi, PE, MD, Lecture on "Autoimmune Disease", The University of Connecticut, pp. 1-6, Jul. 30, 2001, (http://155.37.1.60/Lectures/PB/Autoimmune.html).

Bonfa, E., et al., "Frequency and Epitope Recognition of Anti-Ribosome P Antibodies from Humans with Systemic Lupus Erythematosus and MRL/lpr Mice are Similar", (abstract), J Immunol; 140(1):3434-3437, May 15, 1998.

Bridges, SL, Jr., et al., "T-Cell Receptor Peptide Vaccination in the Treatment of Rheumatoid Arthritis", Emerging Therapies for Rheumatoid Arthritis, vol. 24, pp. 641-650, 1998.

Cambier, JC, "Commentary: Inhibitory receptors abound?", Proc. Natl. Acad. Sci. USA, vol. 94, pp. 5993-5995, 1997.

Chapman, Martin D., et al., "Recombinant Allergens for Diagnosis and Therapy of Allergic Disease", J Allergy Clin Immunol, pp. 409-418, 2000.

Critchfield, JM, et al., "T Cell Deletion in High Antigen Dose Therapy of Autoimmune Encephalomyelitis", Science Feb. 25; 263(5150):1139-43, 1994 (abstract).

De Palma, R, et al., "Use of Altered Peptide Ligands to Modulate Immune Responses As a Possible Immunotheraphy for Allergies", Allergy: 55: Suppl 61: 56-59, 2000.

Decker, Patrice, et al., "Inhibition of Caspase-3-Mediated Poly (ADP-Ribose) Polymerase (PARP) Apoptotic Cleavage by Human PARP Autoantibodies and Effect on Cells Undergoing Apoptosis", The Journal of Biological Chemistry, © 2000 by The American Society for Biochemistry and Molecular Biology, Inc., vol. 275, No. 12, pp. 9043-9046, Mar. 24, 2000.

Delespesse, G. et al., "The Low-Affinity Receptor for IgE," *Immunological Reviews*, No. 125, pp. 77-97 (1992).

Merck Corp., "Disorders With Type III Hypersensitivity Reactions", The Merck Manual, Sec. 12, Ch. 148, Hypersensitivity Disorders, Jul. 12, 2001.

Ditzel, Henrik J., "Human Antibodies in Cancer and Autoimmune Disease", Immunologic Research; 21(2-3):185-193, 2000.

Earnshaw WC, et al., "Identification of a Family of Human Centromere Proteins Using Autoimmune Sera From Patients With Scleroderma", (abstract) Chromosoma, 91(3-4):313-321, 1985.

Elkon, KB, et al., "Lupus Autoantibodies Target Ribosomal P Proteins", (abstract) J Exp Med, 162(2): 459-471, Aug. 1 1985.

Fabien N., et al., "Autoantibodies Directed Against the Ribosomal P Proteins Are Not Only Directed Against a Common Epitope of the P0, P1 and P2 Proteins", (abstract) J Autoimmune, 13(1): 103-110, Aug. 1999.

Faria AM, et al., "Oral Tolerance: Mechanisms and Therapeutic Applications", (abstract), Adv Immunol, 73:153-264, 1999.

Frampton, G., et al., "Identification of Candidate Endothelial Cell Autoantigens in Systemic Lupus Erythematosus Using a Molecular Cloning Strategy: A Role for Ribosomal P Protein P0 As an Endothelial Cell Autoantigen", Rheumatology (Oxford), (abstract) 39(10):1114-1120, Oct. 2000.

Giovannoni, G, et al., "Multiple Sclerosis and Its Treatment", (abstract) J R Coll Physicians Lond, 33(4):315-22, Jul.-Aug. 1999.

Gold, Daniel P., et al., "T-Cell Receptor Peptides As Immunotherapy for Autoimmune Disease", Critical Reviews™ in Immunology, (abstract) 17:507-510, 1997.

Gold, DP, "Results of a Phase I Clinical Trial of a T-Cell Receptor Vaccine in Patients With Multiple Sclerosis. II. Comparative Analysis of TCR Utilization in CSF T-Cell Populations Before and After Vaccination With a TCRV Beta 6 CDR2 Peptide", (abstract) J Neuroimmunol, 76(1-2):29-38, Jul. 1997.

Gold, HA, et al., "The RNA Processing Enzyme RNase MRP Is Identical to the Th RNP and Related to RNase P", (abstract) Science, 245(4924):1377-80, Sep. 22, 1989.

Gottlieb, A.B., et al., Anti-CD4 Monoclonal Antibody Treatment of Moderate to Severe Psoriasis Vulgaris: Results of a Pilot, Multicenter, Multiple-Dose, Placebo-Controlled Study, (abstract) J Am Acad Dermatol, 43(4):595-604, Oct. 2000.

Gunnarsson, Andreas, et al., "Molecular Properties of the Goodpasture Epitope", The Journal of Biological Chemistry, vol. 275, No. 40, pp. 30844-30848, Oct. 6, 2000.

Haselden, B.M., et al., "Peptide-Mediated Immune Responses in Specific Immunotherapy", Int Arch Allergy Immunol, 122(4):229-37, 2000.

Hellmark, T., et al., "Characterization of Anti-GBM Antibodies Involved in Goodpasture's Syndrome", (abstract) Kidney Int, 46(3):823-9, Sep. 1994.

Hirano, T., et al., "Human Tissue Distribution of TA02, which is Homologous with a New Type of Aspartic Proteinase, Napsin A", (abstract) Jpn J Cancer Res, 91(10):1015-21, Oct. 2000.

"Histones and Subclasses", Jul. 30, 2001, PurifiedAntigens for Autoimmune Testing, (http://www.immunovision.com/pg0019.htm).

Hughes, G.R., The Antiphospholipid Syndrome: Ten Years On, (abstract) Lancet, 342(8867):341-344, Aug. 7, 1993.

Karlsson, F.A., et al., "Major Parietal Cell Antigen in Autoimmune Gastritis with Pernicious Anemia is the acid-producing H+, K+adenosine Triphosphatase of the Stomach", (Abstract) J Clin Invest, 81(2):475-9, Feb. 1988.

Kozlowski, Maya, et al., "SHP-1 Binds and Negatively Modulates the c-Kit Receptor by Interaction with Tyrosine 569 in the c-Kit Juxtamembrane Domain", Molecular and Cellular Biology, pp. 2089-2099, vol. 18, No. 4, Apr. 1998.

Kronus, "Addison's Disease", Enzyme Steroid 21-Hydroxylase (21-OH) Antibody, (http:www.kronus.com/products/addisons.html), Jul. 30, 2001.

Kronus, "Celiac Disease", Tissue Transglutaminase (tTg) Autoantibody, (http:www.kronus.com/products/celiac.html), Jul. 30, 2001.

Kronus, "Diabetes", (http:www.kronus.com/products/diabetes.html), Jul. 30, 2001.

Kronus, "Neuromuscular", Myasthenia Gravis, (http:www.kronus.com/products/neuromuscular.html), Jul. 30, 2001.

Kronus, "Thyroid Autoimmune", (http:www.kronus.com/products/thyroid-auto.html), Jul. 30, 2001.

Krogsgaard, M., et al., "Visualization of Myelin Basic Protein (MBP) T Cell Epitopes in Multiple Sclerosis Lesions Using a Monoclonal Antibody Specific for the Human Histocompatibility Leukocyte Antigen (HLA)-DR2-MBP 85-99 complex", (abstract), J Exp Med, Apr. 17;191(8):1395-412, 2000.

Larche, Mark, "Specific Immunotherapy", British Medical Bulletin, 56 (No. 4): 1019-1036, 2000.

Malbec, Odile, et al., "The SH2 Domain-containing Inositol 5-Phosphatase SHIP1 Mediates Cell Cycle Arrest by FcγRIIB", JBC Papers in Press., pp. 1-29, May 18, 2001.

McNeil, H. Patrick, et al., "Anti-Phospholipid Antibodies are Directed Against a Complex Antigen that Includes a Lipid-Binding Inhibitor of Coagulation: $\beta_2$-Glycoprotein I (apolipoprotein H)", Proc. Natl. Acad. Sci. USA, vol. 87, pp. 4120-4124, Medical Sciences, Jun. 1990.

Mimori, T., et al., "Characterization of the DNA-binding protein antigen Ku recognized by autoantibodies from Patients with Rheumatic Disorders", (abstract) J. Biol. Chem., 261(5):2274-8, Feb. 15, 1986.

Misaki, Y., et al., "The 56K Autoantigen is Identical to Human Annexin XI", (Abstract) J. Biol. Chem., 269(6):4240-6, Feb. 11, 1994.

Immunovision (Brochure), "Mitochondrial Antigen", Purified Antigens for Autoimmune Testing, (http://www.immunovision.com/pg0020.htm), Jul. 30, 2001.

Mu, F.T., et al., "EEA1, an Early Endosome-Associated Protein. EEA1 is a Conserved Alpha-Helical Peripheral Membrane Protein Flanked by Cysteine "Fingers" and Contains a Calmodulin-Binding IQ Motif", J. Biol. Chem., 270(22):13503-11, Jun. 2, 1995.

Nakajima, Atsuo, et al., "Antigen-Specific T Cell-Mediated Gene Therapy in Collagen-Induced Arthritis", The Journal of Clinical Investigation, vol. 107, No. 10, pp. 1293-1301 May 2001.

Newkirk, Marianna M., et al., "Autoimmune Response to U1 Small Nuclear Ribonucleoprotein (U1 snRNP) Associated with Cytomegalovirus Infection", Arthritis Res, 3: 253-258, Jul. 30, 2001.

Norman, Philip S., "Therapeutic Potential of Peptides in Allergic Disease", Annals of Allergy, vol. 71, pp. 330-333, Sep. 1993.

Okano, Y., et al., "Autoantibody to Th Ribonucleoprotein (Nucleolar 7-2 RNA Protein Particle) in Patients with Systemic Sclerosis", Arthritis Rheum, 33(12):1822-8, Dec. 1990, (abstract).

Ono, S.J., "Molecular Genetics of Allergic Diseases", Annu Rev Immunol, 18:347-66, 2000, (abstract).

Rock, Kenneth L., et al., "Degradation of Cell Proteins and the Generation of MHC Class I-Presented Peptides", Annu. Rev. Immunol., 17:739-79, 1999, (abstract).

Cascio P, et al., "26Sproteasomes and Immunoproteaseomes Produce Mainly N-Extended Cersions of an Antigenic Peptide", EMBO J, 20(10):2357-2366, May 15, 2001, (abstract).

Yewdell, JW., et al., "Not Such a Dismal Science: The Economics of Protein Sythesis, Folding, Degradation and Antigen Processing", Trends Cell Biol, 11(7):294-297, Jul. 2001, (abstract).

Fiebiger E., et al., "Cytokines Regulate Proteolysis in Major Histocompatibility complex Class II-Dependent Antigen Presentationby Dendritic Cells" J. Exp. Med., 193(8):881-892, Apr. 16, 2001, (abstract).

Stoltze L, et al., "Two New Proteases in the MHC Class I Processing Pathway", Nat. Immunol., 1(5):413-418, Nov. 2000, (abstract).

Suter, U., et al., "Expression of Human Lymphocyte IgE Receptor (FCTRIIICD23)", The Journal of Immunology, vol. 143, No. 9, pp. 3087-3092, Nov. 1, 1989.

Muno D., et al., "Generation of both MHC Class I- and Class II-Restricted Antigenic Peptides from Exogenously Added Ovalbumin in Murin Phagosomes", FEBS Lett, 478(1-2)178-182, Jul. 28, 2000, (abstract).

Manoury B., et al., "An Asparaginyl Endopeptidase Processes a Microbial Antigen for Class II MHC Presentation", Nature, 396(6712):625-627, Dec. 17, 1998, (abstract).

Auto Immune, Inc., "Overview of Oral tolerance Therapy" Research and Development—OT Technology, Jul. 30, 2001, (http://www.autoimmuneinc.com/R_D/tech.html).

Immunovision (Brochure), "PCNA Antigen", Purified Antigens for Autoimmune Testing, Jul. 30, 2001, (http://www.immunovision.com/pg0061.htm).

Pisetsky, D.S., "The Role of Bacterial DNA in Autoantibody Induction", (abstract) Curr Top Microbiol Immunol, 247:143-155, 2000.

Rickert, M., et al., "Fusion Proteins for Combined Analysis of Autoantibodies to the 65-kda Isoform of Glutamic Acid Decarboxylase and Islet Antigen-2 in Insulin-Dependent Diabetes Mellitus", Clin Chem, 47(5):926-34, May 2001, (abstract).

Immunovision (Brochure), "Ribosomal P Antigen", Purified Antigens for Autoimmune Testing, Jul. 30, 2001, (http://vvww.immunovision.com/pg0021.htm).

Rider, Lisa G., et al., "Laboratory Evaluation of the Inflammatory Myopathies", Clinical and Diagnostic Laboratory Immunology, vol. 2, No. 1, p. 1-9, Jan. 1995.

Riese, Richard J., et al., "Cathepsin S Activity Regulates Antigen Presentation and Immunity", J. Clin. Invest., vol. 101, No. 11, 2351-2363, Jun. 1998.

Immunovision (Brochure), "Ro/SS-A Antigen", Jul. 30, 2001, (http://www.immunovision.com/pg0013.htm).

Noel Rose, et al., The Autoimmune Diseases: Table of Contents, Third Edition, Academic Press 1998.

Saric, Tomo, et al., "MHC Class I-Presented Antigenic Peptides are Degraded in Cytosolic Extracts Primarily by Thimet Oligopeptidase", JBC Papers in Press., Published Jul. 30, 2001.

Immunovision (Brochure), "Scl-70 Antigen", Purified Antigens for Autoimmune Testing (http://www.immunovision.com/pg0017.htm), Jul. 30, 2001.

Immunovision (Brochure), "SMITH (sm) Antigen", Purified Antigens for Autoimmune Testing (http://www.immunovision.com/pg0015.htm), Jul. 30, 2001.

Sela, M., "Specific Vaccines Against Autoimmune Diseases", C R Acad Sci III; 322(11):933-8, Nov. 1999, (abstract).

Schuppan, D, et al., "Identification of the Autoantigen of Celiac Disease", Ann N Y Acad Sci., 859:121-6, Nov. 17, 1998, (abstract).

Steinman, L., "Multiple Sclerosis: a Coordinated Immunological Attack Against Myelin in the Central Nervous System", Cell, 85(3):299-302, May 3, 1996, (abstract).

Abdelilah, S. G. et al., Molecular characterization of the low-affinity IgE receptor FcεRII/CD23 expressed by human eosinophilis, International Immunology, vol. 10, No. 4, pp. 395-404, Apr. 1998.

Abramson, M. J., et al., "Allergen immunotherapy for asthma", The Cochrane Library, Issue 1, pp. 1-32, 1999.

Adamczewski, M., and Kinet, J-P., "The High-Affinity Receptor for Immunoglobulin E," Chemical Immun , 59:173-190 (1994).

Akdis, C. A., et al., "Epitope-specific T Cell Tolerance to Phospholipase $A_2$ in Bee Venom Immunotherapy and Recovery by IL-2 and IL-15 In Vitro", Journal of Clinical Investigation, vol. 98, No. 7, pp. 1676-1683, Oct. 1996.

Antoniou, A. N., et al., "Control of Antigen Presentation by a Single Protease Cleavage Site", Immunity, vol. 12, pp. 391-398, Apr. 2000.

Arm, J. P. et al., Molecular Cloning of gp49, a Cell-surface Antigen That Is Preferentially Expressed by Mouse Mast Cell Progenitors and Is a New Member of the Immunoglobulin Superfamily J. Biol. Chem. 266:15966-15973 (1991).

Arm, J.P., et al., "Molecular Identification of a Novel Family of Human Ig Superfamily Members That Possess Immunoreceptor Tyrosine-Based Inhibition Motifs and Homology to the Mouse gp49B1 Inhibitory Receptor1, 2", J. Immunol., vol. 159, pp. 2342-2349, 1997.

Ashman, Robert F., et al., "Fc Receptor Off Signal in the B Cell Involves Apoptosis", The Journal of Immunology, vol. 157, pp. 5-11, 1996.

Atwood, T. K., et al., "The Babel of Bioinformatics" Science, vol. 290, No. 5491, pp. 471-473, Oct. 2000.

Barnes, P. J., "Anti-IgE Antibody Therapy for Asthma," The New England Journal of Medicine 341(26):2006-2008 (1999).

Barsoum et al, Med Microbiol Immunol 163: 227-232, 1977.

Basu, M. et al., "Purification and Characterization of Human Recombinant IgE-Fc Fragments That Bind to the Human High Affinity IgE Receptor," J. Biol. Chem., 268(18):13118-13127 (Jun. 1993).

Beasley, R. et al., "Prevalence and etilogy of asthma," J. Allergy Clin. Immunol. 105(2)(Part 2):S466-S472 (2000).

Bellmann, K., et al., "Potential risk of oral insulin with adjuvant for the prevention of Type I diabetes: a protocol effective in NOD mice may exacerbate disease in BB rats", Diabetologia, vol. 41, pp. 844-847, 1998.

Bielekova, B., et al., "Encephalitogenic potential of the myelin basic protein peptide (amino acids 83-99) in multiple sclerosis: results of a phase II clinical trial with an altered peptide ligand", Nat Med., vol. 6, No. 10, pp. 1167-1175, Oct. 2000.

Blanas, E. et al., "Induction of Autoimmune Diabetes by Oral Administration of Autoantigen", Science, vol. 274, pp. 1707-1709, Dec. 6, 1996.

Blondel, A. et al., "Engineering the quaternary structure of an exported protein with a leucine zipper," Protein Engineering,4(4):457-461 (1991).

Borel and Borel, A novel technique to link either proteins or peptides to gammaglobulin to construct tolerogens, J Immunol Methods. Feb. 9, 1990;126(2):159-68.

Borel and Borel, Oligonucleotide linked to human gammaglobulin specifically diminishes anti-DNA antibody formation in cultured lymphoid cells from patients with systemic lupus erythematosus J Clin Invest. Dec. 1988;82(6):1901-7.

Bowie, James U., et al., "Deciphering the Message in Protein Sequences: Tolerance to Amino Acid Substitutions", Science, vol. 247, pp. 1306-1310, Mar. 16, 1990.

Boyce and Austen, "No Audible Wheezing: Nuggets and Conundrums from Mouse Asthma Models," *JEM*, 201:(12) 1869-1873 (2005).

Brazis, P., et al., "Stem cell factor enhances IgE-mediated histamine and TNFα release from dispersed canine cutaneous mast cells", Veterinary Immunology and Immunopathology, vol. 75, pp. 97-108, 2000.

Breiteneder, H, PhD, et al., "Complementary DNA cloning and expression in *Escherichia coli* of Aln g I, the major allergen in pollen of alder (*Alnus glutinosa*)", J Allergy Clin. Immunol., vol. 90, No. 6, pp. 909-917, 1992.

Bridges, S. L., Jr., MD, PhD, et al., "T-cell Receptor Peptide Vaccination in the Treatment of Rheumatoid Arthritis", Emerging Therapies for Rheumatoid Arthritis, vol. 24, No. 3, pp. 641-651, 1998.

Burks, A. W. et al., "Mapping and mutational analysis of the IgE-binding epitopes on Ara h 1, a legume vicilin and a major allergen in peanut hypersensitivity," Eur. J. Biochem., 245:334-339, 1997.

Cambier, J. C., "Inhibitory receptors abound?" Proc. Natl. Acad. Sci. USA, 94:5993-5995 (1997).

Campbell, K. A., et al., "Co-crosslinking FcεRII/CD23 and B cell surface immunoglobulin modulates B cell activation", Eur. J. Immunol., vol. 22, pp. 2107-2112, 1992.

Casares, S. et al. "Engineering and characterization of a murine MGC class 11-immunoglobulin chimera expressing an immunodominant CD4 T viral epitope" *Protein Engineering* 10(11):1295-1301 (1997).

Casares, S. et al., "Antigen-specific Signaling by a Soluble, Dimeric Peptide/Major Histocompatibility Complex Class II/Fc Chimera Leading to T helper Cell Type 2 Differentiation," J. Exp. Med. 190:543-553, (Nov. 1999).

Castells, M., M.D., Ph.D., "Mast Cells: Molecular and Cell Biology", The Internet Journal of Asthma, Allergy and Immunology, vol. 11N1, pp. 1-17, 1999.

Chaillous, L, et al., "Combined analysis of islet cell antibodies which cross-react with mouse pancreas, antibodies to the Mr 64,000 islet protein, and antibodies to glutamate decarboxylase in subjects at risk for IDDM", Diabetologia, vol. 37, pp. 491-499,1994.

Chaillous, L. et al., "Oral insulin administration and residual β-cell function in recent-onset type 1 diabetes: a multicentre randomized controlled trial", The Lancet, vol. 356, pp. 545-549, 2000.

Chan, P. L. et al., "Regulation of the Immune Response," Immunology, 21:967-981 (1971).

Coffman and Hessel, "Nonhuman Primate Models of Asthma," *JEM*, 201:(12) 1875-1879 (2005).

Costa, M. A. et al., "The IgE-binding epitopes of rPar j 2, a major allergen of *Parietaria judaica* pollen, are heterogeneously recognized among allergic subjects," Allergy 55:246-250 (2000).

Couzin, J., et al., "Diabetes' Brave New World", Science, vol. 300, pp. 1862-1865, Jun. 2003.

Cunningham, Brian C., et al., "High-Resolution Epitope Mappin of hGH-Receptor Interactions by Alanine-Scanning Mutagenesis", Science, vol. 244, pp. 1081-1085, Jun. 2, 1989.

Daëron, M. et al., "Regulation of High-affinity IgE Receptor-mediated Mast Cell Activation by Murine Low- affinity IgG Receptors,". J. Clin. Invest., 95:577-585 (Feb. 1995).

Daëron, M. et al., "The Same Tyrosine-Based Inhibition Motif, in the Intra-cytoplasmic Domain of FCγRIIB, Regulates Negatively BCR-, TCR-, and FcR-Dependent Cell Activation," Immunity, 3:635-646 (Nov. 1995).

Daëron, M., "Fc Receptor Biology," Annu. Rev. Immunol., 15:203-234 (1997).

Daēron, Marc, "Fcγ-RIIB as potential therapeutic targets for allergic diseases", NAID Symposium 1221, Rethinking Immunotherapy for the Twenty First Century: Bench to Bedside, presented at the Annual Meeting of the American Academy of Allergy, Allergy Asthma & Immunology, Mar. 16-21, 2001 New Orleans, LA.

Davidson, A., et al, "Autoimmune Diseases" , N. Engl. J. Med., vol. 345, No. 5, pp. 340-350, Aug. 2, 2001.

De Lara, J.M. Tunon, "Immunoglobulines E et cellules de l'inflamation," Rev. Mal. Resp., 13:27-36 (1996).

Dombrowicz, D., et al., "Anaphylaxis Mediated Through a Humanized High Affinity IgE Receptor", The Journal of Immunology, vol. 157, pp. 1645-1651,1996.

Elias et al., Post translational Addition of an Argine Moiety to Acidic NH2 Termini of Proteins Is Required for Their Recognition by Ubiquitin-Protein Ligase, J. Biol. Chem., vol. 265, No. 26, pp. 15511-15517, Sep. 1990.

Ellison J. et al., "Linkage and sequence homology of two human immunoglobulin γ heavy chain constant region genes," Proc. Nat. Acad. Sci. USA, 79:1984-1988 (1982).

Ellison J. W. et al., "The nucleotide sequence of a human immunoglobulin cγ1 gene" Nucl. Acids Res., 10(13):4071-4079 (1982).

Fiebiger, E. et al., "Anti-FcεRIa Autoantibodies in Autoimmune-mediated Disorders. Identification of a Structure-Function Relationship," J. Clin. Invest 101:243-251 (Jan. 1998).

Fiebiger, E. et al., "Serum IgG Autoantibodies Directed against the a Chain of FcE RI: A Selective Marker and Pathogenic Factor for a Distinct Subset of Chronic Urticaria Patients?" The Journal of Clinical Investigation 96:2606-2612 Dec. 1995.

Fridman, W. H., "Fc receptors and immunoglobulin binding factors," FASEB J., 5(12):2684-2690 (1991).

Gale, E. AM., "Oral tolerance and autoimmune diabetes—will hope triumph over experience?", The Lancet, vol. 356, Aug. 12, 2000.

Genain, C. P., et al., "Late Complications of Immune Deviation Therapy in a Nonhuman Primate", Science, vol. 274, Dec. 20, 1996.

Gerber J. S. et al. "Reversing Lipopolysaccharide Toxicity by Ligating the Macrophage Fcγ Receptors," The Journal of Immunology, 166:6861-6868 (2001).

Germain, R.N., "The T Cell Receptor for Antigen: Signaling and Ligand Discrimination", The Journal of Biological Chemistry, vol. 276, No. 38, pp. 35223-35226, Jul. 2, 2001.

Gold, D. P., et al., "T-Cell Receptor Peptides as Immunotherapy for Autoimmune Disease", Critical Reviews™ in Immunology, vol. 17, pp. 507-510, 1997.

Gollnick, S. 0. et al., "Isolation, Characterization, and Expression of cDNA Clones Encoding the Mouse Fc Receptor for IgE (FcεRII)$^1$" The Journal of Immunology 144(5):1974-1982 (1974).

Goodkin, D. E., et al., "A phase I trial of solubilized DR2:MBP84-102 (AG284) in multiple sclerosis", Neurology, vol. 54, pp. 1414-1420, 2000.

Guo, C. B., et al., "Identification of IgE-bearing Cells in the Late-phase Response to Antigen in the Lung as Basophils", American J. Respir. Cell Mol. Biol., vol. 10, No. 4, pp. 384-390,1994.

Harrison, L. C. et al., "Antigen-specific therapy for autoimmune disease," Curr. Opin. Immunol., 12:704-711 (2000).

Haselden, B. M., et al., "Immunoglobulin E-Independent Major Histocompatibility Complex-Restricted T Cell Peptide Epitope-induced Late Asthmatic Reactions", J. Exp. Med., vol. 189, No. 12, pp. 1885-1894, Jun. 21, 1999.

Hayami, K. et al., "Molecular Cloning of a Novel Murine Cell-surface Glycoprotein Homologous to Killer Cell Inhibitory Receptors," J. Biol. Chem., 272 11 :7320-7327 1997.

Hellman, L., "Characterization of four novel 6 chain of mRNA and a comparative analysis of genes for immunoglobulin E in rodents and man," Eur. J. Immunol. 23:159-167 1993.

Helm, B. A., et al., "Identification of the High Affinity Receptor Binding Region in Human Immunoglobulin E", The Journal of Biological Chemistry, vol. 271, No. 13, Issue of Mar. 29, pp. 7494-7500, 1996.

Henz, B. M., et al., "Urticaria—New Developments and Perspectives", Hautarzt, vol. 51, pp. 302-308, 2000.

Hide, M. et al., "Autoantibodies against the high-affinity IgE receptor as a cause of histamine release in chronic urticaria," N. En I. J. Med., 328:1599-1604 (1993).

Hulett, M. D., et al., "Fine Structure Analysis of Interaction of FcεRI with IgE", The Journal of Biological Chemistry, vol. 274, No. 19, pp. 13345-13352, 1999.

Immunovision (Brochure), "La/SS-B", Purified Antigens for Autoimmune Testing, (http://www.immunovision.com/pg0014.htm), Jul. 30, 2001.

Ji, Tae H., et al., "Bifunctional Reagents", Methods of Enzymology, vol. 91, pp. 581-609, 1983.

Kabat, Sequences of Proteins of Immunological Interest, vol. III Fifth Ed. (1991).

Kaplan, "Urticaria and Angioedema," *Inflammation: Basic Principles and Clinical Correlates*, (Gallin and Snyderman Eds.), Chapter 35: 667-678 Raven Press, NY (1988).

Kaplan, A. P., "Urticaria and Angioedema," Inflammation: Basic Principles and Clinical Correlates,(Gallin and Snyderman eds.), 3$^{rd}$ Edition, Lippincott & Wilkins, Philadelphia, 1999, pp. 915-928.

Kappos, L., et al., "Induction of a non-encephalitogenic type 2 T helper-cell autoimmune response in multiple sclerosis after administration of an altered peptide ligand in a placebo-controlled, randomized phase II trial", Nature Medicine, vol. 6, No. 10, pp. 1176-1182, Oct. 2000.

Katz, H. R., "gp49BE and Its Related Family of Counterregulatory Receptors of the Immunoglobulin Superfamily," Int. Arch. Allergy Immunol., 118:177-179 (1999).

Kawabori, S., et al., "Existence of c-*kit* Receptor-Positive, Tryptase-Negative, IgE-Negative Cells in Human Allergic Nasal Mucosa: A Candidate for Mast Cell Progenitor", International Archives of Allergy and Immunology, vol. 112, pp. 36-43, 1997.

Kepley et al., "FcεRI-FcγRII, Coaggregation inhibits IL-16 production fro human langerhans-like dendric cells", Clinical Immunology, vol. 108, No. 89-94, 2003.

Kepley, C., et al., "Identification and Partial Characterization of a Unique Marker for Human Basophils", The Journal of Immunology, vol. 154, pp. 6548-6555, 1995.

Kepley, C., et al., "Purification of human basophils by density and size alone", Journal of Immunological Methods, vol. 175, pp. 1-9, 1994.

Kepley, C., et al., "The identification and characterization of umbilical cord blood-derived human basophils", Journal of Leukocyte Biology, vol. 64, pp. 474-483, 1998.

Kikutani, H. et al., "Molecular Structure of Human Lymphocyte Receptor for Immunoglobulin E," Cell 47:657-665 (Dec. 1986).

Kinet, J-P, "The High-Affinity IgE Receptor (FcεRI): From Physiology to Pathology", Annu. Rev. Immunol., vol. 17, pp. 931-972, 1999.

Kisselev, A. F., "Proteasome Active Sites Allosterically Regulat Each Other, Suggesting a Cylical Bite-Chew Mechanism for Protein Breakdown", Molecular Cell, vol. 4, pp. 395-402, Sep. 1999.

Kondo et al., "Cloning of CdnAs for New Subtypes of Murine Low-Affinity Fc Receptor for IgE (FcεRII/CG23)," Int. Arch. Immunol., 105:38-48 (1994).

Krauss, S. et al., "Recombinant CD4-IgE, a novel hybrid molecule, inducing basophils to respond to human immunodeficiency virus (HIV) and HIV-infected target cells," Fur. J. Immunol., 25(1):192-199 (1995).

Krawinkel, U. et al., "Comparison of the hinge-coding segments in human immunoglobulin gamma heavy chain genes and the linkage of the gamma 2 and gamma 4 subclass genes," The EMBO Journal, 1(4):403-407 (1982).

Landschulz, W. H. et al., "The Leucine Zipper: A Hypothetical Structure Common to a New Class of DNA Binding Proteins," Science 240:1759-1764 (1988).

Legge, K. L. et al.,"Presentation of a T Cell Receptor Antagonist Peptide by Immunoglobulins Ablates Activation of T Cells by a Synthetic Peptide or Proteins Requiring Endocytic Processing," J. Exp. Med.,185(6):1043-1053 (Mar. 1997).

Legge, K. L. et al.,"Coupling of Peripheral Tolerance to Endogenous Interleukin 10 Promotes Effective Modulation of Myelin-activated T Cells and Ameliorates Experimental Allergic Encephalomyelitis," J. Exp. Med., 191(12):2039-2051 (Jun. 2000).

Liénard, H., et al., "Signal Regulatory Proteins Negatively Regulate Immunoreceptor-dependent Cell Activation", The Journal of Biological Chemistry, vol. 274, No. 45, Issue of Nov. 5, pp. 32493-32499, 1999.

Liidin, C. et al., "Cloning and expression of the cDNA coding for a human lymphocyte IgE receptor," The EMBO Journal, 6(1):109-114 (1987).

Lin, S., et al., "Giving Inhibitory Receptors a Boost", Science's Compass, vol. 291, pp. 445-446, Jan. 19, 2001.

Luckey, C. J., et al., "Differences in the Expression of Human Class I MHC Alleles and Their Associated Peptides in the Presence of Proteasome Inhibitors", The Journal of Immunology, vol. 167, pp. 1212-1221, 2001.

Lu-Kuo, J. M. et al., "gp49B1 Inhibits IgE-initiated Mast Cell Activation through Both Immunoreceptor Tyrosine-based Inhibitory Motifs, Recruitment of *src* Homology 2 Domain-containing Phosphatase-1, and Suppression of Early and Late Calcium Mobilization," J. Biol. Chem., 274(9):5791-5796 (1999).

Lyczak, J. B., et al., "Expression of Novel Secreted Isoforms of Human Immunoglobulin E Proteins", The Journal of Biological Chemistry, vol. 271, No. 7, Issue of Feb. 16, pp. 3428-3436, 1996.

Machiels, J. J., et al., "Allergen-antibody complexes can efficiently prevent seasonal rhinitis and asthma in grass pollen hypersensitive patients", Allergy, vol. 46, pp. 335-348, 1991.

Machiels, J. J., et al., "Allergic Bronchial Asthma Due to *Dermatophagoides pteronyssinus* Hypersensitivity Can Be Efficiently Treated by Inoculation of Allergen-Antibody Complexes", The American Society for Clinical Investigation, Inc., vol. 85, pp. 1024-1035, 1990.

Machiels, J. J., et al., "Complexes of grass pollen allergens and specific antibodies reduce allergic symptoms and inhibit the seasonal increase of IgE antibody", Clinical and Experimental Allergy, vol. 20, pp. 653-660, 1990.

Machiels, J. J., et al., "Significant Reduction of Nonspecific Bronchial Reactivity in Patients with *Dermatophagoides pteronyssinus*-sensitive Allergic Asthma under Therapy with Allergen-Antibody Complexes", Am. Rev. Respir. Dis., vol. 147, pp. 1407-1412, 1993.

Malbec, 0. et al., "Negative Regulation of Hematopoietic Cell Activation and Proliferation by FcγRIIB," Curr. Top. Microbiol. Immunol., 244:13-27,1999.

Marks, M. S. et al., "Protein Targeting by Tyrosine- and Di-leucine-based Signals: Evidence for Distinct Saturable Components", The Journal of Cell Biology, vol. 135, No. 2, pp. 341-354, Oct. 1996.

Max, E. E. et al., "Duplication and Deletion in the Human Immunoglobulin E Genes," Cell 29:691-699 (Jun. 1992).

McDevitt et al, Proc Natl Acad Sci USA 101(2): 14627-14630, Oct. 2004.

McFarland, H. F., "Complexities in the Treatment of Autoimmune Disease", Science, vol. 274, Dec. 20, 1996.

McKnight, Steven Lanier, "Molecular Zippers in Gene Regulation", Scientific American, pp. 54-64, Apr. 1991.

Metcalfe, D. D. et al., "Mast Cells," Physiological Reviews, 77(4):1033-1079 (Oct. 1997).

Mikayama, T., et al., "Molecular cloning and functional expression of cDNA encoding gycoslaytion-inhibiting factor", Proc. Natl. Acad. Science, vol. 90, pp. 10056-10060, Nov. 1993.

Milgrom, H., et al., "Treatment of Allergic Asthma with Monoclonal Anti-IgE Antibody", The New England Journal of Medicine, vol. 341, No. 26, pp. 1966-1973, Dec. 23, 1999.

Minerd, J., "Experimental Therapy Stops Allergic Reactions in Mice", *NIAID* News, pp. 1-3, May 2002.

Mocci, S., et al., "The role of autoantigens in autoimmune disease", Current Opinion in Immunology, vol. 12, pp. 725-730, 2000.

Moreland, L. W., et al., "T Cell Receptor Peptide Vaccination in Rheumatoid Arthritis—A Placebo-Controlled Trial Using a Combination of $V_{62}$ 3, $V_\beta$14, and $V_\beta$17 Peptides", Arthritis & Rheumatism, vol. 41, No. 11, pp. 1919-1929, Nov. 1998.

Moreland, L. W., et al., "Vβ17 T Cell Receptor Peptide Vaccination in Rheumatoid Arthritis: Results of Phase I Dose Escalation Study", The Journal of Rheumatology, vol. 23, No. 8, pp. 1353-1362, 1966.

Mustelin, T. et al., "Lymphocyte Activation: The coming of the protein tyrosine phosphatases," Front. Biosci. 3:d1060-1096 (1998).

Nakagawa, T., et al., "Immunotherapy of Allergic Diseases", Int. Arch. Allergy Immunol., vol. 102, pp. 117-120, 1993.

Naquet, P., et al., "T Cell Autoreactivity to Insulin in Diabetic and Related Non-Diabetic Individuals", The Journal of Immunology, vol. 140, No. 8, pp. 2569-2578, Apr. 15, 1988.

National Institute of Allergy and Infectious Diseases, Understanding Autoimmune Disease—What are some Examples of Autoimmune Diseases: Rheumatoid Arthritis. (http://www.niaid.nih.gov/publications/autoimmune/examples.htm), Jul. 11, 2001.

Nepom, G. T. et al., "Identification and modulation of a naturally processed T cell epitope from the diabetes-associated autoantigen human glutamic acid decarboxylase 65 (Hgad65)," Proc. Natl. Acad. Sci. USA, 98(4):1763-1768 (2001).

Nepom, G. T., "Glutamic acid decarboxylase and other autoantigens in IDDM", Current Opinion in Immunology, vol. 7, pp. 825-830, 1995.

Ngo et al., In The Protein Folding Problem and Tertiary Structure Prediction, 1994, Merz, et al., (ed.), Birkhauser, Boston, MA, pp. 433 and 492.

Ngo, J. T. et al., "Computational Complexity, Protein Structure Prediction, and the Levinthal Paradox," The Protein Folding Problem and Tertiary Structure Prediction, 1994, Merz et al., (eds.), Birkhauser, Boston, MA, pp. 433 and 492-495.

Oliver, J. M. et al., "Immunologically mediated signaling in basophils and mast cells: finding therapeutic targets for allergic diseases in the human FcϵR1 signaling pathway," Immunopharmacology, 48:269-281 (2000).

Osborne, M. A., et al., "The Inositol 5'-Phosphatase SHIP Binds to Immunoreceptor Signaling Motifs and Responds to High Affinity IgE Receptor Aggregation", The Journal of Biological Chemistry, vol. 271, No. 46, pp. 29271-29278, 1996.

O'Shea, E. K. et al., "Evidence That the Leucine Zipper Is a Coiled Coil," Science, 243: 538-542 (1989).

Ota, K. et al., "T-cell recognition of an immunodominant myelin basic protein epitope in multiple sclerosis," Nature, 346:183-187 (1990).

Ott, V. L. et al., "Activating and inhibitory signaling in mast cells: New opportunities for therapeutic *intervention?" J. Allergy Clin. Immunol* ., 106(3):429-440 (2000).

Pamer, E., et al., "Mechanisms of MHC Class I—Restricted Antigen Processing", Annu. Rev. Immunol., vol. 16, pp. 323-358, 1998.

Peat, J. K. et al., "Reversing the trend: Reducing the prevalence of asthma," J. Allergy Clin. Immunol., 103(1)(Part 1):1-10 (1999).

Peng, C. et al., "A New Isoform of Human Membrane-Bound IgE," The Journal of Immunology, 148(1):129-136 (Jan. 1992).

Phillips, Nancy E., et al., "Cross-Linking of B Lymphocyte Fcγ Receptors and Membrane Immunoglobulin Inhibits Anti-Immunoglobulin-Induced Blastogenesis", The Journal of Immunology, vol. 132, No. 2, pp. 627-632, Feb. 1984.

Pivnyuk, V. I., et al., "Human Low-Affinity IgE Receptor; cDNA from Cell Line 1B and Its Expression in Peripheral Blood Cells", Molecular Biology, vol. 28, No. 4, Part 2, pp. 549-552, 1994.

Pozzilli, P., et al., "No effect of oral insulin on residual beta-cell function in recent-onset Type I diabetes (the IMDIAB VII)", Diabetologia, vol. 43, pp. 1000-1004, 2000.

Presta, L. et al., "The Binding Site on Human Immunoglobulin E for Its High Affinity Receptor," J. Biol. Chem., 269 42 :26368-26373 1994.

Rabjohn, P. et al., "Molecular cloning and epitope analysis of the peanut allergen Ara h 3," J. Clin. Invest.,103(4):535-542 (1999).

Rock, K. L., et al., "Degradation of Cell Proteins and the Generation of MHC Class I-Presented Peptides", Annu. Rev. Immunol., vol. 17, pp. 739-779, 1999.

Ruckert, R. et al., "IL-15-IgG2b fusion protein accelerates and enhances a Th2 but not a Th1 immune response in vivo, while IL-2-IgG2b fusion protein inhibits both," Eur. J. Immunol., 28:3312-3320, (1998).

Saxon, A. et al., "Inhibition of Human IgE Production Via FcϵR-II Stimulation Results From a Decrease in the mRNA for Secreted But not Membrane £ H Chains," The Journal of Immunology, 147(11):4000-4006,(Dec. 1991).

Schmidt-Dorr, T. et al., "Construction , Purification, and Characterization of a Hybrid Protein Comprising the DNA Binding Domain of the LexA Repressor and the Jun Leucine Zipper: A Circular Dichroism and Mutagenesis Study", Biochemistry, 30:9657-9664 (1991).

Schwartz, L. B., M.D., Ph.D., et al., "Development of markers for human basophils and mast cells", J. Allergy Clin. Immunol., vol. 94, No. 6, Part 2, pp. 1231-1240, 1994.

Sharma, S. D., et al., "Antigen-specific therapy of experimental allergic encephalomyelitis by soluble class II major histocompatibility complex—peptide complexes", Proc. Natl. Acad. Sci. USA, vol. 88, pp. 11465-11469, Dec. 1991.

Shields, R. et al., "High Resolution Mapping of the Binding on Human IgG1 for FcγRI, FcγRII, FcγRIII and FcRn and Design of IgG1 Variants with Improved Binding to the FcγR", The Journal of Biological Chemistry, vol. 276, No. 9, pp. 6591-6604, 2001.

Shingo Yabuuchi, et al., "Anti-Cd23 Monoclonal Antibody (IgE Inhibition Involves the Fc Portion of the Molecules", Abstract 597, J. Allergy Clin. Immunol., vol. 107, No. 2, Feb. 2001.

Sinclair, N. R., "Why So Many Coinhibitory Receptors?" Scand. J. Immunol. 50:10-13 (1999).

Skolnick, J. et al., "From genes to protein structure and function: novel applications of computational approaches in the genomic era," Trends in Biotech., 18(1):34-39 (Jan. 2000).

Sliedregt, L., et al., "Design and Synthesis of a Multivalent Homing Device for Targeting to Murine CD22", Bioorganic & Medicinal Chemistry, vol. 9, pp. 85-97, 2001.

Spack, E. G., et al., "Induction of Tolerance in Experimental Autoimmune Myasthenia Gravis with Solubilized MHC Class II: Acetylcholine Receptor Peptide Complexes", Journal of Autoimmunity, vol. 8, pp. 787-807, 1995.

Stanley, J. S. et al., "Identification and Mutational Analysis of the Immunodominant IgE Binding Epitopes of the Major Peanut Allergen Ara h 2," Arch. Biochem. Biophys., 342 2 :244-253 1997.

Steinman, L. et al., "Antigen Specific Immunotherapy of Multiple Sclerosis", Journal of Clinical Immunology, vol. 21, No. 2, pp. 93-98, 2001.

Steinman, L., et al., "Prospects for Specific Immunotherapy in Myasthenia Gravis" FASEB J.; 4(10):2726-31, Jul. 1990, (abstract).

Stenmark, Harald, et al., "Endosomal Localization of the Autoantigen EEA1 is Mediated by a Zinc-Binding FYVE Finger", The Journal of Biological Chemistry, vol. 271, No. 39, pp. 24048-24054, Sep. 27, 1996.

Stevenson, G. T. et al., "Conjugation of Human Fcγ in Closed-Hinge or Open-Hinge Configuration to Fab'y and Analogous Ligands," J. Immunol., 158(5):2242-50 (Mar. 1997).

Stryer, L. et al, Biochemistry, Third Edition, W. H. Freeman Company, New York, New York, pp. 31-33, 1998.

Sutterwala, F. S. et al., "Reversal of Proinflammatory Responses by Ligating the Macrophage Fcγ Receptor Type I," J Exp. Med., 188(1):217-222 (Jul. 1998).

Sutterwala, F. S. et al., "Selective Suppression of Interleukin-12 Induction after Macrophage Receptor Ligation," J. Exp. Med., 185(11):1977-1985 (Jun. 1997).

Takahashi, N. et al., "Structure of Human Immunoglobulin Gamma Genes: Implications for Evolution of a Gene Family," Cell, 29:671-679 (1982).

Tan EM, "Antinuclear Antibodies: Diagnostic Markers for Autoimmune Diseases and Probes for Cell Biology", (abstract), Adv Immunol 1989, 44:93-151.

Tao et al, J Immunology 143: 2595-2601, Oct. 1989.

Targoff IN, Autoantibodies to Aminoacyl-Transfer RNA Synthetases for Isoleucine and Glycine. Two Additional Synthetases are Antigenic in Myositis; J Immunol, 144(5):1737-1743, Mar. 1, 1990, (abstract).

TePas, E. C., et al, "Immunotherapy of asthma and allergic diseases", Current Opinion in Pediatrics, vol. 12, pp. 574-578, 2000.

Tisch et al, J Immunology 166: 2122-2132, Feb. 2001.

Tunon, J. M. et al., "Immunoglobines E et cellules de l'inflammation", Rev. Mal. Resp., vol. 13, pp. 27-36, 1996.

U.S. Department of Health and Human Services, "Sequences of Proteins of Immunological Interest", vol. II and vol. III, Fifth Edition, Table of Contents, pp. iii-xi, 1991.

van Rossenberg, S. M. W., et al, "A Structure-Function Study of Ligand Recognition by CD22β", Journal of Biological Chemistry, vol. 276, No. 16, Issue of Apr. 20, pp. 12967-12973, 2001.

van Rossenberg, S. M. W., et al., "A Structure-Function Study of Ligand Recognition by CD2213", The Journal of Biological Chemistry, vol. 276, No. 16, pp. 12967-12973, 2001.

Van Venrooij, W.J., Venroij Research Team, Research Topics, General Introduction, "Autoantigens", (abstract), Department of Biochemistry, University of Nijmegen, Jul. 11, 2001.

Vanderlugt et al , J immunology 164: 670-678, 2000.

Varshavsky, A., "The N-End Rule", vol. 69, pp. 725-735, May 29, 1992.

Villadangos, J. A.., "Proteases involved in MHC class II antigen presentation", Immunological Reviews, vol. 172, pp. 109-120, 1999.

Villadangos, Jose A., "Proteolysis in MHC Class II Antigen Presentation: Who's in Charge?", Immunity, vol. 12, pp. 233-239, Mar. 2000.

Wagtmann, N.,"gp49: An Ig-like Receptor with Inhibitory Properties on Mast Cells and Natural Killer Cells," Current Top. Microbial. Immunol., 244:107-113 (1999).

Wallace, R. B. et al., "Oligonucleotide Probes for the Screening of Recombinant DNA Libraries," Methods Enzymol., 152:432-441 (1987).

Wallner, Barbara P., Short Analytical Review, Peptide Therapy for Treatment of Allergic Diseases, Clinical Immunology and Immunopathology, vol. 80, No. 2, August, pp. 105-109, 1996.

Wan, Tommy, et al., "The Crystal Structure of IgE Fc Reveals an Asymmetrically Bent Conformation", Nature Immunology, vol. 3, No. 7, pp. 681-686, Jul. 2002.

Wang, M., et al., "Early IL-4 Production Driving Th2 Differentiation in a Human in Vivo Allergic Model Is Mast Cell Derived", Clinical Immunology, vol. 90, No. 1, pp. 47-54, 1999.

Wardrop, III, R.M., et al, Oral Tolerance in the Treatment of Inflammatory Autoimmune Disease, Inflamm. res., 48, pp. 106-119, 1990.

Warrant et al, J Neurol Sci 133(1-2): 85-94, Nov. 1995, abstract only.

Warren, K. G., "Increased synthetic peptide specificity of tissue-CSF bound anti-MBP in multiple sclerosis", Journal of Neuroimmunology, vol. 43, pp. 87-96, 1993.

Warren, K. G., "Synthetic peptide specificity of anti-myelin basic protein from multiple sclerosis cerebrospinal fluid", Journal of Neuroimmunology, vol. 39, pp. 81-90, 1992.

Warren, K.G., et al, "Fine specificity of the antibody response to myelin basic protein in the central nervous system in multiple sclerosis: the minimal B-cell epitope and a model of its features", Proc. Natl. Acad. Sci. USA, vol. 92, pp. 11061-11065, Nov. 1995.

Warren, K.G., et al, "Tolerance induction to myelin basic protein by intravenous synthetic peptides containing epitope $P_{85}$VVHFFKNIVTP$_{96}$ in chronic progressive multiple sclerosis", Journal of Neurological Sciences, vol. 152, pp. 31-38, 1997.

Warren, KG, et al., "Administration of Myelin Basic Protein Synthetic Peptides to Multiple Sclerosis Patients", (abstract), J. Neurol. Sci., vol. 133, No. 1-2, pp. 85-94, Nov. 1995.

Watson, J. L. et al., "Molecular cloning and sequencing of the low-affinity IgE receptor (CD23) for horse and cattle," Vet. Immunol. Immunopathol.,73:323-329 (2000).

Watts, C., "Antigen processing in the endocytic compartment", Current Opinion in Immunology, vol. 13, pp. 26-31, 2001.

Watts, C., "Capture and Processing of Exogenous Antigens for Presentation on MHC Molecules", Annu. Rev. Immunol., vol. 15, pp. 821-850, 1997.

Webster's II New Riverside University Dictionary is to keep something from happening, to warding off illness or disease (see p. 933, 1994.

Weiner, H. L., et al., "Double-Blind Pilot Trial of Oral Tolerization with Myelin Antigens in Multiple Sclerosis", Science, vol. 259, pp. 1321-1324, Feb. 26, 1993.

Wetmur, J. G. et al., "Kinetics of Renaturation of DNA," J. Mol. Biol., 31:349-370 (1968).

Wetmur, J. G., "DNA Probes: Applications of the Principles of Nucleic Acid Hybridization," Critical Reviews in Biochemist and Molecular Biology, 26 3/4 :227-259 1991.

Wines, B. D. et al., "The IgG Fc Contains Distinct Fc Receptor (FcR) Binding Sites: The Leukocyte Receptors FcγRI and FcγR11a Bind to a Region in the Fc Distinct from That Recognized by Neonatal FcR and Protein A," J. Immunol., 164 10 :5313-5318 2000.

Wucherpfennig, K. W., et al, "Recognition of the Immunodominant Myelin Basic Protein Peptide by Autoantibodies and HLA-DR2-restricted T Cell Clones from Multiple Sclerosis Patients", J. Clin. Invest., vol. 100, No. 5, pp. 1114-1122, Sep. 1997.

Yabuuchi, S., et al., "Anti-CD23 monoclonal antibody inhibits germline Cε transcription in B cells", International Immunopharmacology, vol. 2, pp. 453-461, 2002.

Yamamoto, A.M., et al., "Anti-Titin Antibodies in Myasthenia Gravis: Tight Association with Thymoma of Nonthymoma Patients", Archives of Neurology, vol. 58, No. 6, Jun. 2001.

Yamashita, T., et al., "Expression Cloning of Complementary DNA Encoding Three Distinct Isoforms of Guinea Pig Fc Receptor for IgG1 and IgG2$_1$", The Journal of Immunology, vol. 151, No. 4, pp. 2014-2023, Aug. 15, 1993.

Yamashita, Y., et al., Inhibitory and Stimulatory Functions of Paired Ig-Like Receptor (PIR) Family in RBL-2H3 Cells[1,] The American Association of Immunologists, vol. 161, pp. 4042- 4047, 1998.

Yarden, Y. et al., "Human proto-oncogene *c-kit*: a new cell surface receptor tyrosine kinase for an unidentified U•end," EMBO J., 6 11:3341-51 1987.

Yodoi, J., et al, "Low affinity IgE receptors: regulation and functional roles in cell activation", Ige, Mast Cells and the Allergic Response, Wiley Chichester (Ciba Foundation Symposium 147) pp. 133-153, 1989.

Yoon, J-W., et al, "Control of Autoimmune Diabetes in NOD Mice by GAD Expression or Suppression in β Cells", Science, vol. 284, pp. 1183-1187, May 14, 1999.

Zhang, Z. et al., "Two Unusual Forms of Human Immunoglobulin E Encoded by Alternative RNA splicing of E Heavy Chain Membrane Exons,", *The Journal of Experimental Med.*, 176:233-243 (Jul. 1992).

Zhu et al., "A novel human immunoglobulin Fcγ-Fcε bifunctional fusion protein inhibits FcERI-mediated degranulation", *Nature Medicine*, 8:(5) 518-521 (May 2002).

Zhu, Daocheng, "A Chimeric Human-Cat Fusion Protein Blocks Cat-Induced Allergy", Nature Medicine, pp. 1-4, Mar. 2005 (published online at hhtp://www.nature.com/naturemedicine).

Zhu, Daocheng, et al., "A Novel Human Ig Fcγ-Fcε Chimeric Fusion Protein Inhibits FcεRI-Mediated Degranulation", (abstract), May 4-7, 2001.

Zhu, Daocheng, et al., "A Novel Ig Fc-γ-Fcε Chimeric Fusion Protein Inhibits FcERI Mediated Degranulation", Abstract 273, Clinical Immunology, vol. 99, No. 1, p. 193, Apr. 19, 2001.

\* cited by examiner

FIGURE 1

```
gagcccaaat cttgtgacaa aactcacaca tgcccaccgt gcccagcacc tgaactcctg  60
gggggaccgt cagtcttcct cttcccccca aacccaagg acaccctcat gatctcccgg  120
accctgagg tcacatgcgt ggtggtggac gtgagccacg aagaccctga ggtcaagttc  180
aactggtacg tggacggcgt ggaggtgcat aatgttaaga caaagccgcg ggaggagcag  240
tacaacagca cgtaccgtgt ggtcagcgtc ctcaccgtcc tgcaccagaa ctggatgaat  300
ggaaaggagt acaagtgcaa ggtctccaac aaagccctcc cagcccccat cgagaaaacc  360
atctccaaag ccaaagtgca gccccgagaa ccacaggtgt acaccctgcc cccatcccgg  420
gatgagctga ccaagaacca ggtcagcctg acctgcctgg tcaaaggctt ctatcccagc  480
gacatcgccg tggagtggga gagcaatggg cagccggaga caactacaa gaccacgcct  540
cccgtgctgg actccgtcgg ctccttcttc ctctacagca agctcaccgt ggacaagagc  600
aggtggcagc aggggaacgt cttctcatgc tccgtgatgc atgaggctct gcacaaccac  660
taccagcaga ggagcctctc cctgtctccg ggtaaa                           696
```

FIGURE 2

```
Ala Ser Thr Lys Gly Pro Ser Val Phe Pro Leu Ala Pro Ser Ser Lys
Ser Thr Ser Gly Gly Thr Ala Ala Leu Gly Cys Leu Val Lys Asp Tyr
Phe Pro Glu Pro Val Thr Val Ser Trp Asn Ser Gly Ala Leu Thr Ser
Gly Val His Thr Phe Pro Ala Val Leu Gln Ser Ser Gly Leu Tyr Ser
Leu Ser Ser Val Val Thr Val Pro Ser Ser Ser Leu Gly Thr Gln Thr
Tyr Ile Cys Asn Val Asn His Lys Pro Ser Asn Thr Lys Val Asp Lys
Lys Val Glu Pro Lys Ser Cys Asp Lys Thr His Thr Cys Pro Pro Cys
Pro Ala Pro Glu Leu Leu Gly Gly Pro Ser Val Phe Leu Phe Pro Pro
Lys Pro Lys Asp Thr Leu Met Ile Ser Arg Thr Pro Glu Val Thr Cys
Val Val Val Asp Val Ser His Glu Asp Pro Glu Val Lys Phe Asn Trp
Tyr Val Asp Gly Val Glu Val His Asn Val Lys Thr Lys Pro Arg Glu
Glu Gln Tyr Asn Ser Thr Tyr Arg Val Val Ser Val Leu Thr Val Leu
His Gln Asn Trp Met Asn Gly Lys Glu Tyr Lys Cys Lys Val Ser Asn
Lys Ala Leu Pro Ala Pro Ile Glu Lys Thr Ile Ser Lys Ala Lys Val
Gln Pro Arg Glu Pro Gln Val Tyr Thr Leu Pro Pro Ser Arg Asp Glu
Leu Thr Lys Asn Gln Val Ser Leu Thr Cys Leu Val Lys Gly Phe Tyr
Pro Ser Asp Ile Ala Val Glu Trp Glu Ser Asn Gly Gln Pro Glu Asn
Asn Tyr Lys Thr Thr Pro Pro Val Leu Asp Ser Val Gly Ser Phe Phe
Leu Tyr Ser Lys Leu Thr Val Asp Lys Ser Arg Trp Gln Gln Gly Asn
Val Phe Ser Cys Ser Val Met His Glu Ala Leu His Asn His Tyr Gln
Gln Arg Ser Leu Ser Leu Ser Pro Gly Lys
```

FIGURE 3

```
Glu Pro Lys Ser Cys Asp Lys Thr His Thr Cys Pro Pro Cys Pro Ala
Pro Glu Leu Leu Gly Gly Pro Ser Val Phe Leu Phe Pro Pro Lys Pro
Lys Asp Thr Leu Met Ile Ser Arg Thr Pro Glu Val Thr Cys Val Val
Val Asp Val Ser His Glu Asp Pro Glu Val Lys Phe Asn Trp Tyr Val
Asp Gly Val Glu Val His Asn Val Lys Thr Lys Pro Arg Glu Glu Gln
Tyr Asn Ser Thr Tyr Arg Val Val Ser Val Leu Thr Val Leu His Gln
Asn Trp Met Asn Gly Lys Glu Tyr Lys Cys Lys Val Ser Asn Lys Ala
Leu Pro Ala Pro Ile Glu Lys Thr Ile Ser Lys Ala Lys Val Gln Pro
Arg Glu Pro Gln Val Tyr Thr Leu Pro Pro Ser Arg Asp Glu Leu Thr
Lys Asn Gln Val Ser Leu Thr Cys Leu Val Lys Gly Phe Tyr Pro Ser
Asp Ile Ala Val Glu Trp Glu Ser Asn Gly Gln Pro Glu Asn Asn Tyr
Lys Thr Thr Pro Pro Val Leu Asp Ser Val Gly Ser Phe Phe Leu Tyr
Ser Lys Leu Thr Val Asp Lys Ser Arg Trp Gln Gln Gly Asn Val Phe
Ser Cys Ser Val Met His Glu Ala Leu His Asn His Tyr Gln Gln Arg
Ser Leu Ser Leu Ser Pro Gly Lys
```

FIGURE 4

```
tccacacaga gcccatccgt cttcccctTg acccgctgct gcaaaaacat tccctccaat   60
gccacctccg tgactctggg ctgcctggcc acgggctact tcccggagcc ggtgatggtg  120
acctgggaca caggctccct caacgggaca actatgacct taccagccac caccctcacg  180
ctctctggtc actatgccac catcagcttg ctgaccgtct cgggtgcgtg ggccaagcag  240
atgttcacct gccgtgtggc acacactcca tcgtccacag actgggtcga caacaaaacc  300
ttcagcgtct gctccaggga cttcaccccg cccaccgtga agatcttaca gtcgtcctgc  360
gacggcggcg ggcacttccc cccgaccatc cagctcctgt gcctcgtctc tgggtacacc  420
ccagggacta tcaacatcac ctggctggag gacgggcagg tcatggacgt ggacttgtcc  480
accgcctcta ccacgcagga gggtgagctg gcctccacac aaagcgagct caccctcagc  540
cagaagcact ggctgtcaga ccgcacctac acctgccagg tcacctatca aggtcacacc  600
tttgaggaca gcaccaagaa gtgtgcagat tcaacccga gaggggtgag cgcctaccta  660
agccggccca gcccgttcga cctgttcatc cgcaagtcgc ccacgatcac ctgtctggtg  720
gtggacctgg cacccagcaa ggggaccgtg aacctgacct ggtcccgggc cagtgggaag  780
cctgtgaacc actccaccag aaaggaggag aagcagcgca atggcacgtt aaccgtcacg  840
tccaccctgc cggtgggcac ccgagactgg atcgaggggg agacctacca gtgcagggtg  900
acccaccccc acctgcccag ggccctcatg cggtccacga ccaagaccag cggcccgcgt  960
gctgccccgg aagtctatgc gtttgcgacg ccggagtggc cggggagccg ggacaagcgc 1020
accctcgcct gcctgatcca gaacttcatg cctgaggaca tctcggtgca gtggctgcac 1080
aacgaggtgc agctcccgga cgcccggcac agcacgacgc agccccgcaa gaccaagggc 1140
tccggcttct tcgtcttcag ccgcctggag gtgaccaggg ccgaatggga gcagaaagat 1200
gagttcatct gccgtgcagt ccatgaggca gcgagcccct cacagaccgt ccagcgagcg 1260
gtgtctgtaa atcccggtaa atgacgtact cctgcctccc tccctcccag ggctccatcc 1320
agctgtgcag tggggaggac tggccagacc ttctgtccac tgttgcaatg accccaggaa 1380
gctaccccca ataaactgtg cctgctcaga gccccagtac acccattctt gggagcgggc 1440
agggc                                                             1445
```

FIGURE 5

```
Ser Thr Gln Ser Pro Ser Val Phe Pro Leu Thr Arg Cys Cys Lys Asn
Ile Pro Ser Asn Ala Thr Ser Val Thr Leu Gly Cys Leu Ala Thr Gly
Tyr Phe Pro Glu Pro Val Met Val Thr Trp Asp Thr Gly Ser Leu Asn
Gly Thr Thr Met Thr Leu Pro Ala Thr Thr Leu Thr Leu Ser Gly His
Tyr Ala Thr Ile Ser Leu Leu Thr Val Ser Gly Ala Trp Ala Lys Gln
Met Phe Thr Cys Arg Val Ala His Thr Pro Ser Ser Thr Asp Trp Val
Asp Asn Lys Thr Phe Ser Val Cys Ser Arg Asp Phe Thr Pro Pro Thr
Val Lys Ile Leu Gln Ser Ser Cys Asp Gly Gly Gly His Phe Pro Pro
Thr Ile Gln Leu Leu Cys Leu Val Ser Gly Tyr Thr Pro Gly Thr Ile
Asn Ile Thr Trp Leu Glu Asp Gly Gln Val Met Asp Val Asp Leu Ser
Thr Ala Ser Thr Thr Gln Glu Gly Glu Leu Ala Ser Thr Gln Ser Glu
Leu Thr Leu Ser Gln Lys His Trp Leu Ser Asp Arg Thr Tyr Thr Cys
Gln Val Thr Tyr Gln Gly His Thr Phe Glu Asp Ser Thr Lys Lys Cys
Ala Asp Ser Asn Pro Arg Gly Val Ser Ala Tyr Leu Ser Arg Pro Ser
Pro Phe Asp Leu Phe Ile Arg Lys Ser Pro Thr Ile Thr Cys Leu Val
Val Asp Leu Ala Pro Ser Lys Gly Thr Val Asn Leu Thr Trp Ser Arg
Ala Ser Gly Lys Pro Val Asn His Ser Thr Arg Lys Glu Glu Lys Gln
Arg Asn Gly Thr Leu Thr Val Thr Ser Thr Leu Pro Val Gly Thr Arg
Asp Trp Ile Glu Gly Glu Thr Tyr Gln Cys Arg Val Thr His Pro His
Leu Pro Arg Ala Leu Met Arg Ser Thr Thr Lys Thr Ser Gly Pro Arg
Ala Ala Pro Glu Val Tyr Ala Phe Ala Thr Pro Glu Trp Pro Gly Ser
Arg Asp Lys Arg Thr Leu Ala Cys Leu Ile Gln Asn Phe Met Pro Glu
Asp Ile Ser Val Gln Trp Leu His Asn Glu Val Gln Leu Pro Asp Ala
Arg His Ser Thr Thr Gln Pro Arg Lys Thr Lys Gly Ser Gly Phe Phe
Val Phe Ser Arg Leu Glu Val Thr Arg Ala Glu Trp Glu Gln Lys Asp
Glu Phe Ile Cys Arg Ala Val His Glu Ala Ala Ser Pro Ser Gln Thr
Val Gln Arg Ala Val Ser Val Asn Pro Gly Lys
```

FIGURE 6

```
Phe Thr Pro Pro Thr Val Lys Ile Leu Gln Ser Ser Cys Asp Gly Gly
Gly His Phe Pro Pro Thr Ile Gln Leu Leu Cys Leu Val Ser Gly Tyr
Thr Pro Gly Thr Ile Asn Ile Thr Trp Leu Glu Asp Gly Gln Val Met
Asp Val Asp Leu Ser Thr Ala Ser Thr Thr Gln Glu Gly Glu Leu Ala
Ser Thr Gln Ser Glu Leu Thr Leu Ser Gln Lys His Trp Leu Ser Asp
Arg Thr Tyr Thr Cys Gln Val Thr Tyr Gln Gly His Thr Phe Glu Asp
Ser Thr Lys Lys Cys Ala Asp Ser Asn Pro Arg Gly Val Ser Ala Tyr
Leu Ser Arg Pro Ser Pro Phe Asp Leu Phe Ile Arg Lys Ser Pro Thr
Ile Thr Cys Leu Val Val Asp Leu Ala Pro Ser Lys Gly Thr Val Asn
Leu Thr Trp Ser Arg Ala Ser Gly Lys Pro Val Asn His Ser Thr Arg
Lys Glu Glu Lys Gln Arg Asn Gly Thr Leu Thr Val Thr Ser Thr Leu
Pro Val Gly Thr Arg Asp Trp Ile Glu Gly Glu Thr Tyr Gln Cys Arg
Val Thr His Pro His Leu Pro Arg Ala Leu Met Arg Ser Thr Thr Lys
Thr Ser Gly Pro Arg Ala Ala Pro Glu Val Tyr Ala Phe Ala Thr Pro
Glu Trp Pro Gly Ser Arg Asp Lys Arg Thr Leu Ala Cys Leu Ile Gln
Asn Phe Met Pro Glu Asp Ile Ser Val Gln Trp Leu His Asn Glu Val
Gln Leu Pro Asp Ala Arg His Ser Thr Thr Gln Pro Arg Lys Thr Lys
Gly Ser Gly Phe Phe Val Phe Ser Arg Leu Glu Val Thr Arg Ala Glu
Trp Glu Gln Lys Asp Glu Phe Ile Cys Arg Ala Val His Glu Ala Ala
Ser Pro Ser Gln Thr Val Gln Arg Ala Val Ser Val Asn Pro Gly Lys
```

FIGURE 7

```
Glu Pro Lys Ser Cys Asp Lys Thr His Thr Cys Pro Pro Cys Pro Ala
Pro Glu Leu Leu Gly Gly Pro Ser Val Phe Leu Phe Pro Pro Lys Pro
Lys Asp Thr Leu Met Ile Ser Arg Thr Pro Glu Val Thr Cys Val Val
Val Asp Val Ser His Glu Asp Pro Glu Val Lys Phe Asn Trp Tyr Val
Asp Gly Val Glu Val His Asn Val Lys Thr Lys Pro Arg Glu Glu Gln
Tyr Asn Ser Thr Tyr Arg Val Val Ser Val Leu Thr Val Leu His Gln
Asn Trp Met Asn Gly Lys Glu Tyr Lys Cys Lys Val Ser Asn Lys Ala
Leu Pro Ala Pro Ile Glu Lys Thr Ile Ser Lys Ala Lys Val Gln Pro
Arg Glu Pro Gln Val Tyr Thr Leu Pro Pro Ser Arg Asp Glu Leu Thr
Lys Asn Gln Val Ser Leu Thr Cys Leu Val Lys Gly Phe Tyr Pro Ser
Asp Ile Ala Val Glu Trp Glu Ser Asn Gly Gln Pro Glu Asn Asn Tyr
Lys Thr Thr Pro Pro Val Leu Asp Ser Val Gly Ser Phe Phe Leu Tyr
Ser Lys Leu Thr Val Asp Lys Ser Arg Trp Gln Gln Gly Asn Val Phe
Ser Cys Ser Val Met His Glu Ala Leu His Asn His Tyr Gln Gln Arg
Ser Leu Ser Leu Ser Pro Gly Lys Val Glu Gly Gly Gly Gly Ser Gly
Gly Gly Gly Ser Gly Gly Gly Gly Ser Phe Thr Pro Pro Thr Val Lys
Ile Leu Gln Ser Ser Cys Asp Gly Gly Gly His Phe Pro Pro Thr Ile
Gln Leu Leu Cys Leu Val Ser Gly Tyr Thr Pro Gly Thr Ile Asn Ile
Thr Trp Leu Glu Asp Gly Gln Val Met Asp Val Asp Leu Ser Thr Ala
Ser Thr Thr Gln Glu Gly Glu Leu Ala Ser Thr Gln Ser Glu Leu Thr
Leu Ser Gln Lys His Trp Leu Ser Asp Arg Thr Tyr Thr Cys Gln Val
Thr Tyr Gln Gly His Thr Phe Glu Asp Ser Thr Lys Lys Cys Ala Asp
Ser Asn Pro Arg Gly Val Ser Ala Tyr Leu Ser Arg Pro Ser Pro Phe
Asp Leu Phe Ile Arg Lys Ser Pro Thr Ile Thr Cys Leu Val Val Asp
Leu Ala Pro Ser Lys Gly Thr Val Asn Leu Thr Trp Ser Arg Ala Ser
Gly Lys Pro Val Asn His Ser Thr Arg Lys Glu Glu Lys Gln Arg Asn
Gly Thr Leu Thr Val Thr Ser Thr Leu Pro Val Gly Thr Arg Asp Trp
Ile Glu Gly Glu Thr Tyr Gln Cys Arg Val Thr His Pro His Leu Pro
Arg Ala Leu Met Arg Ser Thr Thr Lys Thr Ser Gly Pro Arg Ala Ala
Pro Glu Val Tyr Ala Phe Ala Thr Pro Glu Trp Pro Gly Ser Arg Asp
Lys Arg Thr Leu Ala Cys Leu Ile Gln Asn Phe Met Pro Glu Asp Ile
Ser Val Gln Trp Leu His Asn Glu Val Gln Leu Pro Asp Ala Arg His
Ser Thr Thr Gln Pro Arg Lys Thr Lys Gly Ser Gly Phe Phe Val Phe
Ser Arg Leu Glu Val Thr Arg Ala Glu Trp Glu Gln Lys Asp Glu Phe
Ile Cys Arg Ala Val His Glu Ala Ala Ser Pro Ser Gln Thr Val Gln
Arg Ala Val Ser Val Asn Pro Gly Lys
```

FIGURE 10
GE2 binding to HMC-1 cells that express FcGRIIb but not FcERIa
A. Cell gating
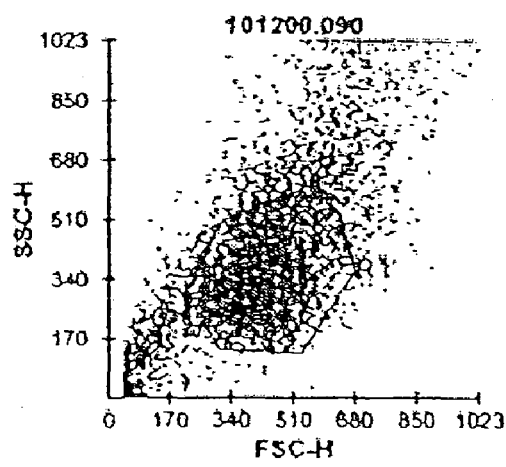
B. Control staining with goat anti-human IgG
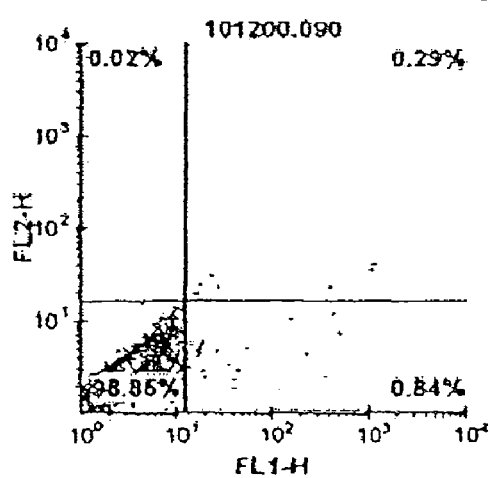
C. human IgG followed by staining with goat anti-human IgG
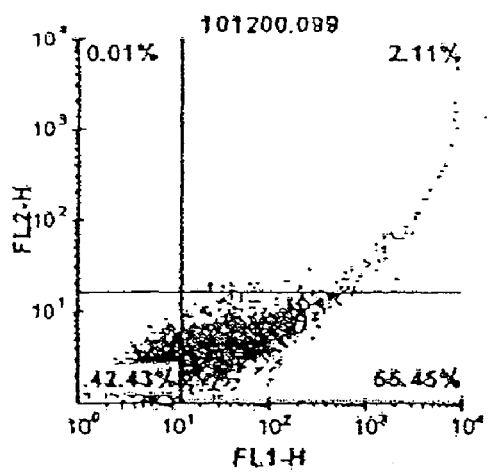
C. GE2 protein followed by staining with goat anti-human IgG
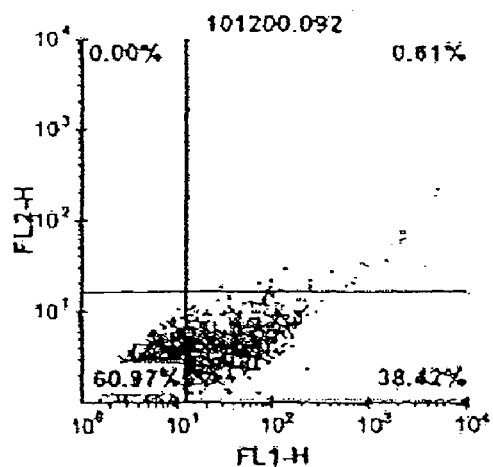

FIGURE 11
GE2 binding to 3D10 cells that express FcεRIa but not FcγRIIb
A. Cell gating on 3D10 cells which express FcERIa but not EcGR-
B. Staining with goat anti-human IgE alone
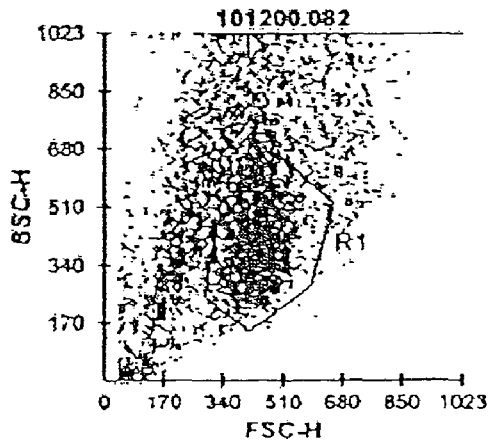
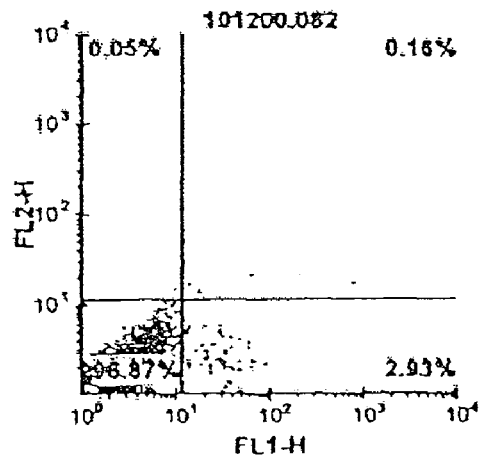
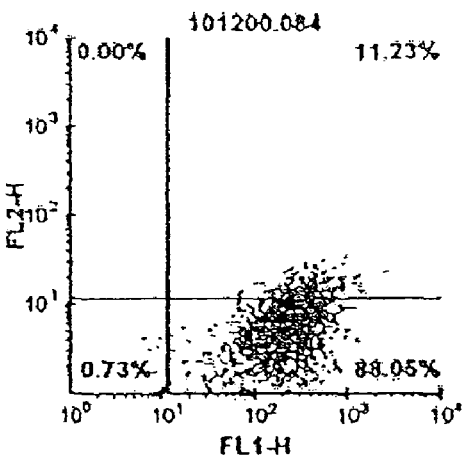
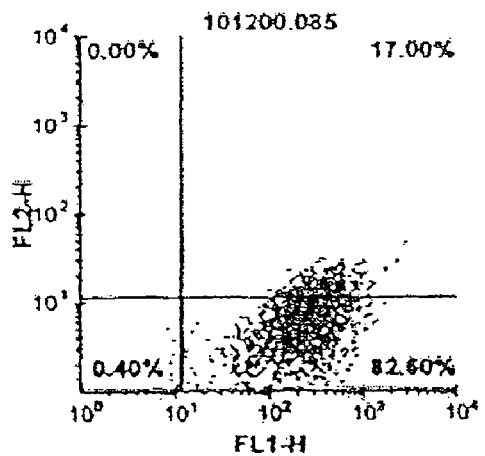
C. human IgE myeloma followed by Staining with goat anti-human IgE
D. GE2 followed by staining with goat anti-human IgE

SEQUENCE LISTING

```
<160> NUMBER OF SEQ ID NOS: 13

<210> SEQ ID NO 1
<211> LENGTH: 696
<212> TYPE: DNA
<213> ORGANISM: Homo sapiens

<400> SEQUENCE: 1
gagcccaaat cttgtgacaa aactcacaca tgcccaccgt gcccagcacc tgaactcctg      60 ggggaccgt cagtcttcct cttcccccca aaacccaagg acaccctcat gatctcccgg     120 accctgagg tcacatgcgt ggtggtggac gtgagccacg aagaccctga ggtcaagttc     180
aactggtacg tggacggcgt ggaggtgcat aatgttaaga caaagccgcg ggaggagcag     240
tacaacagca cgtaccgtgt ggtcagcgtc ctcaccgtcc tgcaccagaa ctggatgaat     300
ggaaaggagt acaagtgcaa ggtctccaac aaagccctcc cagcccccat cgagaaaacc     360
atctccaaag ccaaagtgca gccccgagaa ccacaggtgt acaccctgcc cccatcccgg     420
gatgagctga ccaagaacca ggtcagcctg acctgcctgg tcaaaggctt ctatcccagc     480
gacatcgccg tggagtggga gagcaatggg cagccggaga caactacaa gaccacgcct     540 cccgtgctgg actccgtcgg ctccttcttc ctctacagca agctcaccgt ggacaagagc     600
aggtggcagc aggggaacgt cttctcatgc tccgtgatgc atgaggctct gcacaaccac     660
taccagcaga ggagcctctc cctgtctccg ggtaaa                              696

<210> SEQ ID NO 2
<211> LENGTH: 330
<212> TYPE: PRT
<213> ORGANISM: Homo sapiens

<400> SEQUENCE: 2

Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Gln Thr
 65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125
```

```
Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Val Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asn Trp Met Asn Gly Lys Glu Tyr Lys Cys Lys Val Ser Asn
        195                 200                 205

Lys Ala Leu Pro Ala Pro Ile Glu Lys Thr Ile Ser Lys Ala Lys Val
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Val Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Gln
305                 310                 315                 320

Gln Arg Ser Leu Ser Leu Ser Pro Gly Lys
                325                 330

<210> SEQ ID NO 3
<211> LENGTH: 232
<212> TYPE: PRT
<213> ORGANISM: Homo sapiens

<400> SEQUENCE: 3

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Val Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asn Trp Met Asn Gly Lys Glu Tyr Lys Cys Lys Val Ser Asn Lys Ala
            100                 105                 110

Leu Pro Ala Pro Ile Glu Lys Thr Ile Ser Lys Ala Lys Val Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
```

-continued

```
              165                 170                 175
Lys Thr Thr Pro Pro Val Leu Asp Ser Val Gly Ser Phe Phe Leu Tyr
        180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Gln Gln Arg
        210                 215                 220

Ser Leu Ser Leu Ser Pro Gly Lys
225                 230
```

<210> SEQ ID NO 4
<211> LENGTH: 1445
<212> TYPE: DNA
<213> ORGANISM: Homo sapiens

<400> SEQUENCE: 4

| | | | | |
|---|---|---|---|---|
| tccacacaga | gcccatccgt | cttcccttg | acccgctgct | gcaaaaacat tccctccaat | 60 |
| gccacctccg | tgactctggg | ctgcctggcc | acgggctact | tcccggagcc ggtgatggtg | 120 |
| acctgggaca | caggctccct | caacgggaca | actatgacct | accagccac accctcacg | 180 |
| ctctctggtc | actatgccac | catcagcttg | ctgaccgtct | cgggtgcgtg ggccaagcag | 240 |
| atgttcacct | gccgtgtggc | acacactcca | tcgtccacag | actgggtcga caacaaaacc | 300 |
| ttcagcgtct | gctccaggga | cttcacccg | cccaccgtga | agatcttaca gtcgtcctgc | 360 |
| gacggcggcg | ggcacttccc | cccgaccatc | cagctcctgt | gcctcgtctc tgggtacacc | 420 |
| ccagggacta | tcaacatcac | ctggctggag | acgggcagg | tcatggacgt ggacttgtcc | 480 |
| accgcctcta | ccacgcagga | gggtgagctg | gcctccacac | aaagcgagct caccctcagc | 540 |
| cagaagcact | ggctgtcaga | ccgcacctac | acctgccagg | tcacctatca aggtcacacc | 600 |
| tttgaggaca | gcaccaagaa | gtgtgcagat | tccaacccga | gaggggtgag cgcctaccta | 660 |
| agccggccca | gcccgttcga | cctgttcatc | cgcaagtcgc | ccacgatcac ctgtctggtg | 720 |
| gtggacctgg | cacccagcaa | ggggaccgtg | aacctgacct | ggtcccgggc cagtgggaag | 780 |
| cctgtgaacc | actccaccag | aaaggaggag | aagcagcgca | atggcacgtt aaccgtcacg | 840 |
| tccaccctgc | cggtgggcac | ccgagactgg | atcgaggggg | agacctacca gtgcagggtg | 900 |
| acccaccccc | acctgcccag | ggccctcatg | cggtccacga | ccaagaccag cggcccgcgt | 960 |
| gctgccccgg | aagtctatgc | gtttgcgacg | ccggagtggc | cggggagccg ggacaagcgc | 1020 |
| accctcgcct | gcctgatcca | gaacttcatg | cctgaggaca | tctcggtgca gtggctgcac | 1080 |
| aacgaggtgc | agctcccgga | cgccggcac | agcacgacgc | agcccgcaa gaccaagggc | 1140 |
| tccggcttct | tcgtcttcag | ccgcctggag | gtgaccaggg | ccgaatggga gcagaaagat | 1200 |
| gagttcatct | gccgtgcagt | ccatgaggca | gcgagcccct | cacagaccgt ccagcgagcg | 1260 |
| gtgtctgtaa | atcccggtaa | atgacgtact | cctgcctccc | tccctcccag ggctccatcc | 1320 |
| agctgtgcag | tggggaggac | tggccagacc | ttctgtccac | tgttgcaatg accccaggaa | 1380 |
| gctaccccca | taaactgtg | cctgctcaga | gccccagtac | acccattctt gggagcgggc | 1440 |
| agggc | | | | | 1445 |

<210> SEQ ID NO 5
<211> LENGTH: 427
<212> TYPE: PRT
<213> ORGANISM: Homo sapiens

<400> SEQUENCE: 5

```
Ser Thr Gln Ser Pro Ser Val Phe Pro Leu Thr Arg Cys Cys Lys Asn
  1               5                  10                  15

Ile Pro Ser Asn Ala Thr Ser Val Thr Leu Gly Cys Leu Ala Thr Gly
             20                  25                  30

Tyr Phe Pro Glu Pro Val Met Val Thr Trp Asp Thr Gly Ser Leu Asn
         35                  40                  45

Gly Thr Thr Met Thr Leu Pro Ala Thr Thr Leu Thr Leu Ser Gly His
     50                  55                  60

Tyr Ala Thr Ile Ser Leu Leu Thr Val Ser Gly Ala Trp Ala Lys Gln
 65                  70                  75                  80

Met Phe Thr Cys Arg Val Ala His Thr Pro Ser Ser Thr Asp Trp Val
                 85                  90                  95

Asp Asn Lys Thr Phe Ser Val Cys Ser Arg Asp Phe Thr Pro Pro Thr
            100                 105                 110

Val Lys Ile Leu Gln Ser Ser Cys Asp Gly Gly His Phe Pro Pro
            115                 120                 125

Thr Ile Gln Leu Leu Cys Leu Val Ser Gly Tyr Thr Pro Gly Thr Ile
        130                 135                 140

Asn Ile Thr Trp Leu Glu Asp Gly Gln Val Met Asp Val Asp Leu Ser
145                 150                 155                 160

Thr Ala Ser Thr Thr Gln Glu Gly Glu Leu Ala Ser Thr Gln Ser Glu
                165                 170                 175

Leu Thr Leu Ser Gln Lys His Trp Leu Ser Asp Arg Thr Tyr Thr Cys
            180                 185                 190

Gln Val Thr Tyr Gln Gly His Thr Phe Glu Asp Ser Thr Lys Lys Cys
        195                 200                 205

Ala Asp Ser Asn Pro Arg Gly Val Ser Ala Tyr Leu Ser Arg Pro Ser
    210                 215                 220

Pro Phe Asp Leu Phe Ile Arg Lys Ser Pro Thr Ile Thr Cys Leu Val
225                 230                 235                 240

Val Asp Leu Ala Pro Ser Lys Gly Thr Val Asn Leu Thr Trp Ser Arg
                245                 250                 255

Ala Ser Gly Lys Pro Val Asn His Ser Thr Arg Lys Glu Glu Lys Gln
            260                 265                 270

Arg Asn Gly Thr Leu Thr Val Thr Ser Thr Leu Pro Val Gly Thr Arg
        275                 280                 285

Asp Trp Ile Glu Gly Glu Thr Tyr Gln Cys Arg Val Thr His Pro His
    290                 295                 300

Leu Pro Arg Ala Leu Met Arg Ser Thr Thr Lys Thr Ser Gly Pro Arg
305                 310                 315                 320

Ala Ala Pro Glu Val Tyr Ala Phe Ala Thr Pro Glu Trp Pro Gly Ser
                325                 330                 335

Arg Asp Lys Arg Thr Leu Ala Cys Leu Ile Gln Asn Phe Met Pro Glu
            340                 345                 350

Asp Ile Ser Val Gln Trp Leu His Asn Glu Val Gln Leu Pro Asp Ala
        355                 360                 365

Arg His Ser Thr Thr Gln Pro Arg Lys Thr Lys Gly Ser Gly Phe Phe
    370                 375                 380

Val Phe Ser Arg Leu Glu Val Thr Arg Ala Glu Trp Glu Gln Lys Asp
385                 390                 395                 400

Glu Phe Ile Cys Arg Ala Val His Glu Ala Ala Ser Pro Ser Gln Thr
                405                 410                 415
```

```
Val Gln Arg Ala Val Ser Val Asn Pro Gly Lys
            420                 425

<210> SEQ ID NO 6
<211> LENGTH: 320
<212> TYPE: PRT
<213> ORGANISM: Homo sapiens

<400> SEQUENCE: 6

Phe Thr Pro Pro Thr Val Lys Ile Leu Gln Ser Ser Cys Asp Gly Gly
 1               5                  10                  15

Gly His Phe Pro Pro Thr Ile Gln Leu Leu Cys Leu Val Ser Gly Tyr
            20                  25                  30

Thr Pro Gly Thr Ile Asn Ile Thr Trp Leu Glu Asp Gly Gln Val Met
        35                  40                  45

Asp Val Asp Leu Ser Thr Ala Ser Thr Thr Gln Glu Gly Glu Leu Ala
    50                  55                  60

Ser Thr Gln Ser Glu Leu Thr Leu Ser Gln Lys His Trp Leu Ser Asp
65                  70                  75                  80

Arg Thr Tyr Thr Cys Gln Val Thr Tyr Gln Gly His Thr Phe Glu Asp
                85                  90                  95

Ser Thr Lys Lys Cys Ala Asp Ser Asn Pro Arg Gly Val Ser Ala Tyr
            100                 105                 110

Leu Ser Arg Pro Ser Pro Phe Asp Leu Phe Ile Arg Lys Ser Pro Thr
        115                 120                 125

Ile Thr Cys Leu Val Val Asp Leu Ala Pro Ser Lys Gly Thr Val Asn
    130                 135                 140

Leu Thr Trp Ser Arg Ala Ser Gly Lys Pro Val Asn His Ser Thr Arg
145                 150                 155                 160

Lys Glu Glu Lys Gln Arg Asn Gly Thr Leu Thr Val Thr Ser Thr Leu
                165                 170                 175

Pro Val Gly Thr Arg Asp Trp Ile Glu Gly Thr Tyr Gln Cys Arg
            180                 185                 190

Val Thr His Pro His Leu Pro Arg Ala Leu Met Arg Ser Thr Thr Lys
        195                 200                 205

Thr Ser Gly Pro Arg Ala Ala Pro Glu Val Tyr Ala Phe Ala Thr Pro
    210                 215                 220

Glu Trp Pro Gly Ser Arg Asp Lys Arg Thr Leu Ala Cys Leu Ile Gln
225                 230                 235                 240

Asn Phe Met Pro Glu Asp Ile Ser Val Gln Trp Leu His Asn Glu Val
                245                 250                 255

Gln Leu Pro Asp Ala Arg His Ser Thr Thr Gln Pro Arg Lys Thr Lys
            260                 265                 270

Gly Ser Gly Phe Phe Val Phe Ser Arg Leu Glu Val Thr Arg Ala Glu
        275                 280                 285

Trp Glu Gln Lys Asp Glu Phe Ile Cys Arg Ala Val His Glu Ala Ala
    290                 295                 300

Ser Pro Ser Gln Thr Val Gln Arg Ala Val Ser Val Asn Pro Gly Lys
305                 310                 315                 320

<210> SEQ ID NO 7
<211> LENGTH: 569
<212> TYPE: PRT
<213> ORGANISM: Unknown
<220> FEATURE:
<223> OTHER INFORMATION: Fusion polypeptide comprising a hinge-CH2-CH3
      (IgG1) sequence and a CH2-CH3-CH4 (IgE) sequence
```

<400> SEQUENCE: 7

```
Glu Pro Lys Ser Cys Asp Lys Thr His Thr Cys Pro Pro Cys Pro Ala
 1               5                  10                  15
Pro Glu Leu Leu Gly Gly Pro Ser Val Phe Leu Phe Pro Pro Lys Pro
             20                  25                  30
Lys Asp Thr Leu Met Ile Ser Arg Thr Pro Glu Val Thr Cys Val Val
         35                  40                  45
Val Asp Val Ser His Glu Asp Pro Glu Val Lys Phe Asn Trp Tyr Val
     50                  55                  60
Asp Gly Val Glu Val His Asn Val Lys Thr Lys Pro Arg Glu Glu Gln
 65                  70                  75                  80
Tyr Asn Ser Thr Tyr Arg Val Val Ser Val Leu Thr Val Leu His Gln
                 85                  90                  95
Asn Trp Met Asn Gly Lys Glu Tyr Lys Cys Lys Val Ser Asn Lys Ala
            100                 105                 110
Leu Pro Ala Pro Ile Glu Lys Thr Ile Ser Lys Ala Lys Val Gln Pro
        115                 120                 125
Arg Glu Pro Gln Val Tyr Thr Leu Pro Pro Ser Arg Asp Glu Leu Thr
    130                 135                 140
Lys Asn Gln Val Ser Leu Thr Cys Leu Val Lys Gly Phe Tyr Pro Ser
145                 150                 155                 160
Asp Ile Ala Val Glu Trp Glu Ser Asn Gly Gln Pro Glu Asn Asn Tyr
                165                 170                 175
Lys Thr Thr Pro Pro Val Leu Asp Ser Val Gly Ser Phe Phe Leu Tyr
            180                 185                 190
Ser Lys Leu Thr Val Asp Lys Ser Arg Trp Gln Gln Gly Asn Val Phe
        195                 200                 205
Ser Cys Ser Val Met His Glu Ala Leu His Asn His Tyr Gln Gln Arg
    210                 215                 220
Ser Leu Ser Leu Ser Pro Gly Lys Val Glu Gly Gly Gly Ser Gly
225                 230                 235                 240
Gly Gly Gly Ser Gly Gly Gly Ser Phe Thr Pro Thr Val Lys
                245                 250                 255
Ile Leu Gln Ser Ser Cys Asp Gly Gly Gly His Phe Pro Pro Thr Ile
            260                 265                 270
Gln Leu Leu Cys Leu Val Ser Gly Tyr Thr Pro Gly Thr Ile Asn Ile
        275                 280                 285
Thr Trp Leu Glu Asp Gly Gln Val Met Asp Val Asp Leu Ser Thr Ala
    290                 295                 300
Ser Thr Thr Gln Glu Gly Glu Leu Ala Ser Thr Gln Ser Glu Leu Thr
305                 310                 315                 320
Leu Ser Gln Lys His Trp Leu Ser Asp Arg Thr Tyr Thr Cys Gln Val
                325                 330                 335
Thr Tyr Gln Gly His Thr Phe Glu Asp Ser Thr Lys Lys Cys Ala Asp
            340                 345                 350
Ser Asn Pro Arg Gly Val Ser Ala Tyr Leu Ser Arg Pro Ser Pro Phe
        355                 360                 365
Asp Leu Phe Ile Arg Lys Ser Pro Thr Ile Thr Cys Leu Val Val Asp
    370                 375                 380
Leu Ala Pro Ser Lys Gly Thr Val Asn Leu Thr Trp Ser Arg Ala Ser
385                 390                 395                 400
Gly Lys Pro Val Asn His Ser Thr Arg Lys Glu Glu Lys Gln Arg Asn
```

```
                    405                 410                 415
Gly Thr Leu Thr Val Thr Ser Thr Leu Pro Val Gly Thr Arg Asp Trp
            420                 425                 430

Ile Glu Gly Glu Thr Tyr Gln Cys Arg Val Thr His Pro His Leu Pro
            435                 440                 445

Arg Ala Leu Met Arg Ser Thr Lys Thr Ser Gly Pro Arg Ala Ala
            450                 455                 460

Pro Glu Val Tyr Ala Phe Ala Thr Pro Glu Trp Pro Gly Ser Arg Asp
465                 470                 475                 480

Lys Arg Thr Leu Ala Cys Leu Ile Gln Asn Phe Met Pro Glu Asp Ile
                485                 490                 495

Ser Val Gln Trp Leu His Asn Glu Val Gln Leu Pro Asp Ala Arg His
                500                 505                 510

Ser Thr Thr Gln Pro Arg Lys Thr Lys Gly Ser Gly Phe Phe Val Phe
            515                 520                 525

Ser Arg Leu Glu Val Thr Arg Ala Glu Trp Glu Gln Lys Asp Glu Phe
            530                 535                 540

Ile Cys Arg Ala Val His Glu Ala Ala Ser Pro Ser Gln Thr Val Gln
545                 550                 555                 560

Arg Ala Val Ser Val Asn Pro Gly Lys
                565

<210> SEQ ID NO 8
<211> LENGTH: 73
<212> TYPE: DNA
<213> ORGANISM: Unknown
<220> FEATURE:
<223> OTHER INFORMATION: primer sequence

<400> SEQUENCE: 8
gctcgagggt ggaggcggtt caggcggagg tggctctggc ggtggcggat cgttcacccc    60
gcccaccgtg aag                                                      73

<210> SEQ ID NO 9
<211> LENGTH: 33
<212> TYPE: DNA
<213> ORGANISM: Unknown
<220> FEATURE:
<223> OTHER INFORMATION: primer sequence

<400> SEQUENCE: 9
ggcggccgct catttaccgg gatttacaga cac                                33

<210> SEQ ID NO 10
<211> LENGTH: 32
<212> TYPE: PRT
<213> ORGANISM: Arachis hypogaea (peanut)
<220> FEATURE:
<221> NAME/KEY: UNSURE
<222> LOCATION: 1, 4, 11, 12, 27, 30
<223> OTHER INFORMATION: Xaa = any amino acid

<400> SEQUENCE: 10

Xaa Gln Gln Xaa Glu Leu Gln Asp Leu Glu Xaa Xaa Gln Ser Gln Leu
1               5                   10                  15
```

```
Glu Asp Ala Asn Leu Arg Pro Arg Glu Gln Xaa Leu Met Xaa Lys Ile
            20                  25                  30
```

<210> SEQ ID NO 11
<211> LENGTH: 32
<212> TYPE: PRT
<213> ORGANISM: Arachis hypogaea (peanut)
<220> FEATURE:
<221> NAME/KEY: UNSURE
<222> LOCATION: 1, 4, 8, 10, 11, 12, 27, 30
<223> OTHER INFORMATION: Xaa = any amino acid

<400> SEQUENCE: 11

```
Xaa Gln Gln Xaa Glu Leu Gln Xaa Asp Xaa Xaa Xaa Gln Ser Gln Leu
 1               5                  10                  15

Glu Arg Ala Asp Leu Arg Pro Gly Glu Gln Xaa Leu Met Xaa Lys Ile
            20                  25                  30
```

<210> SEQ ID NO 12
<211> LENGTH: 171
<212> TYPE: PRT
<213> ORGANISM: Homo sapiens

<400> SEQUENCE: 12

```
Met Ala Ser Gln Lys Arg Pro Ser Gln Arg His Gly Ser Lys Tyr Leu
 1               5                  10                  15

Ala Thr Ala Ser Thr Met Asp His Ala Arg His Gly Phe Leu Pro Arg
            20                  25                  30

His Arg Asp Thr Gly Ile Leu Asp Ser Ile Gly Arg Phe Phe Gly Gly
        35                  40                  45

Asp Arg Gly Ala Pro Lys Arg Gly Ser Gly Lys Asp Ser His His Pro
    50                  55                  60

Ala Arg Thr Ala His Tyr Gly Ser Leu Pro Gln Lys Ser His Gly Arg
65                  70                  75                  80

Thr Gln Asp Glu Asn Pro Val Val His Phe Phe Lys Asn Ile Val Thr
                85                  90                  95

Pro Arg Thr Pro Pro Ser Gln Gly Lys Gly Arg Gly Leu Ser Leu
            100                 105                 110

Ser Arg Phe Ser Trp Gly Ala Glu Gly Gln Arg Pro Gly Phe Gly Tyr
        115                 120                 125

Gly Gly Arg Ala Ser Asp Tyr Lys Ser Ala His Lys Gly Phe Lys Gly
    130                 135                 140

Val Asp Ala Gln Gly Thr Leu Ser Lys Ile Phe Lys Leu Gly Gly Arg
145                 150                 155                 160

Asp Ser Arg Ser Gly Ser Pro Met Ala Arg Arg
                165                 170
```

<210> SEQ ID NO 13
<211> LENGTH: 17
<212> TYPE: PRT
<213> ORGANISM: Homo sapiens

<400> SEQUENCE: 13

```
Glu Asn Pro Val Val His Phe Phe Lys Asn Ile Val Thr Pro Arg Thr
 1               5                  10                  15

Pro
```

FUSION MOLECULES AND METHODS FOR TREATMENT OF IMMUNE DISEASES

This application is a divisional application of, and claims priority under 35 U.S.C. §120 to, U.S. patent application Ser. No. 10/000,439 filed Oct. 24, 2001, now U.S. Pat. No. 7,534, 440 which is a continuation-in-part application claiming priority under 35 U.S.C. §120 to U.S. patent application Ser. No. 09/847,208 filed May 1, 2001, now U.S. Pat. No. 7,265,208, which applications are hereby incorporated by reference in entirety their entireties.

This invention was made with Government support under Grant No. AI15251, awarded by the National Institutes of Health. The Government has certain rights in this invention.

BACKGROUND OF THE INVENTION

1. Field of the Invention

The invention concerns a new approach for the management of immune diseases using novel fusion polypeptides. More specifically, the invention is related to the treatment of immune diseases, where management of the disease comprises suppressing an inappropriate or unwanted immune response, such as, for example, autoimmune diseases and allergic diseases.

2. Description of the Related Art

Immunoglobulin Receptors

Immunoglobulin receptors (also referred to as Fc receptors) are cell-surface receptors binding the constant region of immunoglobulins, and mediate various immunoglobulin functions other than antigen binding.

Fc receptors for IgE molecules are found on many cell types of the immune system (Fridman, W., *FASEB J.*, 5(12): 2684-90 (1991)). There are two different receptors currently known for IgE. IgE mediates its biological responses as an antibody through the multichain high-affinity receptor, FcϵRI, and the low-affinity receptor, FcϵRII. The high-affinity FcϵRI, expressed on the surface of mast cells, basophils, and Langerhans cells, belongs to the immunoglobulin gene superfamily, and has a tetrameric structure composed of an α-chain, a β-chain and two disulfide-linked γ-chains (Adamczewski, M., and Kinet, J. P., *Chemical Immun.*, 59:173-190 (1994)) that are required for receptor expression and signal transduction (Tunon de Lara, *Rev. Mal. Respir.*, 13(1):27-36 (1996)). The α-chain of the receptor interacts with the distal portion of the third constant domain of the IgE heavy chain. The specific amino acids of human IgE involved in binding to human FcϵRI have been identified as including Arg-408, Ser-411, Lys-415, Glu-452, Arg-465, and Met-469 (Presta et al., *J. Biol. Chem.* 269:26368-73 (1994)). The interaction is highly specific with a binding constant of about $10^{10} M^{-1}$.

The low-affinity FcϵRII receptor, represented on the surface of inflammatory cells, including eosinophils, leukocytes, B lymphocytes, and platelets, did not evolve from the immunoglobulin superfamily but has substantial homology with several animal lectins (Yodoi et al., *Ciba Found. Symp.*, 147: 133-148 (1989)) and is made up of a transmembrane chain with an intracytoplasmic $NH_2$ terminus. The low-affinity receptor, FcϵRII (CD23) is currently known to have two forms (FcϵRIIa and FcϵRIIb), both of which have been cloned and sequenced. They differ only in the N-terminal cytoplasmic region, the extracellular domains being identical. FcϵRIIa is normally expressed on B cells, while FcϵRIIb is expressed on T cells, B cells, monocytes and eosinophils upon induction by the cytokine IL-4.

Through the high-affinity IgE receptor, FcϵRI, IgE plays key roles in an array of acute and chronic allergic reactions, including asthma, allergic rhinitis, atopic dermatitis, severe food allergies, chronic urticaria and angioedema, as well as the serious physiological condition of anaphylactic shock as results, for example, from bee stings or penicillin allergy. Binding of a multivalent antigen (allergen) to antigen-specific IgE specifically bound to FcϵRI on the surface of mast cells and basophils stimulates a complex series of signaling events that culminate in the release of host vasoactive and proinflammatory mediators contributing to both acute and late-phase allergic responses (Metcalfe et al., *Physiol. Rev.* 77:1033-1079 (1997)).

The function of the low affinity IgE receptor, FcϵRII (also referred to as CD23), found on the surface of B lymphocytes, is much less well established than that of FcϵRI. FcϵRII, in a polymeric state, binds IgE, and this binding may play a role in controlling the type (class) of antibody produced by B cells.

Three groups of receptors that bind the constant region of human IgG have so far been identified on cell surfaces: FcγRI (CD64), FcγRII (CD32), and FcγRIII (CD16), all of which belong to the immunoglobulin gene superfamily. The three Fcγ receptors have a large number of various isoforms.

Along with the stimulatory FcϵRI, mast cells and basophils co-express an immunoreceptor tyrosine-based inhibition motif (ITIM)-containing inhibitory low-affinity receptor, FcγRIIb, that acts as a negative regulator of antibody function. FcγRIIb represents a growing family of structurally and functionally similar inhibitory receptors, the inhibitory receptor superfamily (IRS), that negatively regulate immunoreceptor tyrosine-based activation motif (ITAM)-containing immune receptors (Ott and Cambier, *J. Allergy Clin. Immunol.*, 106:429-440 (2000)) and a diverse array of cellular responses. Coaggregation of an IRS member with an activating receptor leads to phosphorylation of the characteristic ITIM tyrosine and subsequent recruitment of the SH2 domain-containing protein tyrosine phosphatases, SHP-1 and SHP-2, and the SH2 domain-containing phospholipases, SHIP and SHIP2 (Cambier, J. C., *Proc. Nat. Acad. Sci. USA*, 94:5993-5995 (1997)). Possible outcomes of the coaggregation include inhibition of cellular activation, as demonstrated by the coaggregation of FcγRIIb and B-cell receptors, T-cell receptors, activating receptors, including FcϵRI, or cytokine receptors (Malbec et al., *Curr. Top. Microbiol. Immunol.*, 244:13-27 (1999)).

Most studies have so far concentrated on elucidating the mechanisms of FcγRII, in particular, FcγRIIb function. The three alternatively spliced isoforms of the FcγIIb receptor, of which FcγRIIb1 is only found in mice, and FcγRIIb1 and FcγRIIb2 are expressed in both humans and mice, have Ig-like loops and a conserved ITIM, but differ in their cytoplasmic domains. Co-crosslinking of the high-affinity FcϵRI receptor and the inhibitory low-affinity receptor FcγRII blocks a number of processes, including FcϵRI-mediated secretion, IL-4 production, $Ca^{2+}$ mobilization, Syk phosphorylation, and FcϵRI-mediated basophil and mast cell activation. In B cells, co-crosslinking of the B-cell receptor and FcγRIIb inhibits B-cell receptor-mediated cell activation (Cambier, J. C., *Proc. Natl. Acad. Sci.*, 94:5993-5995 (1997); Daeron, M., *Annu. Rev. Immunol*, 15:203-234 (1997)), and specifically, inhibits B-cell receptor-induced blastogenesis and proliferation (Chan et al., *Immunology*, 21:967-981 (1971); Phillips and Parker, *J. Immunol.*, 132:627-632 (1984)) and stimulates apoptosis (Ashman et al., *J. Immunol,* 157:5-11 (1996)). Coaggregation of FcγRIIb1 or FcγRIIb2 with FcγRI in rat basophilic leukemia cells, inhibits FcϵRI-mediated release of serotonin and TNF-α (Daeron et al., *J. Clin. Invest.*, 95:577-85 (1995); Daeron et al., *Immunity*, 3:635-646 (1995)).

Another ITIM-containing receptor expressed on mast cells that has been described to prevent IgE-mediated mast cell activation when coligated with FcεRI, is a 49 kDa glycoprotein member of the immunoglobulin superfamily, termed gp49b1 (gp91) (see, e.g., Wagtmann et al., *Current Top. Micobiol. Immunol.* 244:107-113 (1999); Katz, H. R., *Int. Arch Allergy Immunol.* 118:177-179 (1999); and Lu-Kuo et al., *J. Biol. Chem.* 274:5791-96 (1999)). Gp49b1 was originally identified in mice, while human counterparts of the gp49 family, including gp49b1, have been cloned by Arm et al., *J. Immunol.* 15:2342-2349 (1997). Further ITIM-containing receptors, several expressed in mast cells, basophils or B cells are reviewed by Sinclair N R, *Scand. J. Immunol.*, 50:10-13 (1999).

Through the high-affinity IgE receptor FcεRI, IgE plays key roles in immune response. The activation of mast cells and basophils by antigen (i.e., allergen) via an antigen-specific IgE/FcεRI pathway results in the release of host vasoactive and proinflammatory mediators (i.e., degranulation), which contributes to the allergic response (Oliver et al., *Immunopharmacology* 48:269-281 [2000]; Metcalfe et al., *Physiol. Rev.,* 77:1033-1079 [1997]). These and other biochemical events lead to the rapid secretion of inflammatory mediators such as histamine, resulting in physiological responses that include localized tissue inflammation, vasodilation, increased blood vessel and mucosal permeability, and local recruitment of other immune system cells, including additional basophils and mast cells. In moderation, these responses have a beneficial role in immunity against parasites and other microorganisms. However, when in excess, this physiological response results in the varied pathological conditions of allergy, also known as type I hypersensitivity.

Allergic Conditions

Allergy is manifested in a broad array of conditions and associated symptoms, which may be mild, chronic, acute and/or life threatening. These various pathologies include, for example, allergic asthma, allergic rhinitis, atopic dermatitis, severe food allergies, chronic urticaria and angioedema, as well as the serious physiological condition of anaphylactic shock. A wide variety of antigens are known to act as allergens, and exposure to these allergens results in the allergic pathology. Common allergens include, but are not limited to, bee stings, penicillin, various food allergies, pollens, animal detritus (especially house dust mite, cat, dog and cockroach), and fungal allergens. The most severe responses to allergens can result in airway constriction and anaphylactic shock, both of which are potentially fatal conditions. Despite advances in understanding the cellular and molecular mechanisms that control allergic responses and improved therapies, the incidence of allergic diseases, especially allergic asthma, has increased dramatically in recent years in both developed and developing countries (Beasley et al., *J. Allergy Clin. Immunol.* 105:466-472 (2000); Peat and Li, *J. Allergy Clin. Immunol.* 103:1-10 (1999)). Thus, there exists a strong need to develop treatments for allergic diseases.

Allergic asthma is a condition brought about by exposure to ubiquitous, environmental allergens, resulting in an inflammatory response and constriction of the upper airway in hypersensitive individuals. Mild asthma can usually be controlled in most patients by relatively low doses of inhaled corticosteroids, while moderate asthma is usually managed by the additional administration of inhaled long-acting β-antagonists or leukotriene inhibitors. The treatment of severe asthma is still a serious medical problem. In addition, many of the therapeutics currently used in allergy treatment have serious side-effects. Although an anti-IgE antibody currently in clinical trials (rhuMAb-E25, Genentech, Inc.) and other experimental therapies (e.g., antagonists of IL-4) show promising results, there is need for the development of additional therapeutic strategies and agents to control allergic disease, such as asthma, severe food allergy, and chronic urticaria and angioedema.

One approach to the treatment of allergic diseases is by use of allergen-based immunotherapy. This methodology uses whole antigens as "allergy vaccines" and is now appreciated to induce a state of relative allergic tolerance. This technique for the treatment of allergy is frequently termed "desensitization" or "hyposensitization" therapy. In this technique, increasing doses of allergen are administered, typically by injection, to a subject over an extended period of time, frequently months or years. The mechanism of action of this therapy is thought to involve induction of IgG inhibitory antibodies, suppression of mast cell/basophil reactivity, suppression of T-cell responses, the promotion of T-cell anergy, and/or clonal deletion, and in the long term, decrease in the levels of allergen specific IgE. The use of this approach is, however, hindered in many instances by poor efficacy and serious side-effects, including the risk of triggering a systemic and potentially fatal anaphylactic response, where the clinical administration of the allergen induces the severe allergic response it seeks to suppress (TePas et al., *Curr. Opin. Pediatrics* 12:574-578 [2000]).

Refinements of this technique use smaller portions of the allergen molecule, where the small portions (i.e., peptides) presumably contain the immunodominant epitope(s) for T cells regulating the allergic reaction. Immunotolerance therapy using these allergenic portions is also termed peptide therapy, in which increasing doses of allergenic peptide are administered, typically by injection, to a subject. The mechanism of action of this therapy is thought to involve suppression of T-cell responses, the promotion of T-cell anergy, and/or clonal deletion. Since the peptides are designed to bind only to T cells and not to allergic (IgE) antibodies, it was hoped that the use of this approach would not induce allergic reactions to the treatment. Unfortunately, these peptide therapy trials have met with disappointment, and allergic reactions are often observed in response to the treatments. Development of these peptide therapy methods have largely been discontinued.

Autoimmune Diseases

It is estimated that as much as 20 percent of the American population has some type of autoimmune disease. Autoimmune diseases demonstrate disproportionate expression in women, where it is estimated that as many as 75% of those affected with autoimmune disorders are women. Although some forms of autoimmune diseases are individually rare, some diseases, such as rheumatoid arthritis and autoimmune thyroiditis, account for significant morbidity in the population (Rose and MacKay (Eds.), *The Autoimmune Diseases*, Third Edition, Academic Press [1998]).

Autoimmune disease results from failure of the body to eliminate self-reactive T-cells and B-cells from the immune repertoire, resulting in circulating B-cell products (i.e., autoreactive antibodies) and T-cells that are capable of identifying and inducing an immune response to molecules native to the subject's own physiology. Particular autoimmune disorders can be generally classified as organ-specific (i.e., cell-type specific) or systemic (i.e., non-organ specific), but with some diseases showing aspects of both ends of this continuum. Organ-specific disorders include, for example, Hashimoto's thyroiditis (thyroid gland) and insulin dependent diabetes mellitus (pancreas). Examples of systemic disorders include rheumatoid arthritis and systemic lupus erythematosus. Since an autoimmune response can potentially be generated against any organ or tissue in the body, the autoimmune diseases display a legion of signs and symptoms. Furthermore, when blood vessels are a target of the autoimmune attack as in the autoimmune vasculitides, all organs may be involved. Autoimmune diseases display a wide variety of severity varying from mild to life-threatening, and from acute to chronic, and relapsing (Rose and MacKay (Eds.), *The Autoimmune Diseases*, Third Edition, Academic Press [1998]; and Davidson and Diamond, *N. Engl. J. Med.*, 345 (5):340-350 [2001]).

The molecular identity of some of the self-reactive antigens (i.e., the autoantigen) are known in some, but not all, autoimmune diseases. The diagnosis and study of autoimmune diseases is complicated by the promiscuous nature of these disorders, where a patient with an autoimmune disease can have multiple types of autoreactive antibodies, and vice versa, a single type of autoreactive antibody is sometimes observed in multiple autoimmune disease states (Nocci et al., *Curr. Opin. Immunol.*, 12:725-730 [2000]; and Davidson and Diamond, *N. Engl. J. Med.*, 345(5):340-350 [2001]). Furthermore, autoreactive antibodies or T-cells may be present in an individual, but that individual will not show any indication of disease or other pathology. Thus while the molecular identity of many autoantigens is known, the exact pathogenic role of these autoantigens generally remains obscure (with notable exceptions, for example, myesthenia gravis, autoimmune thyroid disease, multiple sclerosis and diabetes mellitus).

Treatments for autoimmune diseases exist, but each method has its own particular drawbacks. Existing treatments for autoimmune disorders can be generally placed in two groups. First, and of most immediate importance, are treatments to compensate for a physiological deficiency, typically by the replacement of a hormone or other product that is absent in the patient. For example, autoimmune diabetes mellitus can be treated by the administration of insulin, while autoimmune thyroid disease is treated by giving thyroid hormone. Treatments of other disorders entails the replacement of various blood components, such as platelets in immune thrombocytopenia or use of drugs (e.g., erythropoetin) to stimulate the production of red blood cells in immune based anemia. In some cases, tissue grafts or mechanical substitutes offer possible treatment options, such as in lupus nephritis and chronic rheumatoid arthritis. Unfortunately, these types of treatments are suboptimal, as they merely alleviate the disease symptoms, and do not correct the underlying autoimmune pathology and the development of various disease related complications. Since the underlying autoimmune activity is still present, affected tissues, tissue grafts, or replacement proteins are likely to succumb to the same immune degeneration.

The second category of autoimmune disease treatments are those therapies that result in generalized suppression of the inflammatory and immune response. This approach is difficult at best, as it necessitates a balance between suppressing the disease-causing immune reaction, yet preserving the body's ability to fight infection. The drugs most commonly used in conventional anti-inflammatory therapy to treat autoimmune disorders are the non-steroidal anti-inflammatory drugs (e.g., aspirin, ibuprofen, etc). Unfortunately, these drugs simply relieve the inflammation and associated pain and other symptoms, but do not modify progression of the disease. Broad acting immunosuppressants, such as cyclosporine A, azathioprine, cyclophosphamide, and methotrexate, are commonly used to treat symptoms as well as hopefully ameliorate the course of the autoimmune process. Although somewhat successful in controlling the autoimmune tissue injury, these broad acting and powerful drugs often have severe side effects, such as the development of neoplasias, destruction of bone marrow and other rapidly dividing cells and tissues, and risk of liver and kidney injury. Furthermore, these drugs have the undesirable consequence of depressing the patient's immune system, which carries the risk of severe infectious complications. For these reasons, general suppression of the immune system is generally reserved for the treatment of severe autoimmune disorders, such as dermatomyositis and systemic lupus erythematosus (SLE) or when there is involvement of a critical organ, such as the heart.

More preferably, successful immuno-suppressive therapies for autoimmune disorders will suppress the immune system in an autoantigen-specific manner (i.e., antigen-restricted tolerance), similar to that proposed for allergen immunotolerance therapy to induce desensitization (Harrison and Hafler, *Curr. Opin. Immunol.*, 12:704-711 [2000]; Weiner, *Annu. Rev. Med.*, 48:341-351 [1997]; and Mocci et al., *Curr. Opin. Immunol.*, 12:725-730 [2000]). Refinements of this approach have used smaller portions of the autoantigen (i.e., autoantigenic peptides) which contain the immunodominant epitope(s), using oral and parenteral administration protocols. Like allergy peptide therapies, administration of autoantigen peptides is now recognized to be accompanied by significant risk of allergic/hypersensitivity reactions and potentially fatal anaphylactic response. These risks also limit the amount of peptide that can be administered in a single dose. For these and other reasons, peptide immunotolerance therapies for the treatment of autoimmune diseases in humans have been problematic, and many have failed to find widespread applicability. These tolerance therapies remain largely unusable, unless the risk of allergic reactions can be overcome.

Autoimmune type-I diabetes mellitus is a form of insulin-dependent diabetes resulting from immune recognition of insulin or those cells that produce insulin, i.e., the pancreatic islet β-cells, leading to immune-mediated destruction of the β-cells, and reduction of insulin production or activity. The disease is thought to be initiated by multiple etiologies, but all resulting in insulin deficiency. The known autoantigen targets of autoimmune diabetes include insulin and glutamic acid decarboxylase (GAD) (Chaillous et al., *Diabetologia* 37(5): 491-499 [1994]; Naquet et al., *J. Immunol.*, 140(8):2569-2578 [1988]; Yoon et al., *Science* 284(5417):1183-1187 [1999]; Nepom et al., *Proc. Natl. Acad. Sci. USA* 98(4):1763-1768 [2001]). In addition to insulin and GAD, additional β-cell autoantigens are theorized to exist (Nepom, *Curr. Opin. Immunol.*, 7(6):825-830 [1995]).

Tolerance therapies incorporating either parenterally and orally administered diabetes autoantigens (including insulin and GAD) have been tried in experimental models and human subjects. However, the majority of human trials have met with disappointment. Furthermore, widespread application of peptide therapy in humans to treat autoimmune diabetes has been prevented by the observation that in some cases, peptide administration may actually accelerate disease progression (Pozzilli et al., *Diabetologia* 43:1000-1004 [2000]; Gale, *Lancet* 356(9229):526-527 [2000]; Chaillous et al., *Lancet* 356:545-549 [2000]; Blanas et al., *Science* 274:1707-1709 [1996]; McFarland, *Science* 274(5295):2037 [1996]; and Bellmann et al., *Diabetologia* 41:844-887 [1998]).

Rheumatoid arthritis (RA) is another severe autoimmune disorder that impacts a significant percentage of the population. RA is a systemic disease characterized by chronic inflammation primarily of the synovial membrane lining of the joints, although the disease can effect a host of other tissues, such as the lung. This joint inflammation leads to chronic pain, loss of function, and ultimately to destruction of the joint. The presence of T-cells in the synovia, as well as other lines of evidence, indicate an autoimmune disease etiology. A number of autoantigen candidates for this disease have been tentatively identified, including type II collagen, human cartilage protein gp39 and gp130-RAPS. Existing treatment regimens for RA include anti-inflammatory drugs (both steroidal and non-steroidal), cytotoxic therapy (e.g., cyclosporine A, methotrexate and leflunomide), and biological immune modulators such as interleukins-1 and -2 receptor antagonists, anti-tumor necrosis factor alpha (TNFα) monoclonal antibodies, and TNFα receptor-IgG1 fusion proteins, frequently in conjunction with methotrexate (Davidson and Diamond, $N.$ $Engl.$ $J.$ $Med.,$ 345(5):340-350 [2001]). However, these biological modifier therapies are suboptimal for a variety of reasons, notably do to their limited effectiveness and toxicity such as the systemic cytokine release syndrome seen with administration of a number of cytokines (e.g., IL-2), or the recently recognized increased risk of infection with anti-TNFα treatments.

In T-cells isolated from patients with this disease, it has been observed that some T-cell receptor (TCR) β-subunit variable domains ($V_β$) appear to be preferentially utilized compared to disease-free subjects. It is suggested that peptides corresponding to these preferentially utilized TCR $V_β$ domains can be used in peptide vaccination therapy, where vaccination will result in disease-specific anti-TCR antibodies, and hopefully alleviate the disease (Bridges and Moreland, $Rheum.$ $Dis.$ $Clin.$ $North$ $Am.,$ 24(3):641-650 [1998]; and Gold et al., $Crit.$ $Rev.$ $Immunol.,$ 17 (5-6):507-510 [1997]). This therapy is under development (Moreland et al., $J.$ $Rheumatol.,$ 23(8):1353-1362 [1996]; and Moreland et al., $Arthritis$ $Rheum.,$ 41(11):1919-1929 [1998]), but has proven to be problematic due to the lack of consistency in TCR use in humans as opposed to what was observed in experimental animals.

A proposed alternative to antibody-based therapies for rheumatoid arthritis and other autoimmune diseases are therapies that incorporate major histocompatibility complex class II proteins (MHC II) covalently coupled with autoreactive peptides (Sharma et al., $Proc.$ $Natl.$ $Acad.$ $Sci.$ $USA$ 88:11465-11469 [1991]; and Spack et al., $Autoimmunity$ 8:787-807 [1995]). A variation of this MHC-based therapy incorporates covalently coupled $F_cγ$ domains for the purpose of producing dimeric MHC/antigen fusion polypeptides (Casares et al., $Protein$ $Eng.,$ 10(11):1295-1301 [1997]; and Casares et al., $J.$ $Exp.$ $Med.,$ 190(4):543-553 [1999]). However, these approaches based on artificial antigen presentation in the context of an MHC II fusion protein are unlikely to be widely applicable in human systems, as the MHC loci in humans are multiallelic (i.e., there exist many haplotype variations).

Another autoimmune disorder impacting a significant portion of the population is multiple sclerosis (MS), which afflicts approximately 250,000 people in the United States alone. MS manifests mainly in adults, and displays a wide array of neurological-related symptoms that vary unpredictably over decades, and may relapse, progress, or undergo spontaneous remission. No therapies currently exist that can arrest the progression of the primary neurologic disability caused by MS. Current therapies favor the use of glucocorticosteroids, but unfortunately corticosteroid therapies are not believed to alter the long-term course of the disease. Furthermore, corticosteroids have many side effects, including increased risk of infection, osteoporosis, gastric bleeding, cataracts and hypertension. Immunosuppressants are sometimes tried in progressive MS, but with equivocal results.

Biological immune modulators, such as interferons α and β1a, and copolymer I, have also been tried in an attempt to downregulate the immune response and control the progression of the disease. Administration of interferon-β to suppress general immune function in patients with multiple sclerosis has had some limited success (Rose and MacKay (Eds.), $The$ $Autoimmune$ $Diseases,$ Third Edition, Academic Press, p. 572-578 [1998]; Davidson and Diamond, $N.$ $Engl.$ $J.$ $Med.,$ 345(5):340-350 [2001]). However, these biological modifiers have the drawback of limited efficacy and systemic side effects of fever and flu-like reactions.

The varied neurological-related symptoms of MS are the result of degeneration of the myelin sheath surrounding neurons within the central nervous system (CNS), as well as loss of cells that deposit and support the myelin sheaths, i.e., the oligodendrocytes, with ensuing damage to the underlying axons. T-cells isolated from patients with MS respond to myelin-basic-protein (MBP) by proliferating and secreting proinflammatory cytokines, indicating that endogenous MBP is at least one of the autoantigens being recognized in patients with the disease. The immunodominant epitope on the MBP protein has been shown to reside within the $MBP_{83-99}$ region. As is the case in many autoimmune diseases, at least one other autoantibody has been implicated as the causative agent in patients with multiple sclerosis. This autoantibody appears to be specific for myelin oligodendrocyte glycoprotein (MOG), with a dominant epitope at $MOG_{92-106}$.

Peptide immunotherapies using the MBP epitope to treat MS have been tested in animal models and in humans (e.g., Weiner et al., $Science$ 259(5099):1321-1324 [1993]; Warren et al., $Jour.$ $Neuro.$ $Sci.,$ 152:31-38 [1997]; Goodkin et al., $Neurology$ 54:1414-1420 [2000]; Kappos et al., $Nat.$ $Med.,$ 6(10):1176-1182 [2000]; Bielekova et al., $Nat.$ $Med.,$ 6(10): 1167-1175 [2000]; and Steinman and Conlon, $Jour.$ $Clin.$ $Immunol.,$ 21(2):93-98 [2001]). Unfortunately, those studies using human subjects have been disappointing, with significant toxicity and hypersensitivity reactions reported. Furthermore, multiple sclerosis autoantigen immunotherapy may actually exacerbate the disease in some cases (McFarland, $Science$ 274(5295):2037 [1996]; and Genain et al., $Science$ 274:2054-2057 [1996]).

What is needed are improved and/or novel therapeutic strategies for the treatment of immune diseases resulting from inappropriate or unwanted immune response. What are needed are methods for the treatment of autoimmune diseases that are widely applicable to many autoimmune diseases, do not have the toxic effects of broad immunosuppressant drugs, and act in an autoantigen-restricted manner, thereby preserving a patient's immune function. Accordingly, there is a need for improved methods for peptide tolerance immunotherapies that have reduced risk of hypersensitivity reactions, and most notably, anaphylactic responses. Similarly, there is a need for compositions and methods that permit higher dosages of traditional peptide tolerance therapies, without the risk of inducing hypersensitivity responses.

The object of this invention is to provide novel and/or improved therapeutic strategies for the treatment of immune diseases resulting from inappropriate or unwanted immune response. Allergic diseases and autoimmune diseases are two such types of diseases which can be treated with the compositions and methods provided by the present invention. Allergic diseases which may be treated using the invention include, but are not limited to, for example, atopic allergies such as asthma, allergic rhinitis, atopic dermatitis, severe food allergies, some forms of chronic urticaria and angioedema, as well as the serious physiological condition of anaphylactic shock (i.e., anaphylactic hypersensitivity) resulting from, for example, bee stings or penicillin allergy. Autoimmune diseases which can be treated using the present invention include, but are not limited to, autoimmune diabetes, rheumatoid arthritis, and multiple sclerosis, for example.

The methods for treating allergic and autoimmune diseases provided by the invention can also be used in conjunction with traditional peptide immunotherapies, where the fusion molecules described herein are administered before, during or after the peptide immunotherapy, and find particular use in preventing the anaphylactic reactions associated with traditional immunotherapies.

SUMMARY OF THE INVENTION

The present invention provides novel multi-functional compounds that have the ability to crosslink inhibitory receptors with Fcε receptors and block Fcε receptor-mediated biological activities, as well as methods for using such compounds, and compositions and articles of manufacture comprising them. The invention also provides compositions and methods suitable for the prevention or treatment of immune-mediated diseases.

One aspect the invention concerns an isolated fusion molecule comprising a first polypeptide sequence capable of specific binding, to a native inhibitory receptor comprising an immune receptor tyrosine-based inhibitory motif (ITIM), functionally connected to a second polypeptide sequence capable of specific binding, through a third polypeptide sequence, to a native IgE receptor (FcεR), wherein the first and second polypeptide sequences are other than antibody variable regions, and wherein said fusion molecule is not capable of T cell interaction prior to internalization. Preferably, the second polypeptide sequence comprises an antigen sequence, and more preferably, at least a portion of an autoantigen sequence. In one embodiment, the autoantigen sequence comprises at least one autoantigenic epitope. In one preferred embodiment, the third polypeptide is an immunoglobulin specific for the autoantigen. In a particularly preferred embodiment, the immunoglobulin specific for the autoantigen is an IgE class antibody.

In some preferred embodiments, the autoantigen sequence in the fusion molecule is selected from the group consisting of rheumatoid arthritis autoantigen, multiple sclerosis autoantigen, or autoimmune type I diabetes mellitus autoantigen, and portions thereof. In other preferred embodiments, the autoantigen is selected from the group consisting of myelin basic protein (MBP), proteolipid protein, myelin oligodendrocyte glycoprotein, αβ-crystallin, myelin-associated glycoprotein, Po glycoprotein, PMP22, 2',3'-cyclic nucleotide 3'-phosphohydrolase (CNPase), glutamic acid decarboxylase (GAD), insulin, 64 kD islet cell antigen (IA-2, also termed ICA512), phogrin (IA-2β), type II collagen, human cartilage gp39 (flCgp39), and gp130-RAPS, and portions thereof.

In other preferred embodiments, the autoantigen sequence in the fusion molecule comprises at least 90% sequence identity with at least a portion of an autoantigen sequence. In still other preferred embodiments, the autoantigen sequence in the fusion molecule comprises an amino acid sequence encoded by a nucleic acid hybridizing under stringent conditions to at least a portion of the complement of a nucleic acid molecule encoding an autoantigen.

In a particularly preferred embodiments, the inhibitory receptor is a type I transmembrane molecule with an Ig-like domain, such as, for example, a low-affinity FcγRIIb IgG receptor, and the IgE receptor may be a FcεRI high-affinity receptor or a low-affinity FcεRII receptor (CD23). More preferably, the FcγRIIb and FcεRI receptors are of human origin.

In a related embodiment, the first polypeptide sequence comprises an amino acid sequence having at least 85% identity with a native human IgG heavy chain constant region sequence. Indeed, the IgG portion of the molecule can derive from the heavy chain constant region of any IgG subclass, including $IgG_1$, $IgG_2$, $IgG_3$ and $IgG_4$. Furthermore, the native human IgG heavy chain constant region sequence can be the native human IgG heavy chain constant region sequence of SEQ ID NO: 2.

In another embodiment, the first polypeptide sequence comprises preferably an amino acid sequence having at least 85% identity to the hinge-CH2-CH3 domain amino acid sequence of SEQ ID NO: 3, and more preferably, at least 90% identity, and more preferably still, at least 95% identity, and most preferably, at least 98% identity. In still other embodiments, the first polypeptide comprises a least part of the CH2 and CH3 domains of a native human $IgG_1$ constant region, or additionally comprises a least part of the hinge of a native human $IgG_1$ constant region. Alternatively, the first polypeptide sequence comprises at least part of the hinge, CH2 and CH3 domains of a native human $IgG_1$ heavy chain constant region in the absence of a functional CH1 region, and alternatively still, the first polypeptide sequence comprises an amino acid sequence encoded by a nucleic acid hybridizing under stringent conditions to at least a portion of the complement of the IgG heavy chain constant region nucleotide sequence of SEQ ID NO: 1.

In some embodiments, the first and second polypeptide sequences may be functionally connected via a linker, e.g., a polypeptide linker. The length of the polypeptide linker typically is about 5 to 25 amino acid residues. In one embodiment, the polypeptide linker comprises at least one proteasome proteolysis signal, wherein the signal is selected from the group consisting of large hydrophobic amino acid residues, basic amino acid residues and acidic amino acid residues. In other embodiments, the polypeptide linker sequence comprises at least one endopeptidase recognition motif. In other embodiments, the polypeptide linker sequence comprises a plurality of endopeptidase recognition motifs, and these endopeptidase motifs may include cysteine, aspartate or asparagine amino acid residues. In other embodiments, the fusion molecule comprises at least one amino-terminal ubiquitination target motif. In still other embodiments, the fusion molecule can display at least one proteasome proteolysis signal, wherein that signal is selected from the group consisting of large hydrophobic amino acid residues, basic amino acid residues or acidic amino acid residues.

In a further aspect, the present invention provides isolated nucleic acid molecules encoding a fusion molecule comprising a first polypeptide sequence capable of specific binding, to a native inhibitory receptor comprising an immune receptor tyrosine-based inhibitory motif (ITIM), functionally connected to a second polypeptide sequence that is an autoantigen sequence capable of specific binding, through a third polypeptide sequence, to a native IgE receptor (FcεR), wherein the first and second polypeptide sequences are other than antibody variable regions, and wherein said fusion molecule is not capable of T cell interaction prior to internalization. The invention also provides vectors and host cells comprising these nucleic acids. Similarly, the present invention provides isolated nucleic acid molecules as described above, wherein the second polypeptide sequence in the fusion molecule encodes at least a portion of an autoantigen. Vectors and host cells comprising these nucleic acids are also encompassed by the present invention.

In a further aspect, the invention concerns a pharmaceutical composition comprising a fusion molecule as hereinabove defined in admixture with a pharmaceutically acceptable excipient or ingredient. In a still further aspect, the invention concerns an article of manufacture comprising a container, a fusion molecule as hereinabove defined within the container, and a label or package insert on or associated with the container. The label or package insert preferably comprises instructions for the treatment or prevention of an immune disease.

In a further aspect, the present invention concerns methods for the treatment and prevention of immune-mediated diseases, where the subject is administered a fusion polypeptide as described herein. In one embodiment, the invention concerns a method for the treatment of an autoimmune disease, comprising administering at least once, or alternatively multiple times, an effective amount of at least one fusion molecule as hereinabove defined to a subject diagnosed with or at risk of developing an autoimmune disease. The subject preferably is a human. The autoimmune disease to be treated or prevented is not limited, but in some embodiments, is preferably selected from rheumatoid arthritis, type-I diabetes mellitus and multiple sclerosis. The fusion molecule as hereinabove defined and used in these treatment methods preferably contain an autoantigens selected from the group consisting of rheumatoid arthritis autoantigen, multiple sclerosis autoantigen, autoimmune type I diabetes mellitus autoantigen, and portions thereof. More specifically by name, examples of autoantigens finding use in the fusion molecule as hereinabove defined include myelin basic protein (MBP), proteolipid protein, myelin oligodendrocyte glycoprotein, αβ-crystallin, myelin-associated glycoprotein, Po glycoprotein, PMP22, 2',3'-cyclic nucleotide 3'-phosphohydrolase (CNPase), glutamic acid decarboxylase (GAD), insulin, 64 kD islet cell antigen (IA-2, also termed ICA512), phogrin (IA-2β), type II collagen, human cartilage gp39 (HCgp39), and gp130-RAPS.

In another aspect, the invention provides a method for the prevention of symptoms resulting from a type I hypersensitivity reaction in a subject receiving immunotherapy, comprising administering at least one fusion molecule to the subject, wherein the fusion molecule comprises a first polypeptide sequence capable of specific binding to a native IgG inhibitory receptor comprising an immune receptor tyrosine-based inhibitory motif (ITIM), functionally connected to a second polypeptide sequence capable of binding directly, or indirectly through a third polypeptide sequence, to a native IgE receptor (FcεR), wherein the first and second polypeptide sequences are other than antibody variable regions, and wherein said fusion molecule is not capable of T cell interaction prior to internalization. The second polypeptide sequence in this fusion molecule comprises, alternatively, (a) at least a portion of an autoantigen, (b) an allergen, or (c) at least a portion of an IgE immunoglobulin heavy chain constant region capable of binding to a native IgE receptor (FcεR). In a preferred embodiment, the type I hypersensitivity reaction is an anaphylactic response. In preferred embodiments of this method, the type I hypersensitivity symptoms being prevented comprise an anaphylactic response. In other embodiments, the first polypeptide comprises at least a portion of an IgG immunoglobulin heavy chain constant region, and the third polypeptide is an IgE class antibody.

In one aspect of this method of the invention, the immunotherapy received by the subject is for the treatment of type I hypersensitivity-mediated disease or autoimmune disease. In various embodiments of this method, the fusion molecule is administered to the subject prior to the subject receiving immunotherapy, co-administered to the subject during immunotherapy, or administered to the subject after the subject receives the immunotherapy.

In yet another aspect, the invention provides a method for the prevention of a type I hypersensitivity disease in a subject receiving immunotherapy, comprising administering at least one fusion molecule to the subject, wherein the fusion molecule comprises a first polypeptide sequence capable of specific binding to a native IgG inhibitory receptor comprising an immune receptor tyrosine-based inhibitory motif (ITIM), functionally connected to a second polypeptide sequence capable of binding directly, or indirectly through a third polypeptide sequence, to a native IgE receptor (FcεR), wherein the first and second polypeptide sequences are other than antibody variable regions, and wherein said fusion molecule is not capable of T cell interaction prior to internalization. The second polypeptide sequence in this fusion molecule comprises, alternatively, (a) at least a portion of an autoantigen, (b) an allergen, or (c) at least a portion of an IgE immunoglobulin heavy chain constant region capable of binding to a native IgE receptor (FcεR).

BRIEF DESCRIPTION OF THE FIGURES

FIG. 1 shows the nucleotide sequence encoding the human IgG$_1$ heavy chain constant region (SEQ ID NO: 1).

FIG. 2 shows the amino acid sequence of the human IgG$_1$ heavy chain constant region (SEQ ID NO: 2). In the sequence, the CH1 domain extends from amino acid position 122 to amino acid position 219, the hinge region extends from amino acid position 220 to amino acid position 231, the CH2 domain extends from amino acid position 232 to amino acid position 344, and the CH3 domain extends from amino acid position 345 to amino acid 451 (the C-terminus).

FIG. 3 shows the amino acid sequence of the hinge-CH2-CH3 portion of the human IgG$_1$ heavy chain constant region (SEQ ID NO: 3).

FIG. 4 shows the nucleotide sequence encoding the human IgE heavy chain constant region (SEQ ID NO: 4).

FIG. 5 shows the amino acid sequence of the human IgE heavy chain constant region (SEQ ID NO: 5).

FIG. 6 shows the amino acid sequence of the CH2-CH3-CH4 portion of the human IgE heavy chain constant region (SEQ ID NO: 6).

FIG. 7 shows the amino acid sequence of the γhinge-CHγ2-CHγ3-(Gly$_4$Ser)$_3$-CHε2-CHε3-CHε3 fusion molecule (GE2) of the invention (SEQ ID NO: 7).

FIG. 10 illustrates GE2 binding to HMC-1 cells that express FcγRIIb but not FcεRIa.

FIG. 11 illustrates GE2 binding to 3D10 cells that express FcεRIa but not FcγRIIb.

DETAILED DESCRIPTION OF THE PREFERRED EMBODIMENT

I. Definitions

Figure 8:
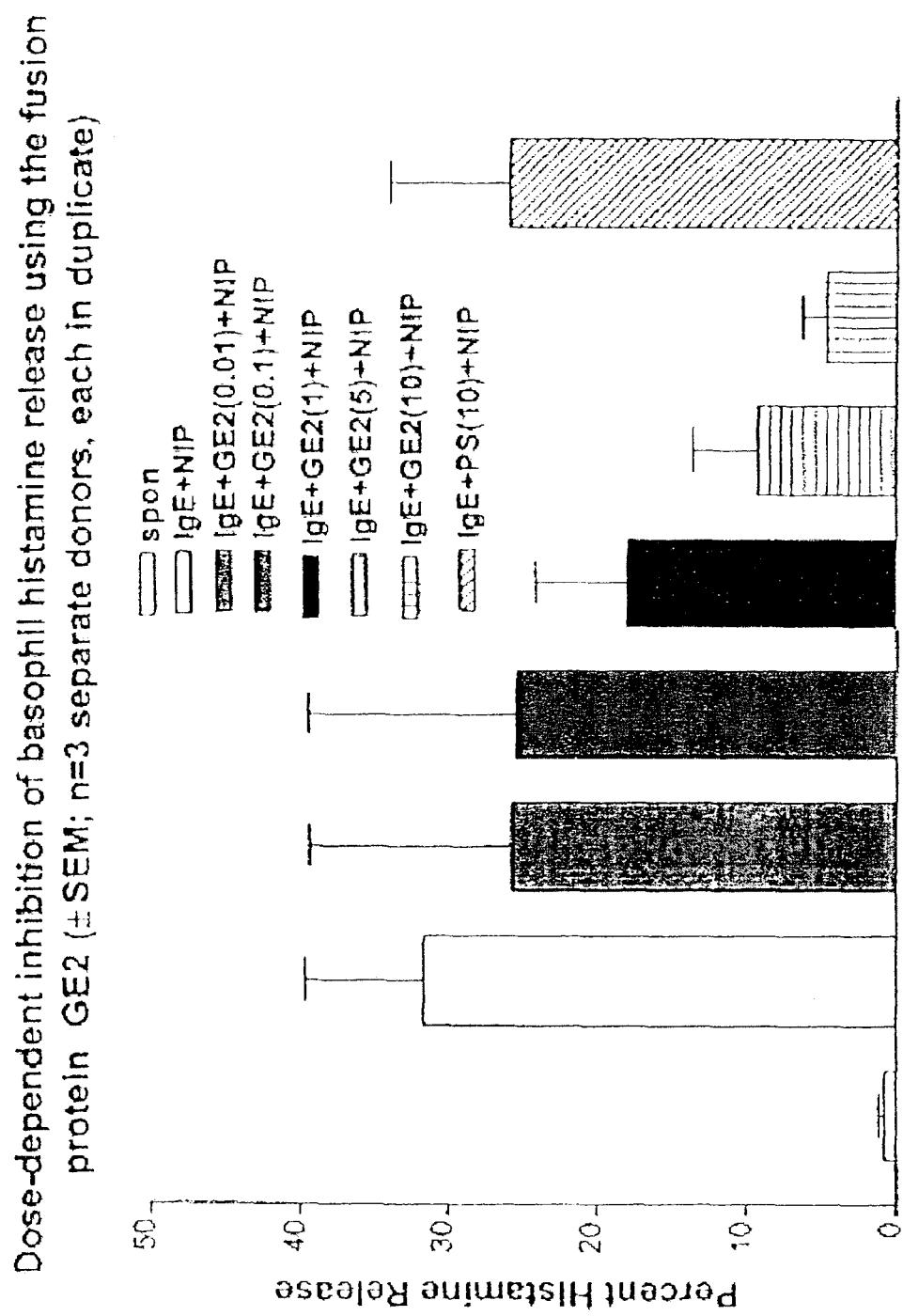
FIG. 8 illustrates the dose-dependent inhibition of basophil histamine release using the fusion protein GE2 (±SEM; n=3 separate donors, each in duplicate). Purified human blood basophils were acid stripped and then sensitized with humanized anti-NP IgE, labeled as IgE, alone or in the presence of GE2 protein or PS that is a purified human IgE myeloma protein. One hour later, cells were challenged with NP-BSA and the resulting level of histamine release measured.

Unless defined otherwise, technical and scientific terms used herein have the same meaning as commonly understood by one of ordinary skill in the art to which this invention belongs. One skilled in the art will recognize many methods and materials similar or equivalent to those described herein; which could be used in the practice of the present invention. Indeed, the present invention is in no way limited to the methods and materials described. For purposes of the present invention, the following terms are defined below.

The term "functionally connected" with reference to the first and second polypeptide sequences included in the fusion molecules herein, is used to indicate that such first and second polypeptide sequences retain the ability to bind to the respective receptors. Thus, after being connected to a second polypeptide sequence, the first polypeptide sequence retains the ability of specific binding to a native IgG inhibitory receptor, such as a low-affinity FcγRIIb receptor. Similarly, after being connected to a first polypeptide sequence, the second polypeptide sequence retains the ability of specific binding, directly or indirectly, i.e. through a third polypeptide sequence, to a native IgE receptor, such as a native high-affinity IgE receptor, e.g. native human FcεRI, or a native low-affinity IgE receptor, e.g. FcεRII. As a result, the fusion molecule, comprising the first and second polypeptide sequences functionally connected to each other, is capable of cross-linking the respective native receptors, such as, for example, FcγRIIb and FcεRI or FcεRII. In order to achieve a functional connection between the two binding sequences within the fusion molecules of the invention, it is preferred that they retain the ability to bind to the corresponding receptor with a binding affinity similar to that of a native immunoglobulin heavy chain or other native polypeptide binding to that receptor.

The binding is "specific" when the binding affinity of a molecule for a binding target, e.g. an IgG or IgE receptor, is significantly higher (preferably at least about 2-times, more preferably at least about 4-times, most preferably at least about 6-times higher) than the binding affinity of that molecule to any other known native polypeptide.

The term "inhibitory receptor" is used in the broadest sense and refers to a receptor capable of down-regulating a biological response mediated by another receptor, regardless of the mechanism by which the down-regulation occurs.

The terms "receptor comprising an immune receptor tyrosine-based inhibitory motif (ITIM)" and "ITIM-containing receptor" are used to refer to a receptor containing one or more immune receptor tyrosine-based inhibitory motifs, ITIMs. The ITIM motif can be generally represented by the formula Val/Ile-Xaa-PTyr-Xaa-Xaa-Leu/Val (where Xaa represents any amino acid). ITIM-containing receptors include, without limitation, FcγRIIb, gp49b1/gp91 (Arm et al., *J. Biol. Chem.* 266:15966-73 (1991)), p91/PIR-B (Hayami et al., *J. Biol. Chem.* 272:7320-7 (1997)), LIR1-3, 5, 8, LAIR-1; CD22 (van Rossenberg et al., *J. Biol. Chem.* Jan. 4, 2001); CTL-4, CD5, p58/70/140 KIR, PIRB2-5; NKB1, Ly49 A/C/E/F/G, NKG2-A/B, APC-R, CD66, CD72, PD-1, SHPS-1, SIRP-α1, IL T1-5, MIR7, 10, hMIR(HM18), hMIR(HM9), Fas(CD95), TGFβ-R, TNF-R1, IFN-γ-R (α- and β-chains), mast cell function Ag, H2-M, HLA-DM, CD1, CD1-d, CD46, c-cbl, Pyk2/FADK2, P130 Ca rel prot, PGDF-R, LIF, LIR-R, CIS, SOCS13 and 3, as reviewed in Sinclair N R et al., supra. Ligands for many of these receptors are also known, such as, e.g. the ligand for CD95 is called CD95 ligand, the ligands for CTLA-4 are CD80 and CD86, the ligands of IFN-γ receptor is IFN-γ, etc. Ligands for CD22 comprise the basic binding motif Nau5Ac-a(2,6)-Lac, and are discussed, for example in van Rossenberg et al., 2001, supra.

The term "IgG inhibitory receptor" is used to define a member of the inhibitory receptor superfamily (IRS), now know or hereinafter discovered, that is capable of attenuating an FcεR-mediated response, regardless of whether it is mediated via IgE acting through a high-affinity IgE receptor, e.g. FcεRI, or a low-affinity IgE receptor, or by another mechanism such as an autoantibody to the FcεR. The response preferably is an IgE-mediated allergic response, such as a type I (immediate hypersensitivity) reaction but could include autoimmune reactions due to anti-FcεRI α-chain antibodies that have been reported in about half of the cases of chronic idiopathic urticaria.

The term "native" or "native sequence" refers to a polypeptide having the same amino acid sequence as a polypeptide that occurs in nature. In accordance with the present invention, a polypeptide can be considered "native" regardless of its source, mode of preparation or state of purification. Thus, such native sequence polypeptide can be isolated from nature or can be produced by recombinant and/or synthetic means. The terms "native" and "native sequence" specifically encompass naturally-occurring truncated or secreted forms (e.g., an extracellular domain sequence), naturally-occurring variant forms (e.g., alternatively spliced forms) and naturally-occurring allelic variants of a polypeptide.

The terms "native FcγRIIb," "native sequence FcγRIIb," "native low-affinity IgG inhibitory receptor FcγRIIb," and "native sequence low-affinity IgG inhibitory receptor FcγRIIb" are used interchangeably, and refer to FcγRIIb receptors of any species, including any mammalian species, as occurring in nature. Preferably, the mammal is human. FcγRIIb is an isoform of the low-affinity IgG receptor FcγRII containing an immunoreceptor tyrosine-based inhibition motif (ITIM). This receptor is the principal FcγRII species in human peripheral blood basophils and cord blood-derived mast cells. For further details see, for example, Malbec and Fridman, *Curr. Top. Microbiol. Immunol.* 244:13-27 (1999); Cambier, J. C., *Proc. Natl. Acad. Sci. USA* 94:5993-5995 (1997); and Ott and Cambier, *J. Allergy Clin. Immunol.* 106 (3):429-440 (2000). FcγRIIb has three alternatively spliced forms designated FcγRIIb1, FcγRIIb1', and FcγRIIb2, which differ only in their cytoplasmic domain sequences. All three alternatively spliced isoforms contain two extracellular Ig-like loops and a single conserved ITIM motif within their cytoplasmic tails, and are specifically included within the definition of FcγRIIb, along with other splice variants that might be identified in the future.

The terms "native FcεRI," "native sequence FcεRI," "native high-affinity IgE receptor FcεRI," and "native sequence high-affinity IgE receptor FcεRI" are used interchangeably and refer to FcεRI receptors of any species, including any mammalian species, that occur in nature. FcεRI is a member of the multi-subunit immune response receptor (MIRR) family of cell surface receptors that lack intrinsic enzymatic activity but transduce intracellular signals through association with cytoplasmic tyrosine kinases. For further details see, for example, Kinet, J. P., *Annu. Rev. Immunol.* 17:931-972 (1999) and Ott and Cambier, *J. Allergy Clin. Immunol.*, 106:429-440 (2000).

The terms "native FcεRII (CD23)," "native sequence FcεRII (CD23)," native low-affinity IgE receptor FcεRII (CD23)," "native sequence low-affinity IgE receptor FcεRII (CD23)" are used interchangeably and refer to FcεRII (CD23) receptors of any species, including any mammalian species, that occur in nature. Several groups have cloned and expressed low-affinity IgE receptors of various species. The cloning and expression of a human low-affinity IgE receptor is reported, for example, by Kikutani et al., *Cell* 47:657-665 (1986), and Ludin et al., *EMBO J.* 6:109-114 (1987). The cloning and expression of corresponding mouse receptors is disclosed, for example, by Gollnick et al., *J. Immunol.* 144: 1974-82 (1990), and Kondo et al., *Int. Arch. Allergy Immunol.* 105:38-48 (1994). The molecular cloning and sequencing of CD23 for horse and cattle has been recently reported by Watson et al., *Vet. Immunol. Immunopathol.* 73:323-9 (2000). For an earlier review of the low-affinity, IgE receptor see also Delespesse et al., *Immunol. Rev.* 125:77-97 (1992).

The term "mammal" or "mammalian species" refers to any animal classified as a mammal, including humans, domestic and farm animals, and zoo, sports, or pet animals, such as dogs, cats, cattle, horses, sheep, pigs, goats, rabbits, as well as rodents such as mice and rats, etc. Preferably, the mammal is human.

The terms "subject" or "patient," as used herein, are used interchangeably, and can refer to any to animal, and preferably a mammal, that is the subject of an examination, treatment, analysis, test or diagnosis. In one embodiment, humans are a preferred subject. A subject or patient may or may not have a disease or other pathological condition.

The terms "peptide," "polypeptide" and "protein," in singular or plural, as used herein, all refer to a primary sequence of amino acids joined to each other in a linear chain by covalent peptide bonds. In general, a peptide consists of a small number of amino acid residues, typically from two to about 50 amino acids in length, and is shorter than a protein. As used in the art, the term "peptides" can be used interchangeably with "oligopeptides" and "oligomers." The term "polypeptide" encompasses peptides and proteins. Peptides, polypeptides and proteins can be from a natural source, or be recombinant, or synthetic. Polypeptides, as defined herein, may contain amino acids other than the 20 naturally occurring amino acids, and may include modified amino acids. The modification can be anywhere within the polypeptide molecule, such as, for example, at the terminal amino acids, and may be due to natural processes, such as processing and other post-translational modifications, or may result from chemical and/or enzymatic modification techniques which are well known to the art. The known modifications include, without limitation, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. Such modifications are well known to those of skill and have been described in great detail in the scientific literature, such as, for instance, Creighton, T. E., Proteins—Structure And Molecular Properties, 2nd Ed., W. H. Freeman and Company, New York (1993); Wold, F., "Posttranslational Protein Modifications: Perspectives and Prospects," in Post-translational Covalent Modification of Proteins, Johnson, B. C., ed., Academic Press, New York (1983), pp. 1-12; Seifter et al., "Analysis for protein modifications and nonprotein cofactors," *Meth. Enzymol.* 182:626-646 (1990), and Rattan et al., *Ann. N.Y. Acad. Sci.* 663:48-62 (1992).

Modifications can occur anywhere in a polypeptide, including the peptide backbone, the amino acid side-chains and the amino or carboxyl termini. In fact, blockage of the amino or carboxyl group in a polypeptide, or both, by a covalent modification, is common in naturally occurring and synthetic polypeptides and such modifications may be present in polypeptides of the present invention, as well. For instance, the amino terminal residue of polypeptides made in *E. coli*, prior to proteolytic processing, almost invariably will be N-formylmethionine. Accordingly, when glycosylation is desired, a polypeptide is expressed in a glycosylating host, generally eukaryotic host cells. Insect cells often carry out the same post-translational glycosylations as mammalian cells and, for this reason, insect cell expression systems have been developed to express efficiently mammalian proteins having native patterns of glycosylation.

It will be appreciated that polypeptides are not always entirely linear. For instance, polypeptides may be branched as a result of ubiquitination, and they may be circular, with or without branching, generally as a result of post-translational events, including natural processing and events brought about by human manipulation which do not occur naturally. Circular, branched and branched circular polypeptides may be synthesized by non-translation natural process and by entirely synthetic methods, as well. Such structures are within the scope of the polypeptides as defined herein.

Amino acids are represented by their common one- or three-letter codes, as is common practice in the art. Accordingly, the designations of the twenty naturally occurring amino acids are as follows: Alanine=Ala (A); Arginine=Arg (R); Aspartic Acid=Asp (D); Asparagine=Asn (N); Cysteine=Cys (C); Glutamic Acid=Glu (E); Glutamine=Gln (O); Glycine=Gly (G); Histidine=His (H); Isoleucine=Ile (I); Leucine=Leu (L); Lysine=Lys (K); Methionine=Met (M); Phenylalanine=Phe (F); Proline=Pro (P); Serine=Ser (S); Threonine=Thr (T); Tryptophan=Trp (W); Tyrosine=Tyr (Y); Valine=Val (V). The polypeptides herein may include all L-amino acids, all D-amino acids or a mixture thereof. The polypeptides comprised entirely of D-amino acids may be advantageous in that they are expected to be resistant to proteases naturally found within the human body, and may have longer half-lives.

The term "amino acid sequence variant" refers to molecules with some differences in their amino acid sequences as compared to a reference (e.g. native sequence) polypeptide. The amino acid alterations may be substitutions, insertions, deletions or any desired combinations of such changes in a native amino acid sequence.

Substitutional variants are those that have at least one amino acid residue in a native sequence removed and a different amino acid inserted in its place at the same position. The substitutions may be single, where only one amino acid in the molecule has been substituted, or they may be multiple, where two or more amino acids have been substituted in the same molecule.

Insertional variants are those with one or more amino acids inserted immediately adjacent to an amino acid at a particular position in a native amino acid sequence. Immediately adjacent to an amino acid means connected to either the α-carboxy or α-amino functional group of the amino acid.

Deletional variants are those with one or more amino acids in the native amino acid sequence removed. Ordinarily, deletional variants will have at least one amino acid deleted in a particular region of the molecule.

The term "sequence identity" is defined as the percentage of amino acid residues in a candidate sequence that are identical with the amino acid residues in a reference polypeptide sequence (e.g., a native polypeptide sequence), after aligning the sequences and introducing gaps, if necessary, to achieve the maximum percent sequence identity, and not considering any "conservative substitutions" as part of the sequence identity, wherein conservative amino acid substitutions are the substitution of one amino acid for a different amino acid having similar chemical properties. The % sequence identity values are generated by the NCBI BLAST2.0 software as defined by Altschul et al., (1997), "Gapped BLAST and PSI-BLAST: a new generation of protein database search programs", *Nucleic Acids Res.*, 25:3389-3402. The parameters are set to default values, with the exception of the Penalty for mismatch, which is set to −1.

The term "sequence similarity" as used herein, is the measure of amino acid sequence identity, as described above, and in addition also incorporates conservative amino acid substitutions.

"Stringent" hybridization conditions are sequence dependent and will be different with different environmental parameters (e.g., salt concentrations, and presence of organics). Generally, stringent conditions are selected to be about 5° C. to 20° C. lower than the thermal melting point ($T_m$) for the specific nucleic acid sequence at a defined ionic strength and pH. Preferably, stringent conditions are about 5° C. to 10° C. lower than the thermal melting point for a specific nucleic acid bound to a perfectly complementary nucleic acid. The $T_m$ is the temperature (under defined ionic strength and pH) at which 50% of a nucleic acid (e.g., tag nucleic acid) hybridizes to a perfectly matched probe.

"Stringent" wash conditions are ordinarily determined empirically for hybridization of each set of tags to a corresponding probe array. The arrays are first hybridized (typically under stringent hybridization conditions) and then washed with buffers containing successively lower concentrations of salts, or higher concentrations of detergents, or at increasing temperatures until the signal to noise ratio for specific to non-specific hybridization is high enough to facilitate detection of specific hybridization. Stringent temperature conditions will usually include temperatures in excess of about 30° C., more usually in excess of about 37° C., and occasionally in excess of about 45° C. Stringent salt conditions will ordinarily be less than about 1000 mM, usually less than about 500 mM, more usually less than about 400 mM, typically less than about 300 mM, preferably less than about 200 mM, and more preferably less than about 150 mM. However, the combination of parameters is more important than the measure of any single parameter. See, e.g., Wetmur et al, *J. Mol. Biol.* 31:349-70 (1966), and Wetmur, *Critical Reviews in Biochemistry and Molecular Biology* 26(34):227-59 (1991).

In a preferred embodiment, "stringent conditions" or "high stringency conditions," as defined herein, may be hybridization in 50% formamide, 6×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (100 μg/ml), 0.5% SDS, and 10% dextran sulfate at 42° C., with washes at 42° C. in 2×SSC (sodium chloride/sodium citrate) and 0.1% SDS at 55° C., followed by a high-stringency wash consisting of 0.2×SSC containing 0.1% SDS at 42° C.

The terms "complement," "complementarity" or "complementary," as used herein, are used to describe single-stranded polynucleotides related by the rules of antiparallel base-pairing. For example, the sequence 5'-CTAGT-3' is completely complementary to the sequence 5'-ACTAG-3'. Complementarity may be "partial," where the base pairing is less than 100%, or complementarity may be "complete" or "total," implying perfect 100% antiparallel complementation between the two polynucleotides. By convention in the art, single-stranded nucleic acid molecules are written with their 5' ends to the left, and their 3' ends to the right.

The term "immunoglobulin" (Ig) is used to refer to the immunity-conferring portion of the globulin proteins of serum, and to other glycoproteins, which may not occur in nature but have the same functional characteristics. The term "immunoglobulin" or "Ig" specifically includes "antibodies" (Abs). While antibodies exhibit binding specificity to a specific antigen, immunoglobulins include both antibodies and other antibody-like molecules that lack antigen specificity. Native immunoglobulins are secreted by differentiated B cells termed plasma cells, and immunoglobulins with unidentified antigen specificity are constitutively produced at low levels by the immune system and at increased levels by myelomas. As used herein, the terms "immunoglobulin," "Ig," and grammatical variants thereof are used to include antibodies, and Ig molecules without known antigen specificity, or without antigen binding regions.

The term "specific antibody" as used herein is intended to indicate an antibody that has binding specificity to a specified antigen. Although all antibodies are by nature specific for at least one epitope, the expression "specific antibody" implies that the antibody binds specifically to a particular known antigen. Binding specificity is determined by the amino acid sequences and conformation of the Ig variable domains of the heavy and light chains, as well as the conformation of the recognized epitope. The antigenic epitopes typically, but not exclusively, consist of small amino acid sequence domains. For example, the anti-myelin-basic-protein (MBP) autoantibody is specific for the MBP antigen, and more specifically, for the $MBP_{83-99}$ region. "Specific binding" and "specifically binding" refer to the interaction between an antibody and its specific antigen that is dependent on the presence of complementary structures on the antigenic epitope and the antibody.

Native immunoglobulins are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has-regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light-chain variable domain is aligned with the variable domain of the heavy chain. Particular amino acid residues are believed to form an interface between the light- and heavy-chain variable domains.

The main Ig isotypes (classes) found in serum, and the corresponding Ig heavy chains, shown in parentheses, are listed below:

IgG (γ chain): the principal Ig in serum, the main antibody raised in response to an antigen, has four major subtypes, several of which cross the placenta;

IgE (ε chain): this Ig binds tightly to mast cells and basophils, and when additionally bound to antigen, causes release of histamine and other mediators of immediate hypersensitivity; plays a primary role in allergic reactions, including hay fever, asthma and anaphylaxis; and may serve a protective role against parasites;

IgA (α chain): this Ig is present in external secretions, such as saliva, tears, mucous, and colostrum;

IgM (μ chain): the Ig first induced in response to an antigen; it has lower affinity than antibodies produced later and is pentameric; and IgD (δ chain): this Ig is found in relatively high concentrations in umbilical cord blood, serves primarily as an early cell receptor for antigen, and is the main lymphocyte cell surface molecule.

Antibodies of the IgG, IgE, IgA, IgM, and IgD isotypes may have the same variable regions, i.e. the same antigen binding cavities, even though they differ in the constant region of their heavy chains. The constant regions of an immunoglobulin, e.g. antibody are not involved directly in binding the antibody to an antigen, but correlate with the different effector functions mediated by antibodies, such as complement activation or binding to one or more of the antibody Fc receptors expressed on basophils, mast cells, lymphocytes, monocytes and granulocytes.

Some of the main antibody isotypes (classes) are divided into further sub-classes. IgG has four known subclasses: $IgG_1$ ($\gamma_1$), $IgG_2$ ($\gamma_2$), $IgG_3$ ($\gamma_3$), and $IgG_4$ ($\gamma_4$), while IgA has two known sub-classes: $IgA_1$ ($\alpha_1$) and $IgA_2$ ($\alpha_2$).

A light chain of an Ig molecule is either a κ or a λ chain.

The constant region of an immunoglobulin heavy chain is further divided into globular, structurally discrete domains, termed heavy chain constant domains. For example, the constant region of an $IgG_1$ immunoglobulin heavy chain comprises three constant domains, CH1, CH2 and CH3, and a hinge region between the CH1 and CH2 domains. The IgE immunoglobulin heavy chain comprises four constant domains: CH1, CH2, CH3 and CH4 and does not have a hinge region.

Immunoglobulin sequences, including sequences of immunoglobulin heavy chain constant regions are well known in the art and are disclosed, for example, in Kabat et al., *Sequences of Proteins of Immunological Interest,* 5th Ed. Public Health Service, National Institute of Health, Bethesda, Md. (1991). For a discussion of the human $IgG_1$ heavy chain constant region ($\gamma_1$), see also Ellison et al., *Nucl. Acid Res.* 10:4071-4079 (1982); and Takahashi et al., *Cell* 29:671-679 (1982). For a discussion of the human $IgG_2$ constant region ($\gamma_2$), see also Krawinkel et al., *EMBO J.* 1:403-407 (1982); Ellison et al., *Proc. Nat. Acad. Sci. USA* 79:1984-1988 (1982); and Takahashi et al. (1982), supra. For a discussion of human $IgG_3$ heavy chain constant region ($\gamma_3$), see also Krawinkel et al., (1982), supra, and Takahashi et al. (1982), supra. For a discussion of human $IgG_4$ heavy chain constant region ($\gamma_4$), see also Ellison et al., *DNA* 1:11-18 (1982), Krawinkel et al. (1982), supra, and Takahashi et al. (1982), supra. For a discussion of the human IgE heavy chain constant region (ε), see also Max et al., *Cell* 29:691-699 (1982). IgE isoforms are described in Saxon et al., *J. Immunol.* 147:4000 (1991); Peng et al., *J. Immunol.* 148:129-136 (1992); Zhang et al., *J. Exp. Med.* 176:233-243 (1992); and Hellman, *Eur. J. Immunol.* 23:159-167 (1992).

The term "antigen," as used herein, refers to any agent that is recognized by an antibody, while the term "immunogen" refers to any agent that can elicit an immunological response in a subject. The terms "antigen" and "immunogen" both encompass, but are not limited to, polypeptides. In most, but not all cases, antigens are also immunogens. The term "allergen," and grammatical variants thereof, as used herein, refer to antigens that are capable of inducing IgE-mediated responses, e.g., allergies. An allergen can be almost anything that acts as an antigen and stimulates an IgE-mediated allergic reaction. Common allergens can be found, for example, in food, pollen, mold, house dust which may contain mites as well as dander from house pets, venom from insects such as bees, wasps and mosquitoes.

The terms "epitope" or "antigenic determinant" as used herein, refer to that portion of an antigen that makes contact with a particular antibody variable region, and thus imparts specificity to the antigen/antibody binding. A single antigen may have more than one epitope. An immunodominant epitope is an epitope on an antigen that is preferentially recognized by antibodies to the antigen. In some cases, where the antigen is a protein, the epitope can be "mapped," and an "antigenic peptide" produced corresponding approximately to just those amino acids in the protein that are responsible for the antibody/antigen specificity. Such "antigenic peptides" find use in peptide immunotherapies.

The terms "autoantigen" and "self antigen" and grammatical equivalents, as used herein, refer to an antigen endogenous to an individual's physiology, that is recognized by either the cellular component (T-cell receptors) or humoral component (antibodies) of that individual's immune system. The presence of autoantigens, and consequently autoantibodies and/or self-reactive T-cells, is frequently, but not absolutely, associated with disease states. Autoantibodies may be detected in disease-free individuals. Autoantigens are frequently, but not exclusively, polypeptides. An understanding of the mechanisms underlying the recognition of autoantigens, the loss of normal self-recognition, or the mechanisms inducing autoimmunity are not necessary to make or use the present invention.

The term "autoantibody," as used herein, is intended to refer to any antibody produced by a host organism that binds specifically to an autoantigen, as defined above. The presence of autoantibodies and/or self-reactive T-cells is referred to herein as "autoimmunity." The presence of autoantibodies or self-reactive T-cells in a subject is frequently, but not absolutely, associated with disease (i.e., autoimmune disease).

The terms "disease," "disorder" and "condition" are used interchangeably herein, and refer to any disruption of normal body function, or the appearance of any type of pathology. The etiological agent causing the disruption of normal physiology may or may not be known. Furthermore, although two patients may be diagnosed with the same disorder, the particular symptoms displayed by those individuals may or may not be identical.

The terms "autoimmune disease," "autoimmune condition" or "autoimmune disorder," as used interchangeably herein, refer to a set of sustained organ-specific or systemic clinical symptoms and signs associated with altered immune homeostasis that is manifested by qualitative and/or quantitative defects of expressed autoimmune repertoires. Autoimmune disease pathology is manifested as a result of either structural or functional damage induced by the autoimmune response. Autoimmune diseases are characterized by humoral (e.g., antibody-mediated), cellular (e.g., cytotoxic T lymphocyte-mediated), or a combination of both types of immune responses to epitopes on self-antigens. The immune system of the affected individual activates inflammatory cascades aimed at cells and tissues presenting those specific self-antigens. The destruction of the antigen, tissue, cell type or organ attacked gives rise to the symptoms of the disease. The autoantigens are known for some, but not all, autoimmune diseases.

The terms "immunotherapy," "desensitisation therapy," "hyposensitisation therapy," "tolerance therapy" and the like, as used herein, describe methods for the treatment of various hypersensitivity disorders, where the avoidance of an allergen or autoantigen is not possible or is impractical. As used herein, these terms are used largely interchangeably. These methods generally entail the delivery to a subject of the antigenic material in a controlled manner to induce tolerance to the antigen and/or downregulate an immune response that occurs upon environmental exposure to the antigen. These therapies typically entail injections of the antigen (e.g., an allergen or autoantigen) over an extended period of time (months or years) in gradually increasing doses. The antigen used in the immunotherapies is typically, but not exclusively, polypeptides. For example, hayfever desensitisation therapy downregulates allergic response to airborn pollen, where the subject is injected with a pollen extract. From a clinical perspective, these treatments are suboptimal, as the injections are typically painful, as well as inconvenient. Furthermore, a significant risk of potentially life-threatening anaphylactic responses during the therapies exists. Adapting immunotherapy techniques for the treatment of various autoimmune disorders has been proposed, where the autoantigen is administered to a subject in the hope of inducing tolerance to the autoantigen, and thereby eliminating the immune destruction of the endogenous autoantigen or autoantigenic tissue. For example, insulin and myelin-basic-protein have been delivered to animal models and humans for the purpose of downregulating autoimmune type-I diabetes mellitus and multiple sclerosis, respectively.

The terms "peptide therapy" and "peptide immunotherapy," and the like, as used herein, describe methods of immunotherapy, wherein the antigen (e.g., an allergen or autoantigen) delivered to a subject is a short polypeptide (i.e., a peptide). Furthermore, the peptide delivered during peptide therapy may preferably contain only those amino acids defining an immunodominant epitope (e.g., the myelin-basic-protein epitope ($MBP_{83-99}$).

The terms "vaccine therapy," "vaccination" and "vaccination therapy," as used interchangeably herein, refer in general to any method resulting in immunological prophylaxis. In one aspect, vaccine therapy induces an immune response, and thus long-acting immunity, to a specific antigen. These methods generally entail the delivery to a subject of an immunogenic material to induce immunity. In this case, the immunogenic material is generally killed microbes of virulent stains or living, attenuated strains, or derivatives or products of virulent pathogens. In another aspect, the "vaccine therapy" refers to a method for the downregulation of an immune potential to a particular antigen (e.g., to suppress an allergic response). This type of vaccine therapy is also referred to as "tolerance therapy." Vaccine therapies typically entail a series of parenteral or oral administrations of the immunogenic material over an extended period of time.

The terms "fragment," "portion" and "part," as used interchangeably herein, refer to any composition of matter that is smaller than the whole of the composition of matter from which it is derived. For example, a portion of a polypeptide may range in size from two amino acid residues to the entire amino acid sequence minus one amino acid. However, in most cases, it is desirable for a "portion" or "fragment" to retain an activity or quality which is essential for its intended use. For example, useful portions of an antigen are those portions that retain an epitope determinant. Also, in one embodiment, useful portions of an immunoglobulin heavy chain constant region are those portions that retain the ability to form covalent homodimeric structures and are able to bind an $F_c\gamma$ receptor.

The term "at least a portion," as used herein, is intended to encompass portions as well as the whole of the composition of matter.

The terms "type I allergic reaction," "immediate hypersensitivity," "atopic allergy," "type-I hypersensitivity," and the like, as used herein, refer to the physiological response that occurs when an antigen entering the body encounters mast cells or basophils which have been sensitized by IgE attached to its high-affinity receptor, FcεRI on these cells. When an allergen reaches the sensitized mast cell or basophil, it cross-links surface-bound IgE, causing an increase in intracellular calcium ($Ca^{2+}$) that triggers the release of pre-formed mediators, such as histamine and proteases, and newly synthesized, lipid-derived-mediators such as leukotrienes and prostaglandins. These autocoids produce the clinical symptoms of allergy. In addition, cytokines, e.g., IL-4, TNF-alpha, are released from degranulating basophils and mast cells, and serve to augment the inflammatory response that accompanies an IgE reaction (see, e.g., Immunology, Fifth Edition, Roitt et al., eds., 1998, pp. 302-317). The specific manifestations of the hypersensitivity reaction in the sensitive or allergic subject depends on the site of the allergen exposure, the dose of allergen exposure, the reactivity of the organs in the subject (e.g., over-reactive lungs or nose) and the full panoply of the immune response to the allergen in that subject.

Symptoms and signs associated with type I hypersensitivity responses are extremely varied due to the wide range of tissues and organs that can be involved. These symptoms and signs can include, but are not limited to: itching of the skin, eyes, and throat, swelling and rashes of the skin (angioedema and urticaria/hives), hoarseness and difficulty breathing due to swelling of the vocal cord area, a persistent bumpy red rash that may occur anywhere on the body, shortness of breath and wheezing (from tightening of the muscles in the airways and plugging of the airways, i.e., bronchoconstriction) in addition to increased mucus and fluid production, chest tightness and pain due to construction of the airway muscles, nausea, vomiting diarrhea, dizziness and fainting from low blood pressure, a rapid or irregular heartbeat and even death as a result of airway and/or cardiac compromise.

Examples of disease states that result from allergic reactions, and demonstrating hypersensitivity symptoms and/or signs include, but are not limited to, allergic rhinitis, allergic conjunctivitis, atopic dermatitis, allergic [extrinsic] asthma, some cases of urticaria and angioedema, food allergy, and anaphylactic shock in which there is systemic generalized reactivity and loss of blood pressure that may be fatal.

The terms "anaphylaxis," "anaphylactic response," "anaphylactic reaction," "anaphylactic shock," and the like, as used interchangeably herein, describe the acute, often explosive, IgE-mediated systemic physiological reaction that occurs in a previously sensitized subject who receives the sensitizing antigen. Anaphylaxis occurs when the previously sensitizing antigen reaches the circulation. When the antigen reacts with IgE on basophils and mast cells, histamine, leukotrienes, and other inflammatory mediators are released. These mediators cause the smooth muscle contraction (responsible for wheezing and gastrointestinal symptoms) and vascular dilation (responsible for the low blood pressure) that characterize anaphylaxis. Vasodilation and escape of plasma into the tissues causes urticaria and angioedema and results in a decrease in effective plasma volume, which is the major cause of shock. Fluid escapes into the lung alveoli and may produce pulmonary edema. Obstructive angioedema of the upper airway may also occur. Arrhythmias and cardiogenic shock may develop if the reaction is prolonged. The term "anaphylactoid reaction" refers to a physiological response that displays characteristics of an anaphylactic response.

Symptoms of an anaphylactic reaction vary considerably among patients. Typically, in about 1 to 15 minutes (but rarely after as long as 2 hours), symptoms can include agitation and flushing, palpitations, paresthesias, pruritus, throbbing in the ears, coughing, sneezing, urticaria and angioedema, vasodilation, and difficulty breathing owing to laryngeal edema or bronchospasm. Nausea, vomiting, abdominal pain, and diarrhea are also sometimes observed. Shock may develop within another 1 or 2 minutes, and the patient may convulse, become incontinent, unresponsive, and succumb to cardiac arrest, massive angioedema, hypovolemia, severe hypotension and vasomotor collapse and primary cardiovascular collapse. Death may ensue at this point if the antagonist epinephrine is not immediately available. Mild forms of anaphylactic response result in various symptoms including generalized pruritus, urticaria, angioedema, mild wheezing, nausea and vomiting. Patients with the greatest risk of anaphylaxis are those who have reacted previously to a particular drug or antigen.

The terms "vector", "polynucleotide vector", "construct" and "polynucleotide construct" are used interchangeably herein. A polynucleotide vector of this invention may be in any of several forms, including, but not limited to, RNA, DNA, RNA encapsulated in a retroviral coat, DNA encapsulated in an adenovirus coat, DNA packaged in another viral or viral-like form (such as herpes simplex, and adeno-associated virus (AAV)), DNA encapsulated in liposomes, DNA complexed with polylysine, complexed with synthetic polycationic molecules, conjugated with transferrin, complexed with compounds such as polyethylene glycol (PEG) to immunologically "mask" the molecule and/or increase half-life, or conjugated to a non-viral protein. Preferably, the polynucleotide is DNA. As used herein, "DNA" includes not only bases A, T, C, and G, but also includes any of their analogs or modified forms of these bases, such as methylated nucleotides, internucleotide modifications such as uncharged linkages and thioates, use of sugar analogs, and modified and/or alternative backbone structures, such as polyamides.

A "host cell" includes an individual cell or cell culture which can be or has been a recipient of any vector of this invention. Host cells include progeny of a single host cell, and the progeny may not necessarily be completely identical (in morphology or in total DNA complement) to the original parent cell due to natural, accidental, or deliberate mutation and/or change. A host cell includes cells transfected or infected in vivo with a vector comprising a nucleic acid of the present invention.

The term "promoter" means a nucleotide sequence that, when operably linked to a DNA sequence of interest, promotes transcription of that DNA sequence.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accord with conventional practice.

The term "IgE-mediated biological response" is used to refer to a condition or disease which is characterized by signal transduction through an IgE receptor, including the high-affinity IgE receptor, FcεRI, and the low-affinity IgE receptor FcεRII. The definition includes, without limitation, conditions associated with anaphylactic hypersensitivity and atopic allergies, such as, for example, asthma, allergic rhinitis, atopic dermatitis, food allergies, chronic urticaria and angioedema, as well as the serious physiological condition of anaphylactic shock, usually caused by bee stings or medications such as penicillin.

The terms "treat" or "treatment" refer to both therapeutic treatment and prophylactic or preventative measures, wherein the object is to prevent or slow down (lessen) an undesired physiological change or disorder. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. Those in need of treatment include those already with the condition or disorder as well as those prone to have the condition or disorder or those in which the condition or disorder is to be prevented.

"Chronic" administration refers to administration of the agent(s) in a continuous mode as opposed to an acute mode, so as to maintain a desired effect or level of agent(s) for an extended period of time.

"Intermittent" administration is treatment that is not consecutively done without interruption, but rather is periodic in nature.

Administration "in combination with" one or more further therapeutic agents includes simultaneous (concurrent) and consecutive administration in any order.

An "effective amount" is an amount sufficient to effect beneficial or desired therapeutic (including preventative) results. An effective amount can be administered in one or more administrations.

"Carriers" as used herein include pharmaceutically acceptable carriers, excipients, or stabilizers which are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™.

The terms "protease," "peptidase" or "proteinase," and grammatical equivalents as used interchangeably herein, refer to any polypeptide that is able to cleave covalent peptide bonds. Collectively, these proteases, peptidases and proteinases can be referred to as "proteolytic enzymes." Numerous proteolytic enzymes are known, and are generally classified by their cleavage specificities, or lack thereof. Cleavage specificity can be determined by the primary sequence of amino acids in the target polypeptide, as well as the spatial conformation of those amino acids. For example, exopeptidase proteolytic activity cleaves either an amino-terminal (N-terminal) amino acid, or the carboxy-terminal (C-terminal) amino acid from a larger polypeptide. Endopeptidase enzymes cleave at a peptide bond that is internal to the polypeptide (i.e., not at either the N-terminal or C-terminal amino acid positions). Some proteolytic enzymes have very fastidious cleavage specificity, where cleavage requires recognition of an extended amino acid target sequence. Alternatively, some peptidases have a more relaxed requirement for cleavage site recognition, and require only the presence of a single amino acid to target the proteolysis event. For example, cysteine, aspartate or arginine family endoproteases will cleave at internal cysteine, aspartate or asparagine amino acid residues, respectively. In some cases, the cysteine, aspartate or arginine endoprotease will require the presence or absence of other amino acids adjacent to or in the vicinity of the target cysteine, aspartate or arginine residue to effect cleavage. For example, some aspartate family endopeptidases are unable to cleave the aspartate peptide bond if the adjacent amino acid is a proline. Thus, a peptidase "cleavage site," as used herein, may encompass more amino acids than only the target residue for cleavage.

II. Description of Certain Preferred Embodiments

1. Design of the Fusion Molecules

In one embodiment, the present invention provides fusion molecules that are capable of attenuating a biological response mediated by an FcεR, such as conditions associated with anaphylactic hypersensitivity (including anaphylactic reactions resulting from peptide therapies for the treatment of allergic or autoimmune diseases) and atopic allergies, by cross-linking an inhibitory receptor expressed on mast cells and/or basophils with an IgE receptor. The actual sequence of the fusion molecule will depend on the targeted inhibitory receptor, such as an ITIM-containing receptor, e.g. various forms of FcγRIIb, inhibitory members of the gp49 family, especially gp49b1, p91/PIR-B, LAIR-1, LIR-1, or CD22, and on the targeted IgE receptors, e.g. FcεRI or FcεRII.

In a preferred embodiment, the inhibitory receptor is a native low-affinity FcγRIIb receptor, and the IgE receptor is a native high-affinity or low-affinity IgE receptor, i.e. FCεRI or FcεRII, more preferably FcεRI. Accordingly, the first polypeptide sequence present in the fusion molecules binds to the native low-affinity FcγRIIb receptor, while the second polypeptide sequence, which is functionally connected to the first polypeptide sequence, binds to a native FcεRI or FcεRII, preferably FcεRI. When the goal is to cross-link a native FcγRIIb receptor with a native FcεRI receptor by direct binding of the first and second polypeptide sequences present in the single-chain fusion molecules of the invention to the respective receptors, the first and second polypeptide sequences, which are functionally connected, are preferably, but not necessarily, designed to bind to the respective receptors at essentially the same region(s) as native IgG and IgE, respectively. It has been reported that the CH2-CH3 interface of the IgG Fc domain contains the binding sites for a number of Fc receptors, including the FcγRIIb low-affinity receptor (Wines et al., *J. Immunol.* 164(10):5313-5318 (2000)). Based on FcεRI binding studies, Presta et al., *J. Biol. Chem.* 269: 26368-26373 (1994) proposed that six amino acid residues (Arg-408, Ser-411, Lys-415, Glu-452, Arg-465, and Met-469) located in three loops, C-D, E-F, and F-G, computed to form the outer ridge on the most exposed side of the human IgE heavy chain CH3 domain, are involved in binding to the high-affinity receptor FcεRI, mostly by electrostatic interactions. Helm et al., *J. Cell Biol.* 271(13):7494-7500 (1996), reported that the high-affinity receptor binding site in the IgE molecule includes the Pro343-Ser353 peptide sequence within the CH3 domain of the IgE heavy chain, but sequences N- or C-terminal to this core peptide are also necessary to provide structural scaffolding for the maintenance of a receptor binding conformation. In particular, they found that residues, including His, in the C-terminal region of the ε-chain make an important contribution toward the maintenance of the high-affinity of interaction between IgE and FcεRI. The first and second polypeptide sequences within the fusion molecules of the invention are preferably designed to bind to residues within such binding regions.

In another class of the fusion molecules of the invention, the first polypeptide sequence will bind to an ITIM-containing receptor, other than FcγRIIb, expressed on mast cells, basophils and/or B cells. For example, the first polypeptide sequence may contain a region capable of specific binding to an inhibitory member of the gp49 family, such as gp49b1, which is a member of the immunoglobulin superfamily, is preferentially expressed on mast cells and mononuclear macrophages, and contains two ITIM motifs in its cytoplasmic domain. Another ITIM-containing inhibitory receptor is p91, also referred to as PIR-B, which is known to be expressed on B cells and myeloid lineage cells. Further ITIM-containing receptors that might be targeted by the fusion molecules of the invention include, without limitation, LAIR-1, expressed on B cells, in addition to NK cells, T cells and monocytes; LIR-1, expressed on B cells and monocytes; and CD22 expressed on B cells. For review of ITIM-containing receptors and related art see, e.g. Mustelin et al., *Front. Biosci.* 3:d1060-1096 (1998), and Sinclair et al., 1999, supra.

A second class of fusion molecules of the invention comprise a first and a second polypeptide sequence, wherein the second polypeptide sequence comprises part or whole of a native allergen or autoantigen amino acid sequence, or a variant thereof, binding between the second polypeptide sequence and an IgE receptor occurs indirectly via specific IgE molecules. The allergen- or autoantigen-derived sequence will bind to a specific IgE molecule bound to a high-affinity IgE receptor (FcεRI) on mast cells or basophils and/or to a low-affinity IgE receptor (FcεRII, CD23) on B lymphocytes. The first, inhibitory receptor-binding, sequence is designed as discussed above. In a preferred embodiment, the allergen or autoantigen part of the molecule is a fragment that contains only a single IgE binding site (or single immunodominant epitope), in order to avoid antigen cross-linking of IgE on the mast cell surface.

In a preferred embodiment, the first polypeptide sequence present in the fusion molecules of the invention has at least about 80%, more preferably at least about 85%, even more preferably at least about 90%, yet more preferably at least about 95%, most preferably at least about 99% sequence identity with the amino acid sequence of the hinge-CH2-CH3 region of a native IgG, e.g. IgG$_1$ immunoglobulin, preferably native human IgG$_1$. In a particularly preferred embodiment, the sequence identity is defined with reference to the human γhinge-CHγ2-CHγ3 sequence of SEQ ID NO: 3.

In another preferred embodiment, the first polypeptide sequence present in the fusion molecules of the invention has at least about 80%, more preferably at least about 85%, even more preferably at least about 90%, yet more preferably at least about 95%, most preferably at least about 99% sequence identity with the amino acid sequence of a native ligand of another ITIM-containing receptor expressed on mast cells, basophils and/or B cells, such as gp49b1 or p91/PIR-B (a cytoplasmic signaling protein activated by IFN-α, IFN-γ, and IL-6), or mast cell function Ag.

In yet another preferred embodiment, the first polypeptide sequence present in the fusion molecules of the invention has at least about 80%, more preferably at least about 85%, even more preferably at least about 90%, yet more preferably at least about 95%, most preferably at least about 99% sequence identity with the amino acid sequence of c-Kit (see, e.g., Yarden et al., *EMBO J.*, 6:3341-3351 [1987]).

In one embodiment, the second polypeptide sequence present in the fusion molecules of the invention preferably has at least about 80%, more preferably at least about 85%, even more preferably at least about 90%, yet more preferably at least about 95%, most preferably at least about 99% sequence identity with the amino acid sequence of the CH2-CH3-CH4 region of a native IgE immunoglobulin, preferably native human IgE, or with the sequence of a native allergen or autoantigen protein. In a particularly preferred embodiment, the sequence identity is defined with reference to the human CHϵ2-CHϵ3-CHϵ4 sequence of SEQ ID NO: 6 or with regard to one of the allergen sequences listed in Table 1 below, or, in one preferred embodiment, one of two Ara h2 clones, represented by SEQ ID NOs: 10 and 11, respectively.

TABLE 1

| Allergen | SWISS-PROT Entry | SWISS-PROT Accession No. | Protein Name | Source |
|---|---|---|---|---|
| Aln g 1 | MPAG__ALNGL | P38948 | Major Pollen Allergen Aln g 1 | Pollen of *Alnus glutinosa* (Alder) |
| Alt a 6 | RLA2__ALTAL | P42037 | 60S Acidic Ribosomal Protein P2 | *Alternaria alternata* |
| Alt a 7 | ALA7__ALTAL | P42058 | Minor Allergen Alt a 7 | *Alternaria alternata* |
| Alt a 10 | DHAL__ALTAL | P42041 | Aldehyde Dehydrogenase | *Alternaria alternata* |
| Alt a 12 | RLA1__ALTAL | P49148 | 60S Acidic Ribosomal Protein P1 | *Alternaria alternata* |
| Amb a 1 | MP11__AMBAR | P27759 | Pollen Allergen Amb a 1.1 [Precursor] | *Ambrosia artemisiifolia* (Short ragweed) |
| Amb a 1 | MP12__AMBAR | P27760 | Pollen Allergen Amb a 1.2 [Precursor] | *Ambrosia artemisiifolia* (Short ragweed) |
| Amb a 1 | MP13__AMBAR | P27761 | Pollen Allergen Amb a 1.3 [Precursor] | *Ambrosia artemisiifolia* (Short ragweed) |
| Amb a 1 | MP14__AMBAR | P28744 | Pollen Allergen Amb a 1.4 [Precursor] | *Ambrosia artemisiifolia* (Short ragweed) |
| Amb a 2 | MPA2__AMBAR | P27762 | Pollen Allergen Amb a 2 [Precursor] | *Ambrosia artemisiifolia* (Short ragweed) |
| Amb a 3 | MPA3__AMBEL | P00304 | Pollen Allergen Amb a 3 | *Ambrosia artemisiifolia* var. *elatior* (Short ragweed) |
| Amb a 5 | MPA5__AMBEL | P02878 | Pollen Allergen Amb a 5 | *Ambrosia artemisiifolia* var. *elatior* (Short ragweed) |
| Amb p 5 | MPA5__AMBPS | P43174 | Pollen Allergen Amb p 5-a [Precursor] | *Ambrosia psilostachya* (Western ragweed) |
| Amb p 5 | MP5B__AMBPS | P43175 | Pollen Allergen Amb p 5b [Precursor] | *Ambrosia psilostachya* (Western ragweed) |
| Amb t 5 | MPT5__AMBTR | P10414 | Pollen Allergen Amb t 5 [Precursor] | *Ambrosia trifida* (Giant ragweed) |
| Api g 1 | MPAG__APIGR | P49372 | Major Allergen Api g 1 | *Apium grayeolens* (Celery) |
| Api m 1 | PA2__APIME | P00630 | Phospholipase A2 [Precursor] [Fragment] | *Apis mellifera* (Honeybee) |
| Api m 2 | HUGA__APIME | Q08169 | Hyaluronoglucosaminidase [Precursor] | *Apis mellifera* (Honeybee) |
| Api m 3 | MEL__APIME | P01501 | Melittin [Precursor] | *Apis mellifera* (Honeybee) *Apis cerana* (Indian honeybee) |
| Ara h 1 | AH11__ARAHY | P43237 | Allergen Ara h 1, Clone P17 | *Arachis hypogaea* (Peanut) |
| Ara h 1 | AH12__ARAHY | P43238 | Allergen Ara h 1, Clone P41b | *Arachis hypogaea* (Peanut) |
| Ara t 8 | PRO1__ARATH | Q42449 | Profilin 1 | *Arabidopsis thaliana* (Mouse-ear cress) |
| Asp f 1 | RNMG__ASPRE | P04389 | Ribonuclease Mitogillin [Precursor] | *Aspergillus restrictus; Aspergillus fumigatus* (*Sartorya fumigata*) |
| Asp f 2 | MAF2__ASPFU | P79017 | Major Allergen Asp f 2 [Precursor] | *Aspergillus fumigatus* (*Sartorya fumigata*) |
| Asp f 3 | PM20__ASPFU | O43099 | Probable Peroxisomal Membrane Protein PMP20 | *Aspergillus fumigatus* (*Sartorya fumigata*) |
| Asp f 13 | AF13__ASPFU | O60022 | Allergen Asp f 13 [Precursor] | *Aspergillus fumigatus* (*Sartorya fumigata*) |
| Bet v 1 | BV1A__BETVE | P15494 | Major Pollen Allergen Bet v 1-a | *Betula verrucosa* (White birch) (*Betula pendula*) |
| Bet v 1 | BV1C__BETVE | P43176 | Major Pollen Allergen Bet v 1-c | *Betula verrucosa* (White birch) (*Betula pendula*) |
| Bet v 1 | BV1D__BETVE | P43177 | Major Pollen Allergen Bet v 1-d/h | *Betula verrucosa* (White birch) (*Betula pendula*) |

TABLE 1-continued

| Allergen | SWISS-PROT Entry | SWISS-PROT Accession No. | Protein Name | Source |
|---|---|---|---|---|
| Bet v 1 | BV1E_BETVE | P43178 | Major Pollen Allergen Bet v 1-e | *Betula verrucosa* (White birch) (*Betula pendula*) |
| Bet v 1 | BV1F_BETVE | P43179 | Major Pollen Allergen Bet v 1-f/i | *Betula verrucosa* (White birch) (*Betula pendula*) |
| Bet v 1 | BV1G_BETVE | P43180 | Major Pollen Allergen Bet v 1-g | *Betula verrucosa* (White birch) (*Betula pendula*) |
| Bet v 1 | BV1J_BETVE | P43183 | Major Pollen Allergen Bet v 1-j | *Betula verrucosa* (White birch) (*Betula pendula*) |
| Bet v 1 | BV1K_BETVE | P43184 | Major Pollen Allergen Bet v 1-k | *Betula verrucosa* (White birch) (*Betula pendula*) |
| Bet v 1 | BV1L_BETVE | P43185 | Major Pollen Allergen Bet v 1-l | *Betula verrucosa* (White birch) (*Betula pendula*) |
| Bet v 1 | BV1M_BETVE | P43186 | Major Pollen Allergen Bet v 1-m/n | *Betula verrucosa* (White birch) (Betula pendula) |
| Bet v 2 | PROF-BETVE | P25816 | Profilin | *Betula verrucosa* (White birch) (*Betula pendula*) |
| Bet v 3 | BTV3_BETVE | P43187 | Allergen Bet v 3 | *Betula verrucosa* (White birch) (*Betula pendula*) |
| Bla g 2 | ASP2_BLAGE | P54958 | Aspartic Protease Bla g 2 [Precursor] | *Blattella germanica* (German cockroach) |
| Bla g 4 | BLG4_BLAGE | P54962 | Allergen Bla g 4 [Precursor] [Fragment] | *Blattella germanica* (German cockroach) |
| Bla g 5 | GTS1_BLAGE | O18598 | Glutathione-S-transferase | *Blattella germanica* (German cockroach) |
| Blo t 12 | BT12_BLOTA | Q17282 | Allergen Blo t 12 [Precursor] | *Blomia tropicalis* (Mite) |
| Bos d 2 | ALL2_BOVIN | Q28133 | Allergen Bos d 2 [Precursor] | *Bos taurus* (Bovine) |
| Bos d 5 | LACB_BOVIN | P02754 | Beta-lactoglobulin [Precursor] | *Bos taurus* (Bovine) |
| Bra j 1 | ALL1_BRAJU | P80207 | Allergen Bra j 1-e, Small and Large Chains | *Brassica juncea* (Leaf mustard) (Indian mustard) |
| Can a 1 | ADH1_CANAL | P43067 | Alcohol Dehydrogenase 1 | *Candida albicans* (Yeast) |
| Can f 1 | ALL1_CANFA | O18873 | Major Allergen Can f 1 [Precursor] | *Canis famiiaris* (Dog) |
| Can f 2 | ALL2_CANFA | O18874 | Minor Allergen Can f 2 [Precursor] | *Canis familiaris* (Dog) |
| Car b 1 | MPA1_CARBE | P38949 | Major Pollen Allergen Car b 1, Isoforms 1A and 1B | *Carpinus betulus* (Hornbeam) |
| Car b 1 | MPA2_CARBE | P38950 | Major Pollen Allergen Car b 1, Isoform 2 | *Carpinus betulus* (Hornbeam) |
| Cha o 1 | MPA1_CHAOB | Q96385 | Major Pollen Allergen Cha o 1 [Precursor] | *Chamaecyparis obtusa* (Japanese cypress) |
| Cla h 3 | DHAL_CLAHE | P40108 | Aldehyde Dehydrogenase | *Cladosporium herbarum* |
| Cla h 3 | RLA3_CLAHE | P42038 | 60S Acidic Ribosomal Protein P2 | *Cladosporium herbarum* |
| Cla h 4 | HS70_CLAHE | P40918 | Heat Shock 70 KDa Protein | *Cladosporium herbarum* |
| Cla h 4 | RLA4_CLAHE | P42039 | 60S Acidic Ribosomal Protein P2 | *Cladosporium herbarum* |
| Cla h 5 | CLH5_CLAHE | P42059 | Minor Allergen Cla h 5 | *Cladosporium herbarum* |
| Cla h 6 | ENO_CLAHE | P42040 | Enolase | *Cladosporium herbarum* |
| Cla h 12 | RLA1_CLAHE | P50344 | 60S Acidic Ribosomal Protein P1 | *Cladosporium herbarum* |
| Cop c 2 | THIO_CAPCM | | | |
| Cor a 1 | MPAA_CORAV | Q08407 | Major Pollen Allergen Cor a 1, Isoforms 5, 6, 11 and 16 | *Corylus avellana* (European hazel) |
| Cup a 1 | MPA1_CUPAR | Q9SCG9 | Major Pollen Allergen Cup a 1 | *Cupressus arizonica* |
| Cry j 1 | SBP_CRYJA | P18632 | Sugi Basic Protein [Precursor] | *Cryptomeria japonica* (Japanese cedar) |
| Cry j 2 | MPA2_CRYJA | P43212 | Possible Polygalacturonase | *Cryptomeria japonica* (Japanese cedar) |
| Cyn d 12 | PROF_CYNDA | O04725 | Profilin | *Cynodon dactylon* (Bermuda grass) |
| Dac g 2 | MPG2_DACGL | Q41183 | Pollen Allergen Dac g 2 [Fragment] | *Dactylis glomerata* (Orchard grass) (Cocksfoot grass) |

TABLE 1-continued

| Allergen | SWISS-PROT Entry | SWISS-PROT Accession No. | Protein Name | Source |
|---|---|---|---|---|
| Dau c 1 | DAU1_DAUCA | O04298 | Major Allergen Dau c 1 | *Daucus carota* (Carrot) |
| Der f 1 | MMAL_DERFA | P16311 | Major Mite Fecal Allergen Der f 1 [Precursor] | *Dermatophagoides farinae* (House-dust mite) |
| Der f 2 | DEF2_DERFA | Q00855 | Mite Allergen Der f 2 [Precursor] | *Dermatophagoides ferinae* (House-dust mite) |
| Der f 3 | DEF3_DERFA | P49275 | Mite Allergen Der f 3 [Precursor] | *Dermatophagoides ferinae* (House-dust mite) |
| Der f 6 | DEF6_DERFA | P49276 | Mite Allergen Der f 6 [Fragment] | *Dermatophagoides ferinae* (House-dust mite) |
| Der f 7 | DEF7_DERFA | Q26456 | Mite Allergen Der f 7 [Precursor] | *Dermatophagoides ferinae* (House-dust mite) |
| Der m 1 | MMAL_DERMI | P16312 | Major Mite Fecal Allergen Der m 1 [Fragment] | *Dermatophagoides microceras* (House-dust mite) |
| Der p 1 | MMAL_DERPT | P08176 | Major Mite Fecal Allergen Der p 1 [Precursor] | *Dermatophagoides pteronyssinus* (House-dust mite) |
| Der p 2 | DER2_DERPT | P49278 | Mite Allergen Der p 2 [Precursor] | *Dermatophagoides pteronyssinus* (House-dust mite) |
| Der p 3 | DER3_DERPT | P39675 | Mite Allergen Der p 3 [Precursor] | *Dermatophagoides pteronyssinus* (House-dust mite) |
| Der p 4 | AMY_DERPT | P49274 | Alpha-Amylase [Fragment] | *Dermatophagoides pteronyssinus* (House-dust mite) |
| Der p 5 | DER5_DERPT | P14004 | Mite Allergen Der p 5 | *Dermatophagoides pteronyssinus* (House-dust mite) |
| Der p 6 | DER6_DERPT | P49277 | Mite Allergen Der p 6 [Fragment] | *Dermatophagoides pteronyssinus* (House-dust mite) |
| Der p 7 | DER7_DERPT | P49273 | Mite Allergen Der p 7 [Precursor] | *Dermatophagoides pteronyssinus* (House-dust mite) |
| Dol a 5 | VA5_DOLAR | Q05108 | Venom Allergen 5 | *Dolichovespula arenaria* (Yellow hornet) |
| Dol m 1 | PA11_DOLMA | Q06478 | Phospholipase A1 1 [Precursor] [Fragment] | *Dolichovespula maculata* (White-face hornet) (Bald-faced hornet) |
| Dol m 1 | PA12_DOLMA | P53357 | Phospholipase A1 2 | *Dolichovespula maculata* (White-face hornet) (Bald-faced hornet) |
| Dol m 2 | HUGA_DOLMA | P49371 | Hyaluronoglucosaminidase | *Dolichovespula maculata* (White-face hornet) (Bald-faced hornet) |
| Dol m 5 | VA52_DOLMA | P10736 | Venom Allergen 5.01 [Precursor] | *Dolichovespula maculata* (White-face hornet) (Bald-faced hornet) |
| Dol m 5 | VA53_DOLMA | P10737 | Venom Allergen 5.02 [Precursor] [Fragment] | *Dolichovespula maculata* (White-face hornet) (Bald-faced hornet) |
| Equ c 1 | ALL1_HORSE | Q95182 | Major Allergen Equ c 1 [Precursor] | *Equus caballus* (Horse) |
| Equ c 2 | AL21_HORSE | P81216 | Dander major Allergen Equ c 2.0101 [Fragment] | *Equus caballus* (Horse) |
| Equ c 2 | AL22_HORSE | P81217 | Dander Major Allergen Equ c 2.0102 [Fragment] | *Equus caballus* (Horse) |
| Eur m 1 | EUM1_EURMA | P25780 | Mite Group I Allergen Eur m 1 [Fragment] | *Euroglyphus maynei* (House-dust mite) |
| Fel d 1 | FELA_FELCA | P30438 | Major Allergen I Polypeptide Chain 1 Major Form [Precursor] | *Felis silvestris catus* (Cat) |

TABLE 1-continued

| Allergen | SWISS-PROT Entry | SWISS-PROT Accession No. | Protein Name | Source |
|---|---|---|---|---|
| Fel d 1 | FELB_FELCA | P30439 | Major Allergen I Polypeptide Chain 1 Minor Form [Precursor] | *Felis silvestris catus* (Cat) |
| Fel d 1 | FEL2_FELCA | P30440 | Major Allergen I Polypeptide Chain 2 [Precursor] | *Felis silvestris catus* (Cat) |
| Gad c 1 | PRVB_GADCA | P02622 | Parvalbumin Beta | *Gadus callarias* (Baltic cod) |
| Gal d 1 | IOVO_CHICK | P01005 | Ovomucoid [Precursor] | *Gallus gallus* (Chicken) |
| Gal d 2 | OVAL_CHICK | P01012 | Ovalbumin | *Gallus gallus* (Chicken) |
| Gal d 3 | TRFE_CHICK | P02789 | Ovotransferrin [Precursor] | *Gallus gallus* (Chicken) |
| Gal d 4 | LYC_CHICK | P00698 | Lysozyme C [Precursor] | *Gallus gallus* (Chicken) |
| Hel a 2 | PROF_HELAN | O81982 | Profilin | *Helianthus annuus* (Common sunflower) |
| Hev b 1 | REF_HEVBR | P15252 | Rubber Elongation Factor Protein | *Hevea brasiliensis* (Para rubber tree) |
| Hev b 5 | HEV5_HEVBR | Q39967 | Major Latex Allergen Hev b 5 | *Hevea brasiliensis* (Para rubber tree) |
| Hol l 1 | MPH1_HOLLA | P43216 | Major Pollen Allergen Hol l 1 [Precursor] | *Holcul lanatus* (Velvet grass) |
| Hor v 1 | IAA1_HORVU | P16968 | Alpha-amylase Inhibitor Bmai-1 [Precursor] [Fragment] | *Hordeum vulgare* (Barley) |
| Jun a 1 | MPA1_JUNAS | P81294 | Major Pollen Allergen Jun a 1 [Precursor] | *Juniperus ashei* (Ozark white cedar) |
| Jun a 3 | PRR3_JUNAS | P81295 | Pathogenesis-Related Protein [Precursor] | *Juniperus ashei* (Ozark white cedar) |
| Lep d 1 | LEP1_LEPDS | P80384 | Mite Allergen Lep d 1 [Precursor] | *Lepidoglyphus destructor* (Storage mite) |
| Lol p 1 | MPL1_LOLPR | P14946 | Pollen Allergen Lol p 1 [Precursor] | *Lolium perenne* (Perennial ryegrass) |
| Lol p 2 | MPL2_LOLPR | P14947 | Pollen Allergen Lol p 2-a | *Lolium perenne* (Perennial ryegrass) |
| Lol p 3 | MPL3_LOLPR | P14948 | Pollen Allergen Lol p 3 | *Lolium perenne* (Perennial ryegrass) |
| Lol p 5 | MP5A_LOLPR | Q40240 | Major Pollen Allergen Lol p 5a [Precursor] | *Lolium perenne* (Perennial ryegrass) |
| Lol p 5 | MP5B_LOLPR | Q40237 | Major Pollen Allergen Lol p 5b [Precursor] | *Lolium perenne* (Perennial ryegrass) |
| Mal d 1 | MAL1_MALDO | P43211 | Major Allergen Mal d 1 | *Malus domestica* (Apple) (*Malus sylvestris*) |
| Mer a 1 | PROF_MERAN | O49894 | Profilin | *Mercurialis annua* (Annual mercury) |
| Met e 1 | TPM1_METEN | Q25456 | Tropomyosin | *Metapenaeus ensis* (Greasyback shrimp) (Sand shrimp) |
| Mus m 1 | MUP6_MOUSE | P02762 | Major Urinary Protein 6 [Precursor] | *Mus musculus* (Mouse) |
| Myr p 1 | MYR1_MYRPI | Q07932 | Major Allergen Myr p 1 [Precursor] | *Myrmecia pilosula* (Bulldog ant) (Australian jumper ant) |
| Myr p 2 | MYR2_MYRPI | Q26464 | Allergen Myr p 2 [Precursor] | *Myrmecia pilosula* (Bulldog ant) (Australian jumper ant) |
| Ole e 1 | ALL1_OLEEU | P19963 | Major Pollen Allergen | *Olea europaea* (Common olive) |
| Ole e 4 | ALL4_OLEEU | P80741 | Major Pollen Allergen Ole e 4 [Fragments] | *Olea europaea* (Common olive) |
| Ole e 5 | SODC_OLEEU | P80740 | Superoxide Dismutase [CU-ZN] [Fragment] | *Olea europaea* (Common olive) |
| Ole e 7 | ALL7_OLEEU | P81430 | Pollen Allergen Ole e 7 [Fragment] | *Olea europaea* (Common olive) |
| Ory s 1 | MPO1_ORYSA | Q40638 | Major Pollen Allergen Ory s 1 [Precursor] | *Oryza sativa* (Rice) |
| Par j 1 | NL11_PARJU | P43217 | Probable Nonspecific Lipid-Transfer Protein [Fragment] | *Parietaria judaica* |
| Par j 1 | NL12_PARJU | O04404 | Probable Nonspecific Lipid-Transfer Protein 1 [Precursor] | *Parietaria judaica* |

TABLE 1-continued

| Allergen | SWISS-PROT Entry | SWISS-PROT Accession No. | Protein Name | Source |
|---|---|---|---|---|
| Par j 1 | NL13_PARJU | Q40905 | Probable Nonspecific Lipid-Transfer Protein 1 [Precursor] | *Parietaria judaica* |
| Par j 2 | NL21_PARJU | P55958 | Probable Nonspecific Lipid-Transfer Protein 2 [Precursor] | *Parietaria judaica* |
| Par j 2 | NL22_PARJU | O04403 | Probable Nonspecific Lipid-Transfer Protein 2 [Precursor] | *Parietaria judaica* |
| Pha a 1 | MPA1_PHAAQ | Q41260 | Major Pollen Allergen Pha a 1 [Precursor] | *Phalaris aquatica* |
| Pha a 5 | MP51_PHAAQ | P56164 | Major Pollen Allergen Pha a 5.1 [Precursor] | *Phalaris aquatica* |
| Pha a 5 | MP52_PHAAQ | P56165 | Major Pollen Allergen Pha a 5.2 [Precursor] | *Phalaris aquatica* |
| Pha a 5 | MP53_PHAAQ | P56166 | Major Pollen Allergen Pha a 5.3 [Precursor] | *Phalaris aquatica* |
| Pha a 5 | MP54_PHAAQ | P56167 | Major Pollen Allergen Pha a 5.4 [Fragment] | *Phalaris aquatica* |
| Phl p 1 | MPP1_PHLPR | P43213 | Pollen Allergen Phl p 1 [Precursor] | *Phleum pratense* (Common timothy) |
| Phl p 2 | MPP2_PHLPR | P43214 | Pollen Allergen Phl p 2 [Precursor] | *Phleum pratense* (Common timothy) |
| Phl p 5 | MP5A_PHLPR | Q40962 | Pollen Allergen Phl p 5a [Fragment] | *Phleum pratense* (Common timothy) |
| Phl p 5 | MP5B_PHLPR | Q40963 | Pollen Allergen Phl p 5b [Precursor] [Fragment] | *Phleum pratense* (Common timothy) |
| Phl p 6 | MPP6_PHLPR | P43215 | Pollen Allergen Phl p 6 [Precursor] | *Phleum pratense* (Common timothy) |
| Phl p 11 | PRO1_PHLPR | P35079 | Profilin 1 | *Phleum pratense* (Common timothy) |
| Phl p 11 | PRO2_PHLPR | O24650 | Profilin 2/4 | *Phleum pratense* (Common timothy) |
| Phl p 11 | PRO3_PHLPR | O24282 | Profilin 3 | *Phleum pratense* (Common timothy) |
| Poa p 9 | MP91_POAPR | P22284 | Pollen Allergen Kbg 31 [Precursor] | *Poa pratensis* (Kentucky bluegrass) |
| Poa p 9 | MP92_POAPR | P22285 | Pollen Allergen Kbg 41 [Precursor] | *Poa pratensis* (Kentucky bluegrass) |
| Poa p 9 | MP93_POAPR | P22286 | Pollen Allergen Kbg 60 [Precursor] | *Poa pratensis* (Kentucky bluegrass) |
| Pol a 5 | VA5_POLAN | Q05109 | Venom Allergen 5 [Precursor] [Fragment] | *Polistes annularis* (Paper wasp) |
| Pol d 5 | VA5_POLDO | P81656 | Venom Allergen 5 | *Polistes dominulus* (European paper wasp) |
| Pol e 5 | VA5_POLEX | P35759 | Venom Allergen 5 | *Polistes exclamans* (Paper wasp) |
| Pol f 5 | VA5_POLFU | P35780 | Venom Allergen 5 | *Polistes fuscatus* (Paper wasp) |
| Pru a 1 | PRU1_PRUAV | O24248 | Major Allergen Pru a 1 | *Prunus avium* (Cherry) |
| Rat n 1 | MUP_RAT | P02761 | Major Urinary Protein [Precursor] | *Rattus norvegicus* (Rat) |
| Sol i 2 | VA2_SOLIN | P35775 | Venom Allergen II [Precursor] | *Solenopsis invicta* (Red imported fire ant) |
| Sol i 3 | VA3_SOLIN | P35778 | Venom Allergen III | *Solenopsis invicta* (Red imported fire ant) |
| Sol i 4 | VA4_SOLIN | P35777 | Venom Allergen IV | *Solenopsis invicta* (Red imported fire ant) |
| Sol r 2 | VA2_SOLRI | P35776 | Venom Allergen II | *Solenopsis richteri* (Black imported fire ant) |
| Sol r 3 | VA3_SOLRI | P35779 | Venom Allergen III | *Solenopsis richteri* (Black imported fire ant) |
| Ves c 5 | VA51_VESCR | P35781 | Venom Allergen 5.01 | *Vespa crabro* (European hornet) |
| Ves c 5 | VA52_VESCR | P35782 | Venom Allergen 5.02 | *Vespa crabro* (European hornet) |
| Ves f 5 | VA5_VESFL | P35783 | Venom Allergen 5 | *Vespula flavopilosa* (Yellow jacket) (Wasp) |
| Ves g 5 | VA5_VESGE | P35784 | Venom Allergen 5 | *Vespula germanica* (Yellow jacket) (Wasp) |

TABLE 1-continued

| Allergen | SWISS-PROT Entry | SWISS-PROT Accession No. | Protein Name | Source |
|---|---|---|---|---|
| Ves m 1 | PA1_VESMC | P51528 | Phospholipase A1 | *Vespula maculifrons* (Eastern yellow jacket) (Wasp) |
| Ves m 5 | VA5_VESMC | P35760 | Venom Allergen 5 | *Vespula maculifrons* (Eastern yellow jacket) (Wasp) |
| Ves p 5 | VA5_VESPE | P35785 | Venom Allergen 5 | *Vespula pensylvanica* (Western yellow jacket) (Wasp) |
| Ves s 5 | VA5_VESSQ | P35786 | Venom Allergen 5 | *Vespula squamosa* (Southern yellow jacket) (Wasp) |
| Ves v 1 | PA1_VESVU | P49369 | Phospholipase A1 [Precursor] | *Vespula vulgaris* (Yellow jacket) (Wasp) |
| Ves v 2 | HUGA_VESVU | P49370 | Hyaluronoglucosaminidase | *Vespula vulgaris* (Yellow jacket) (Wasp) |
| Ves v 5 | VA5_VESVU | Q05110 | Venom Allergen 5 [Precursor] | *Vespula vulgaris* (Yellow jacket) (Wasp) |
| Ves vi 5 | VA5_VESVI | P35787 | Venom Allergen 5 | *Vespula vidua* (Yellow jacket) (Wasp) |
| Vesp m 5 | VA5_VESMA | P81657 | Venom Allergen 5 | *Vespa mandarinia* (Hornet) |
| Zea m 1 | MPZ1_MAIZE | Q07154 | Pollen Allergen Zea m 1 | *Zea mays* (Maize) |

In other embodiments, the amino acid sequence of the second polypeptide of the fusion molecule is defined with reference to an autoantigen sequence. Examples of autoantigen sequences are listed in Table 2 below. Portions of the autoantigens listed in Table 2 are also suitable for use in the fusion polypeptides, wherein the portion retains at least one autoantigen epitope, and retains the ability to specifically bind the autoantibody or autoreactive T-cell receptor. For example, useful portions of the multiple sclerosis autoantigens myelin-basic-protein (amino acids 83-99), proteolipid protein (amino acids 139-151) and myelin oligodendrocyte glycoprotein (amino acids 92-106) are known, where the portions retain at least one autoantigenic epitope.

TABLE 2

| Auto-antigen | Autoimmune Disease(s) | Reference and/or GenBank Accession No. |
|---|---|---|
| acetylcholine receptor (AChR) | myasthenia gravis | Patrick and Lindstrom, Science 180: 871-872 (1973); Lindstrom et al., Neurology 26: 1054-1059 (1976); Protti et al., Immunol. Today, 15(1): 41-42 (1994); Q04844; P02708; ACHUA1; AAD14247 |
| gravin | | Nauert et al., Curr. Biol., 7(1): 52-62 (1997); Q02952; AAB58938 |
| titin (connectin) | | Gautel et al., Neurology 43: 1581-1585 (1993); Yamamoto et al., Arch. Neurol., 58(6): 869-870 (2001); AAB28119 |
| neuronal voltage-gated calcium channel | Lambert-Eaton myasthenic syndrome | Rosenfeld et al., Ann. Neurol., 33(1): 113-120 (1993); A48895 |
| CNS myelin-basic-protein (MBP), $MBP_{83-99}$ epitope | multiple sclerosis | Warren et al., Proc. Natl. Acad. Sci. USA 92: 11061-11065 [1995]; Wucherpfennig et al., J. Clin. Invest., 100(5): 1114-1122 [1997]; Critchfield et al., Science 263: 1139-1143 [1994]; Racke et al., Ann. Neurol., 39(1): 46-56 [1996]; XP_040888; AAH08749; P02686 |
| proteolipid protein (PLP), $PLP_{139-151}$ epitope $PLP_{178-191}$ epitope | | XP_010407 |
| myelin oligodendrocyte glycoprotein (MOG), $MOG_{92-106}$ epitope | | XP_041592 |
| αβ-crystallin | | Van Noort et al., Nature 375: 798 (1995); Van Sechel et al., J. Immunol., 162: 129-135 (1999); CYHUAB |
| myelin-associated glycoprotein (MAG), Po glycoprotein and PMP22 | | Latov, Ann. Neurol., 37(Suppl. 1): S32-S42 (1995); Griffin, Prog. Brain Res., 101: 313-323 (1994); Rose and MacKay (Eds.), The Autoimmune Diseases, Third Edition, Academic Press, p. 586-602 [1998]; XP_012878; P20916 |

TABLE 2-continued

| Auto-antigen | Autoimmune Disease(s) | Reference and/or GenBank Accession No. |
|---|---|---|
| 2',3'-cyclic nucleotide 3'-phosphohydrolase (CNPase) | | P09543; JC1517 |
| glutamic acid decarboxylase (GAD), and various isoforms (e.g., 65 and 67 kDa isoforms) | type-I (insulin dependent) diabetes mellitus, also Stiff-Man Syndrome (GAD) and other diseases (GAD) | Yoon et al., Science 284: 1183-1187 [1999]; Nepom et al., Proc. Natl. Acad. Sci. USA 98(4): 1763-1768 [2001]; Lernmark, J. Intern. Med., 240: 259-277 [1996]; B41935; A41292; P18088; Q05329 |
| insulin | | Wong et al., Nature Med., 5: 1026-1031 [1999]; Castano et al., Diabetes 42: 1202-1209 (1993) |
| 64 kD islet cell antigen/ tyrosine phosphatase-like islet cell antigen-2 (IA-2, also termed ICA512) | | Rabin et al., Diabetes 41: 183-186 (1992); Rabin et al., J. Immunol., 152: 3183-3187 (1994); Lan et al., DNA Cell Biol., 13: 505-514 (1994) |
| phogrin (IA-2β) | | Wasmeier and Hutton, J. Biol. Chem., 271: 18161-18170 (1996); Q92932 |
| type II collagen | rheumatoid arthritis | Cook et al., J. Rheumatol., 21: 1186-1191 (1994); and Terato et al., Arthritis Rheumatol., 33: 1493-1500 (1990) |
| human cartilage gp39 (HCgp39) | | P29965; XP_042961 |
| gp130-RAPS | | P40189; BAA78112 |
| scl-70 antigen/topoisomerase-I | scleroderma (systemic sclerosis), various connective tissue diseases | Douvas et al., J. Biol. Chem., 254: 10514-10522 (1979); Shero et al., Science 231: 737-740 (1986); P11387 |
| topoisomerase II (α/β) | | Meliconi et al., Clin. Exp. Immunol., 76(2): 184-189(1989); XP_008649; NP_001059; Q02880 |
| type I collagen | | Riente et al., Clin. Exp. Immunol., 102(2): 354-359 (1995); XP_037912 |
| fibrillarin, U3-small nuclear protein (snoRNP) | | Arnett et al., Arthritis Rheum., 39: 151-160 (1996) |
| Jo-1 antigen/aminoacyl histidyl-tRNA synthetase | polymyositis, dermatomyositis, interstitial lung disease, Raynaud's phenomenon, also scleroderma (PM-scl) | Mathews and Bernstein, Nature 304: 177-179 (1983); Bernstein, Bailliere's Clin. Neurol., 2: 599-616 (1993); Targoff, J. Immunol., 144(5): 1737-1743 (1990); Targoff, J. Invest. Dermatol., 100: 116S-123S (1995); Rider and Miller, Clin. Diag. Lab. Immunol., 2: 1-9 (1995); Targoff, J. Invest. Dermatol., 100: 116S-123S (1995); von Muhlen and Tan, Semin. Arthritis Rheum., 24: 323-358 (1995); Targoff et al., J. Clin. Invest., 84: 162-172 (1989) |
| PL-7 antigen/threonyl tRNA synthetase | | |
| PL-12 antigen/alanyl tRNA synthetase | | |
| EJ antigen/glycyl-tRNA synthetase | | |
| OJ antigen/NJ antigen isoleucyl-tRNA synthetase | | |
| signal recognition particle (SRP) | | |
| Mi-2 helicase | | |
| PM-scl proteins (75 kDa, 100 kDa) | | |
| KJ antigen | | |
| Fer antigen/ elongation fractor 1α | | |
| Mas antigen/ tRNA$^{Ser}$ | | |
| type IV collagen α3 chain | Goodpasture syndrome | Hellmark et al., Kidney Int., 46: 823-829 (1994); Q01955 |
| Smith (Sm) antigens and snRNP's, including snRNPs D1, D2, D3, B, B', B3 (N), E, F, and G, as found in RNP complexes U1, U2, U4/6, and U5. | systemic lupus erythematosus, mixed connective tissue disease (MCTD), progressive systemic sclerosis, rheumatoid arthritis, discoid lupus erythematosus, Sjögren's syndrome | Lerner and Steitz, Proc. Natl. Acad. Sci. USA 76: 5495-5499 (1979); Reuter et al., Eur. J. Immunol., 20: 437-440 (1990); Petersson et al., J. Biol. Chem., 259: 5907-5914 (1984) |
| nRNP U1-snRNP complex, including subunits U1-70 kD, A and C. | | Klein et al., Clin. Exp. Rheumatol., 15: 549-560 (1997) |
| deoxyribonucleic acid (DNA), double-stranded B-form deoxyribonucleic acid (DNA), denatured/single-stranded | systemic lupus erythematosus | Pisetsky, Curr. Top. Microl. Immunol., 247: 143-155 (2000); Radic et al., Crit. Rev. Immunol., 19(2): 117-126 (1999) |
| Cyclin A | autoimmune hepatic disease, and other diseases | Strassburg et al., Gastroenterology 111: 1582-1592 (1996); Strassburg et al., J. Hepatol., 25(6): 859-866 (1996) |
| Ro (SS-A) antigens 52 kDa 60 kDa | Sjögren's syndrome, systemic and cutaneous lupus erythematosis, rheumatoid arthritis, neonatal lupus syndrome, polymyositis, progressive systemic sclerosis, primary biliary cirrhosis | Tan, Adv. Immunol., 44: 93-(1989); McCauliffe and Sontheimer, J. Invest. Dermatol., 100: 73S-79S (1993); Wolin and Steitz, Proc. Natl. Acad. Sci. USA 81: 1996-2000 (1984); Slobbe et al., Ann. Med. Interne., 142: 592-600 (1991); AAB87094; U01882; P10155 |

TABLE 2-continued

| Auto-antigen | Autoimmune Disease(s) | Reference and/or GenBank Accession No. |
|---|---|---|
| La (SS-B) antigen | Sjögren's syndrome, neonatal lupus syndrome, systemic lupus erythematosis | Manoussakis et al., Scan. J. Rheumatol., 61: 89-92 (1986); Harley et al., Arthritis Rheum., 29: 196-206 (1986); Slobbe et al., Ann. Med. Interne., 142: 592-600 (1991); P05455 |
| proteinase-3 (serine proteinase)/cytoplasmic neutrophil antigen (cANCA)/ myeloblastin | Wegener's granulomatosis, systemic vasculitis, microscopic polyangiitis, idiopathic crescentic glomerulonephritis, Churg-Strauss syndrome, polyarteritis nodosa | Ledemann et al., J. Exp. Med., 171: 357-362 (1990); Jenne et al., Nature 346: 520 (1990); Gupta et al., Blood 76: 2162 (1990); P24158 |
| myeloperoxidase/nuclear or perinuclear neutrophil antigen (pANCA) | systemic lupus erythrematosus/ antiphospholipid syndrome (APS)/thrombocytopenia/ recurrent thromboembolic phenomenon | Lee et al., Clin. Exp. Immunol., 79: 41-46 (1990); Cohen Tervaert et al., Arthr. Rheum., 33: 1264-1272 (1990); Gueirard et al., J. Autoimmun., 4: 517-527 (1991); Ulmer et al., Clin. Nephrol., 37: 161-168 (1992); P05164 |
| $\beta_2$-glycoprotein-1 (aka apolipoprotein H) cardiolipin, phosphatidylcholine, and various anionic phospholipids | antiphospholipid/cofactor syndromes, autoimmune gastritis/type A chronic atrophic gastritis/pernicious anaemia | McNeil et al., Proc. Natl. Acad. Sci. USA 87: 4120-4124 (1990) Alarcòn-Segovia and Cabral, Lupus 5: 364-367 (1996); and Alarcòn-Segovia and Cabral, J. Rheumatol., 23: 1319-1322 (1996) |
| parietal cell antigen; $H^+/K^-$ ATPase gastric proton pump $\alpha$ & $\beta$ subunits | autoimmune gastritis, type A chronic atrophic gastritis, pernicious anaemia | Karlsson et al., J. Clin. Invest., 81(2): 475-479 (1988); Burman et al., Gastroenterology 96(6): 1434-1438 (1989); Toh et al., Proc. Natl. Acad. Sci. USA 87(16): 6418-6422 (1990) |
| thyroglobulin (TG); $TG_{1149-1250}$ | Hashimoto's thyroidosis, primary myxedema, subacute thyroiditis | Malthiery and Lissitzky, Eur. J. Biochem., 105: 491-498 (1987); Henry et al., Eur. J. Immunol., 22: 315-319 (1992); Prentice et al., J. Clin. Endocrinol. Metab., 80: 977-986 (1995) |
| thyroid peroxidase (TPO); $TPO_{590-675}$ and $TPO_{651-750}$ | | McLachlan and Rapoport, Endocr. Rev., 13: 192-206 (1992); McLachlan and Rapoport, Clin. Exp. Immunol., 101: 200-206 (1995); Tonacchera et al., Eur. J. Endocrinol., 132: 53-61 (1995) |
| thyroid-stimulating hormone receptor (TSH-R, also termed thyrotropin) | Graves' disease (thyrotoxicosis) and myxedema, hyperactive thyroid disease, Hashimoto's thyroiditis | Weetman and McGregor, Endocr. Rev., 15: 788-830 (1994) |
| desmosomal proteins; desmoglein-1 desmoglein-3 | pemphigus blistering disorders, and other cutaneous diseases | Korman et al., N. Engl. Jour. Med., 321: 631-635 (1989); Amagi et al., Cell 67: 869-877 (1991); Koulu et al., J. Exp. Med., 160: 1509-1518 (1984); Stanley et al., J. Immunol., 136: 1227-1230 (1986); Cozzani et al., Eur. J. Dermatol., 10(4): 255-261 (2000) |
| hemidesmosome proteins BP180 (also known as BPAG2 and type XVII collagen) and BP230 (BPAG1) | | Diaz et al., J. Clin. Invest., 86: 1088-1094 (1990); Giudice et al., J. Invest. Dermatol., 99: 243-250 (1992); Stanley et al., J. Clin. Invest., 82: 1864-1870 (1988) |
| type VII collagen | | Gammon et al., J. Invest. Dermatol., 84: 472-476 (1985) |
| mitochondrial pyruvate dehydrogenase complex (PDC) E1α decarboxylase mitochondrial E1β decarboxylase mitochondrial PDC-E2 acetyltransferase mitochondrial protein X mitochondrial branched chain 2-oxo acid dehydrogenase (BCOADC) E2 subunit PDC-E2 (mitochondrial pyruvate dehydrogenase dehydrolipoamide acetyltransferase) 2-oxoglutarate dehydrogenase (OGDC); E2 succinly transferase | primary biliary cirrhosis, autoimmune hepatitis, systemic sclerosis | Gershwin et al., J. Immunol., 138: 3525-3531 (1987); Moteki et al., Hepatology (Baltimore), 23: 436-444 (1996); Surh et al., Hepatology (Baltimore), 9: 63-68 (1989); and Yeaman et al., Lancet 1: 1067-1070 (1988); Jones et al., J. Clin. Pathol., 53(11): 813-821 (2000); Mackay et al., Immunol. Rev., 174: 226-237 (2000) |
| chromosomal centromere proteins CENP-A, B, C and F | systemic sclerosis | Earnshaw and Rothfield, Chromosoma 91(3-4): 313-321 (1985) |
| coilin/p80 | autoimmune dermatological disorders, and other diseases | Andrade et al., J. Exp. Med., 173(6): 1407-1419 (1991); Muro, J. Dermatol. Sci., 25(3): 171-178 (2001); S50113 |

TABLE 2-continued

| Auto-antigen | Autoimmune Disease(s) | Reference and/or GenBank Accession No. |
|---|---|---|
| HMG proteins<br>HMG-1<br>HMG-2<br>HMG-14<br>HMG-17 | systemic lupus erythematosus, drug induced lupus, scleroderma, autoimmune hepatitis | Bustin et al., Science 215(4537): 1245-1247 (1982); Vlachoyiannopoulos et al., J. Autoimmun., 7(2): 193-201 (1994); Somajima et al., Gut 44(6): 867-873 (1999); Ayer et al., Arthritis Rheum., 37(1): 98-103 (1994) |
| Histone proteins H1, H2A, H2B, H3 and H4 | systemic lupus erythrematosus, drug induced lupus, rheumatoid arthritis, and other diseases | Shen et al., Clin. Rev. Allergy Immunol., 16(3): 321-334 (1998); Burlingame and Rubin, Mol. Biol. Rep., 23(3-4): 159-166 (1996) |
| Ku antigen (p70/p80) and DNA-PK catayltic subunit | systemic sclerosis, systemic lupus erythrematosus, mixed connective tissue diseases, dermatomyositis, and other diseases | Yaneva et al., Clin. Exp. Immunol., 76: 366-372 (1989); Mimori et al., J. Biol. Chem., 261(5): 2274-2278 (1986); Tuteja and Tuteja, Crit. Rev. Biochem. Mol. Biol., 35(1): 1-33 (2000); Satoh et al., Clin. Exp. Immunol., 105(3): 460-467 (1996) |
| NOR-90/hUBF | systemic sclerosis | Dick et al., J. Rheumatol., 22: 67-72 (1995); Rodriguez-Sanchez et al., J. Immunol., 139(8): 2579-2584 (1987) |
| Proliferating cell nuclear antigen (PCNA) | systemic lupus erythrematosus, and other diseases | Takeuchi et al., Mol. Biol. Rep., 23(3-4): 243-246 (1996); Fritzler et al., Arthritis Rheum., 26(2): 140-145 (1983); P12004 |
| ribosomal RNP proteins ("P-antigens") P0, P1 and P2 | systemic lupus erythrematosus | Elkon et al., J. Exp. Med., 162(2): 459-471 (1985); Bonfa et al., J. Immunol., 140(10): 3434-3437 (1988) |
| Ra33/hnRNP A2 | rheumatoid arthritis | Hassfeld et al., Arthritis Rheum., 32(12): 1515-1520 (1989); Steiner et al., J. Clin. Invest., 90(3): 1061-1066 (1992) |
| SP-100 | undifferentiated connective tissue diseases (UCTD), Sjogren's syndrome, primary biliary cirrhosis and other disorders | Szostecki et al., Clin. Exp. Immunol., 68(1): 108-116 (1987) |
| S-antigen/interphotoreceptor retinoid binding protein (IRBP) | uveitis/uveoretinitis | Dua et al., Curr. Eye Res., 11: 59-65 (1992) |
| annexin XI (56K autoantigen) | rheumatiod arthritis, systemic lupus erythematosus, Sjögren's syndrome | Misaki et al., J. Biol. Chem., 269(6): 4240-4246 (1994) |
| hair follicle antigens | alopecia (e.g., alopecia areata) | McElwee et al., Exp. Dermatol., 8(5): 371-379 (1999) |
| human tropomyosin isoform 5 (hTM5) | ulcerative colitis | Das et al., J. Immunol., 150(6): 2487-2493 (1993) |
| cardiac myosin | myocarditis and cardiomyopathy and related diseases | Caforia et al., Circulation 85: 1734-1742 (1992); Neumann et al., J. Am. Coll. Cardiol., 16: 839-846 (1990) |
| laminin | | Wolff et al., Am. Heart Jour., 117: 1303-1309 (1989) |
| $\beta_1$-adrenergic receptors | | Limas et al., Circ. Res., 64: 97-103 (1989) |
| mitochondrial adenine nucleotide translocator (ANT) | | Schultheiss et al., Ann. NY Acad. Sci., 488: 44-64 (1986) |
| mitochondrial branched-chain ketodehydrogenase (BCKD) | | Ansari et al., J. Immunol., 153(10): 4754-4765 (1994) |
| eukaryotic elongation factor 1A-1 (eEF1A-1) | Felty's syndrome/autoimmune neutropenia | Ditzel et al., Proc. Natl. Acad. Sci. USA 97(16): 9234-9239 [2000] |
| glycoprotein gp70 (viral antigen) | systemic lupus erythematosus | Haywood et al., J. Immunol., 167(3): 1728-1733 (2001) |
| early endosome antigen-1 (EEA1) | subacute systemic lupus erythematosus | Mu et al., J. Biol. Chem., 270(22): 13503-13511 (1995); Stenmark et al., J. Biol. Chem., 271(39): 24048-24054 (1996) |
| 21-hydroxylase | Addison's Disease, types I and II autoimmune polyglandular syndrome (APS) | Winqvist, Lancet 339: 1559-1562 (1992); Bednarek et al., FEBS Lett., 309: 51-55 (1992) |
| calcium sensing receptor (Ca-SR) | hypoparathyroidism | Brown et al., Nature 366: 575-580 (1993); Li et al., J. Clin. Invest., 97: 910-914 (1996) |
| tyrosinase | vitiligo | Song et al., Lancet 344: 1049-1052 (1994) |
| tissue transgluaminase | celiac disease, gluen-sensitive enteropathy | Dieterich et al., Nat. Med., 3(7): 797-801 (1997); and Schuppan et al., Ann. NY Acad. Sci., 859: 121-126 (1998) |
| keratin proteins | inflammatory arthritis/rheumatoid arthritis | Borg, Semin. Arthritis Rheum., 27(3): 186-195 (1997) |
| poly (ADP-ribose) polymerase (PARP) | systemic lupus erythematosus, Sjogren's syndrome, and other diseases | Muller et al., Clin. Immunol. Immunopathol., 73(2): 187-196 (1994); Yamanaka et al., J. Clin. Invest., 83(1): 180-186 (1989) |
| nucleolar proteins B23/numatrin | systemic lupus erythematosus, and other diseases | Li et al., Arthritis Rheum., 32(9): 1165-1169 (1989); Zhang et al., Biochem. Biophys. Res. Commun., 164: 176-184 (1989); AAA36385 |

TABLE 2-continued

| Auto-antigen | Autoimmune Disease(s) | Reference and/or GenBank Accession No. |
|---|---|---|
| erythrocyte surface antigens/ glycophorins | autoimmune hemolytic anemia | Barker and Elson, Vet. Immunol. Immunopathol., 47(3-4): 225-238 (1995) |
| RNA polymerase I subunits RNA polymerase II subunits RNA polymerase III subunits Th/To (7-2 RNP; also known as RNase MRP) | systemic sclerosis/scleroderma, and other diseases | Hirakata et al., J. Clin. Invest., 91: 2665-2672 (1993); and Kuwana et al., J. Clin. Invest., 91: 1399-1404 (1993) Gold et al., Science 245(4924): 1377-1380 (1989); and Okano and Medsger, Arthritis Rheum., 33(12): 1822-1828 (1990) |
| nuclear mitotic apparatus proteins (NuMA proteins) | various connective tissue diseases | Andrade et al., Arthritis Rheum., 39(10): 1643-1653 (1996); Price et al., Arthritis Rheum., 27(7): 774-779 (1984) |
| nuclear lamins A, B and C | various hepatic and connective tissue autoimmune diseases, and other diseases | Hill et al., Aust. NZ J. Med., 26(2): 162-166 (1996); Lassoued et al., Ann. Intern. Med., 108(6): 829-833 (1988) |
| 210-kDa glycoprotein (gp210) | primary biliary cirrhosis | Nesher et al., Semin. Arthritis Rheum., 30(5): 313-320 (2001); Courvalin and Worman, Semin. Liver Dis., 17(1): 79-90 (1997) |
| pericentriolar material protein-1 (PCM-1) | scleroderma, and possibly other diseases | Balczon et al., J. Cell Biol., 124(5): 783-793 (1994); Mack et al., Arthritis Rheum., 41(3): 551-558 (1998) |
| platelet surface antigens/ glycoproteins IIb/IIIa and Ib/IX | autoimmune thrombocytopenia purpura | McMillan, Transfus. Med. Rev., 4: 136-143 (1990) |
| golgins (e.g., 95 and 160-kDa species) | various | Fritzler et al., J. Exp. Med., 178(1): 49-62 (1993) |
| F-actin | autoimmune hepatitis and primary biliary cirrhosis (UGT-1 and mitochondrial enzymes) | Czaja et al., Hepatology (Baltimore) 24: 1068-1073 (1996) |
| cytochrome P-450 superfamily proteins, most specifically 2D6; epitopes: $2D6_{257-269}$, $2D6_{321-351}$, $2D6_{373-389}$, and $2D6_{419-429}$. Also, P-450 proteins 1A2, 2B, 2C9, 2C11, 2E, 3A1, c21, scc, and c17a. | | Gueguen et al., Biochem, Biophys. Res. Commun., 159: 542-547 (1989); Manns et al., J. Clin. Invest., 83: 1066-1072 (1989); Zanger et al., Proc. Natl. Acad. Sci. USA 85: 8256-8260 (1988); Rose and MacKay (Eds.), The Autoimmune Diseases, Third Edition, Academic Press, Ch.26 "Autoimmune Diseases: The Liver," p.511-544 [1998] |
| UDP-glucuronosyltransferase family proteins (UGT-1 and UGT-2) | | Strassburg et al., Gastroenterology 111: 1582-1592 (1996) |
| asialoglycoprotein receptor (ASGP-R) | | Treichel et al., Hepatology (Baltimore) 11: 606-612 (1990) |
| amphiphysin | Stiff-Man syndrome | David et al., FEBS Lett., 351: 73-79 (1994) |
| glutamate receptor Glu R3 | Rasmussen's encephalitis | Rogers et al., Science 265: 648-651 (1994) |
| human gangliosides, especially $GM_1$, and also GD1a, N-acetylgalactosaminyl-GD1a, GD1b, GQb1, LM1, GT1b and asialo-$GM_1$. sulphatide (3'-sulphogalactosylceramide) | Guillain-Barrè Syndrome, and related neuronal syndromes (e.g., Miller-Fisher Syndrome); and autoimmune diabetes (sulphatide) | reviewed in Hartung et al., Muscle Nerve 18: 137-153 (1995) and Rose and MacKay (Eds.), The Autoimmune Diseases, Third Edition, Academic Press, p. 586-602 [1998] |

It is not intended that useful autoantigen sequences be limited to those sequences provided in Table 2, as methods for the identification of additional autoantigens are known in the art, e.g., SEREX techniques (serological identification of antigens by recombinant expression cloning), where expression libraries are screened using autoimmune sera probes (Bachmann et al., Cell 60:85-93 [1990]; and Pietromonaco et al., Proc. Natl. Acad. Sci. USA 87:1811-1815 [1990]; Folgori et al., EMBO J., 13:2236-2243 [1994]). Similarly, it is not intended that the autoimmune diseases that can be treated using the compositions and methods of the invention be limited to the diseases listed in Table 2, as additional diseases which have autoimmune etiologies will be identified in the future.

In some embodiments of the invention, the first polypeptide sequence present in the fusion molecule may comprise a sequence encoded by a nucleic acid hybridizing under stringent conditions to the complement of the coding sequence of a native γhinge-CHγ2-CHγ3 sequence, preferably the γhinge-CHγ2-CHγ3 coding sequence from within SEQ ID NO: 1, or with the coding sequence of another immunoglobulin heavy chain constant region sequence required for IgG binding.

When the first polypeptide sequence binds specifically to an ITIM-containing receptor expressed on mast cells, basophils or B cells, it is preferably encoded by nucleic acid hybridizing under stringent conditions to the complement of the coding sequence of a native ligand of that receptor.

Similarly, the second polypeptide sequence present in the fusion molecules of the invention may comprise a sequence encoded by nucleic acid hybridizing under stringent conditions to the complement of the coding sequence of a native CHϵ2-CHϵ3-CHϵ4 sequence, preferably the CHϵ2-CHϵ3-CHϵ4 coding sequence from within SEQ ID NO: 4, or to the complement of the coding sequence of a native allergen or autoantigen, such as those listed in Tables 1 and 2.

Whenever the first and/or second polypeptide sequence included in the fusion molecules of the invention is an amino acid variant of a native immunoglobulin constant region sequence, it is required to retain the ability to bind to the corresponding native receptor, such as a native IgG inhibitory receptor (e.g. FcγRIIb) and a native high-affinity IgE receptor (e.g. FcεRI) or native low-affinity IgE receptor (FcεRII, CD23), respectively. As discussed above, the receptor binding domains within the native IgG and IgE heavy chain constant region sequences have been identified. Based on this knowledge, the amino acid sequence variants may be designed to retain the native amino acid residues essential for receptor binding, or to perform only conservative amino acid alterations (e.g. substitutions) at such residues.

In making amino acid sequence variants that retain the required binding properties of the corresponding native sequences, the hydropathic index of amino acids may be considered. For example, it is known that certain amino acids may be substituted for other amino acids having a similar hydropathic index or score without significant change in biological activity. Thus, isoleucine, which has a hydrophatic index of +4.5, can generally be substituted for valine (+4.2) or leucine (+3.8), without significant impact on the biological activity of the polypeptide in which the substitution is made. Similarly, usually lysine (−3.9) can be substituted for arginine (−4.5), without the expectation of any significant change in the biological properties of the underlying polypeptide.

Other considerations for choosing amino acid substitutions include the similarity of the side-chain substituents, for example, size, electrophilic character, charge in various amino acids. In general, alanine, glycine and serine; arginine and lysine; glutamate and aspartate; serine and threonine; and valine, leucine and isoleucine are interchangeable, without the expectation of any significant change in biological properties. Such substitutions are generally referred to as conservative amino acid substitutions, and, as noted above, are the preferred type of substitutions within the polypeptides of the present invention.

Alternatively or in addition, the amino acid alterations may serve to enhance the receptor binding properties of the fusion molecules of the invention. Variants with improved receptor binding and, as a result, superior biological properties can be readily designed using standard mutagenesis techniques, such as alanine-scanning mutagenesis, PCR mutagenesis or other mutagenesis techniques, coupled with receptor binding assays, such as the assay discussed below or described in the Example.

In a preferred embodiment, the fusion molecules of the present invention comprise a first polypeptide sequence including functionally active hinge, CH2 and CH3 domains of the constant region of an $IgG_1$ heavy chain (γhinge-CHγ2-CHγ3 sequence) linked at its C-terminus to the N-terminus of a second polypeptide including functionally active CH2, CH3 and CH4 domains of the constant region of an IgE heavy chain (CHϵ2-CHϵ3-CHϵ4 sequence). In a particularly preferred embodiment, the first polypeptide sequence is composed of functionally active hinge, CH2 and CH3 regions of a native human $IgG_1$ heavy chain, linked at its C-terminus to the N-terminus of a second polypeptide composed of functionally active CH2, CH3 and CH4 domains of a native human IgE heavy chain constant region.

While it is preferred to fuse the IgG heavy chain constant region sequence (or a homologous sequence) C-terminally to the N-terminus of the IgE heavy chain constant region sequence (or a homologous sequence), fusion molecules in which the IgE heavy chain constant region sequence (or a homologous sequence) is fused C-terminally to the N-terminus of the IgG heavy chain constant region sequence (or a homologous sequence) are also within the scope of the invention. The fusion molecules may also comprise repeats of identical or different IgG and/or IgE heavy chain constant region sequences. For example, two repeats of IgG heavy chain constant region sequences, each including an IgG inhibitory receptor-binding domain, can be followed by IgE heavy chain constant region sequences (GGE structure), or two repeats of identical or different IgG heavy chain constant region sequences may flank an IgE heavy chain constant region sequence (GEG structure), etc. Fusion molecules comprising more than one binding sequence for a target receptor (e.g. an FcγRIIb receptor) are expected to have superior biological, e.g. anti-allergic properties.

The same considerations apply to the structure of fusion molecules where the second polypeptide sequence comprises, is or is derived from an allergen or autoantigen protein. Such molecules may also include repeats of the IgG heavy chain constant region sequences, fused to either or both sides of the allergen sequence.

Similarly, molecules in which the first polypeptide sequence binds to a different inhibitory receptor expressed on mast cells and/or basophils, e.g. an ITIM-containing inhibitory receptor functionally connected to a second polypeptide sequence binding directly or indirectly to an IgE receptor, e.g. FcϵRI, may contain multiple repeats of the inhibitory receptor binding regions and/or the IgE binding regions.

In all embodiments, the two polypeptide sequences are functionally connected, which means that they retain the ability to bind to the respective native receptors, such as a native IgG inhibitory receptor, e.g. a low-affinity FcγRIIb receptor, and to a native high-affinity IgE receptor, e.g. FcϵRI or low-affinity IgE receptor, as desired. As a result, the fusion molecules, comprising the first and second polypeptide sequences functionally connected to each other, are capable of cross-linking the respective native receptors, such as FcγRIIb and FcϵRI or FcγRIIb and FcϵRII. In order to achieve a functional connection between the two binding sequences within the fusion molecules of the invention, it is preferred that they retain the ability to bind to the corresponding receptor with a binding affinity similar to that of a native immunoglobulin ligand of that receptor.

The fusion molecules of the present invention are typically produced and act as homodimers or heterodimers, comprising two of the fusion molecules hereinabove described covalently linked to each other. The covalent attachment is preferably achieved via one or more disulfide bonds. For example, the prototype protein designated GE2 is produced as a homodimer composed of the two γhinge-CHγ2-CHγ3-15aa linker-CHϵ2-CHϵ3-CHϵ4 chains connected to each other by interchain disulfide bonds, to provide an immunoglobulin-like structure. It is also possible to produce heterodimers, in which two different fusion molecules are linked to each other by one or more covalent linkages, e.g. disulfide bond(s). Such bifunctional structures might be advantageous in that they are able to cross-link the same or different IgϵR(s) with different inhibitory receptors.

Receptor binding can be tested using any known assay method, such as competitive binding assays, direct and indirect sandwich assays. Thus, binding of a first polypeptide sequence included in the fusion molecules herein to a low-affinity IgG inhibitory receptor, or the binding of a second polypeptide sequence included herein to a high-affinity or low-affinity IgE receptor can be tested using conventional binding assays, such as competitive binding assays, including RIAs and ELISAs. Ligand/receptor complexes can be identified using traditional separation methods as filtration, centrifugation, flow cytometry, and the results from the binding assays can be analyzed using any conventional graphical representation of the binding data, such as Scatchard analysis.

The assays may be performed, for example, using a purified receptor, or intact cells expressing the receptor. One or both of the binding partners may be immobilized and/or labeled. A particular cell-based binding assay is described in the Example below.

The two polypeptide sequences present in the fusion molecules of the invention may be associated with one another by any means that allows them to cross-link the relevant receptors. Thus, association may take place by a direct or indirect covalent linkage, where "indirect" covalent linkage means that the two polypeptide sequences are part of separate molecules that interact with one another, either directly or indirectly. For example, each polypeptide sequence can be directly linked to one member of an interacting pair of molecules, such as, for example, a biotin/avidin pair. Alternatively, the two polypeptide sequences can be linked using a "dimerizer" system based on linkage to an entity that associates with a common ligand, such as dimerizer systems based on cyclosporine A, FK506, rapamycin, countermycin, and the like.

In a preferred embodiment, the first and second polypeptide sequences, such as, for example, two immunoglobulin constant region segments, or an immunoglobulin constant region sequence and an allergen or autoantibody sequence, are connected by a polypeptide linker. The polypeptide linker functions as a "spacer" whose function is to separate the functional receptor binding domains, or the Fcγ receptor binding domain and the IgE-binding sequence in the allergen or autoantigen, so that they can independently assume their proper tertiary conformation. The polypeptide linker usually comprises between about 5 and about 25 residues, and preferably contains at least about 10, more preferably at least about 15 amino acids, and is composed of amino acid residues which together provide a hydrophilic, relatively unstructured region. Linking amino acid sequences with little or no secondary structure work well. The specific amino acids in the spacer can vary, however, cysteines should be avoided. Suitable polypeptide linkers are, for example, disclosed in WO 88/09344 (published on Dec. 1, 1988), as are methods for the production of multifunctional proteins comprising such linkers.

In one embodiment, the fusion molecule containing allergen or autoantigen sequence is designed to have a dual purpose, where the fusion molecule (a) attenuates the allergic response by cross-linking inhibitory ITIM-containing receptors and stimulatory IgE receptors, as well as (b) provides antigenic material suitable for use in traditional desensitisation immunotherapies. This dual function is of value, as it provides material suitable for use in desensitisation therapy for allergic or autoimmune disease, and simultaneously has the inherent ability to suppress possible anaphylactic reactions caused by the administration of the antigen-containing fusion polypeptide to a subject during desensitisation immunotherapy.

Desensitisation therapies, including those using the fusion polypeptide of the present invention, utilize a mechanism of polypeptide internalization, followed by intracellular processing and presentation on the surface of a cell (e.g., but not limited to, antigen presenting cells; APCs) in the context of class I or class II major histocompatibility complex (MHC I or MHC II) molecules. It is the copresentation of antigen and MHC to T-cells that, under certain conditions known in the art, produces the desirable effect of "tolerance" to that antigen.

When used as vaccine material for desensitisation therapy, the fusion polypeptide of the present invention invention is internalized following administration to a subject, and thus, becomes intracellular. The internalization can be by any mechanism, although mechanisms comprising endocytosis, phagocytosis, pinocytosis, or any other mechanism of receptor or non-receptor-mediated internalization are contemplated. The internalization and subsequent processing of the fusion polypeptide is a requirement for presentation to T-cells.

Cell surface presentation of antigen by MHC I and MHC II utilize two distinct mechanisms. MHC I presentation processes antigen from the endoplasmic reticulum and cytosol in an ATP-dependent manner. Briefly, this process entails the marking of antigens for degradation by ubiquitination, followed by proteolytic processing in a proteasome-dependent manner. Additional "trimming" proteases are also implicated in the generation of peptides suitable for copresentation with MHC I (Rock and Goldberg, *Annu. Rev. Immunol.,* 17:739-779 [1999]; Pamer and Cresswell, *Annu. Rev. Immunol.,* 16:323-358 [1998]; and Luckey et al., *Jour. Immunol.,* 167: 1212-1221 [2001]). In contrast, processing of antigens for copresentation with MHC II utilizes endocytosis and an endosomal/lysosomal pathway that partitions antigens from the cytosol, and utilizes a number of distinct ATP-independent, acid-optimal proteases with various cleavage specificities (Watts, *Annu. Rev. Immunol.,* 15:821-850 [1997]; and Watts, *Curr. Opin. Immunol.,* 13:(1):26-31 [2001]).

Some of the signal sequences that mark MHC I antigens for processing via the proteasome pathway are known. It is recognized that antigens with large, bulky or charged amino termini are rapidly ubiquitinated and degraded, whereas the same proteins with N-terminal methionines or other small N-terminal residues are more resistant to ubiquitin-mediated degradation (Varshavsky, *Cell* 69:725-735 [1992]). Furthermore, the proteasome has been shown to contain at least three distinct protease activities. These are (1) a preference for peptide bonds following large hydrophobic residues (i.e., a chymotrypsin-like activity), (2) a cleavage specificity following basic residues, and (3) a cleavage preference following acidic residues (Rock and Goldberg, *Annu. Rev. Immunol.,* 17:739-779 [1999]; Pamer and Cresswell, *Annu. Rev. Immunol.,* 16:323-358 [1998]). It has been reported that these activities are allosterically controlled, and the chymotrypsin-like activity appears to be controlling or rate-limiting (Kisselev et al., *Mol. Cell.* 4(3):395-402 [1999]).

Intracellular proteases involved in the processing of antigen within specialized endosomal compartments for copresentation in conjunction with MHC II on APCs are also known, and their cleavage specificities have been determined (Watts, *Annu. Rev. Immunol.,* 15:821-850 [1997]; Villadangos et al., *Immunol. Rev.,* 172:109-120 [1999]; Antoniou et al., *Immunity* 12(4):391-398, [2000]; Villadangos and Ploegh, *Immunity* 12(3):233-239 [2000]; and Watts, *Curr. Opin. Immunol.,* 13:(1):26-31 [2001]). Many of these proteases involved in antigen processing in the endosomal degradation pathway are cysteine, aspartate or arginine endoproteases. Proteases involved in antigen processing include, but are not limited to, those listed in Table 3, below.

TABLE 3

| Protease | Recognition Motif |
|---|---|
| Cathepsins B, C, F, H, K, L, L2, O S, V and Z | cysteine proteases |
| Cathepsin D | aspartate proteases |
| Cathepsin E | aspartate protease |
| legumain/hemoglobinase asparaginyl endopeptidase (AEP) | cysteine protease family/ asparagine residues |
| Napsin A | aspartate protease |
| Napsin B | aspartate protease |

It is contemplated that in some embodiments of this invention, the fusion polypeptide contains amino acid sequences that facilitate either (a) protease cleavage of the linker, or (b) general proteolytic processing of the antigen, and thereby provides antigenic material that is more readily processed and presented on the cell surface (e.g., on the surface of an APC). In some embodiments, these proteolytic signals are within the linker sequence joining the antigen and Fcγ portions of the fusion polypeptide. In other embodiments, the proteolysis-promoting sequences are located in other parts of the fusion polypeptide, for example, in the N- or C-termini of the fusion polypeptide.

More specifically, it is contemplated that fusion polypeptides of the present invention can contain various amino acid sequences that promote ubiquitin-targetting of the polypeptide, and also can contain various amino acid residues to target the polypeptide for proteasome processing and MHC I copresentation. For example, the fusion polypeptide can be constructed to contain large, bulky or charged amino acid residues in the amino-terminus to promote ubiquitin targetting. Alternatively or concurrently, the fusion polypeptide can contain large hydrophobic, basic or acidic residues to direct proteasome cleavage anywhere in the fusion polypeptide, and most advantageously, within the polypeptide linker region. However, it is not necessary to have an understanding of the molecular mechanisms of antigen processing and presentation to make and use the present invention.

Similarly, it is contemplated that the fusion polypeptides of the present invention can contain various amino acid sequences for the purpose of promoting endosomal/lysosomal proteolytic processing and MHC II copresentation. For example, the fusion polypeptide can be enriched in cysteine, aspartate or arginine residues. In preferred embodiments, the linker region of the fusion polypeptide is enriched in these residues to facilitate cleavage of the fusion polypeptide into two halves, where the half containing the allergen or autoantigen sequence can be further processed and displayed on the APC in association with MHC II. However, it is not necessary to have an understanding of the molecular mechanisms of antigen processing and presentation to make and use the present invention.

In a less preferred embodiment, the IgG and IgE constant region sequences, the IgG constant region sequences and the allergen or autoantigen sequences, or sequences showing high degree of sequence identity with such sequences, may be directly fused to each other, or connected by non-polypeptide linkers. Such linkers may, for example, be residues of covalent bifunctional cross-linking agents capable of linking the two sequences without the impairment of the receptor (antibody) binding function. The bifunctional cross-linking reagents can be divided according to the specificity of their functional groups, e.g. amino, sulfhydryl, guanidino, indole, carboxyl specific groups. Of these, reagents directed to free amino groups have become especially popular because of their commercial availability, ease of synthesis and the mild reaction conditions under which they can be applied. A majority of heterobifunctional cross-linking reagents contains a primary amine-reactive group and a thiol-reactive group (for review, see Ji, T. H. "Bifunctional Reagents" in: *Meth. Enzymol.* 91:580-609 (1983)).

In a further specific embodiment, the two polypeptide sequences (including variants of the native sequences) are dimerized by amphiphilic helices. It is known that recurring copies of the amino acid leucine (Leu) in gene regulatory proteins can serve as teeth that "zip" two protein molecules together to provide a dimer. For further details about leucine zippers, which can serve as linkers for the purpose of the present invention, see for example: Landschulz, W. H., et al. Science 240:1759-1764 (1988); O'Shea, E. K. et al., *Science* 243: 38-542 (1989); McKnight, S. L., *Scientific American* 54-64, April 1991; Schmidt-Dorr. T. et al., *Biochemistry* 30:9657-9664 (1991); Blondel, A. and Bedouelle, H. *Protein Engineering* 4:457-461 (1991), and the references cited in these papers.

In a different approach, the two polypeptide sequences (including variants of the native sequences) are linked via carbohydrate-directed bifunctional cross-linking agents, such as those disclosed in U.S. Pat. No. 5,329,028.

The cross-linking of an inhibitory receptor expressed on mast cells and/or basophils, such as an ITIM-containing receptor, including IgG inhibitory receptors, e.g. FcγRIIb and a high-affinity IgE receptor, e.g. FcεRI or low-affinity IgE receptor, e.g. FcεRII, inhibit FcεR mediated biological responses. Such biological responses preferably are the mediation of an allergic reactions or autoimmune reactions via FcεR, including, without limitation, conditions associated with IgE mediated reactions, such as, for example, asthma, allergic rhinitis, food allergies, chronic urticaria and angioedema, allergic reactions to hymenophthera (e.g. bee and yellow jacket) stings or medications such as penicillin. These responses also include the severe physiological reaction of anaphylactic shock, which may occur upon inadvertent exposure to allergen (e.g., bee venom), or alternatively, may occur upon intentional administration of allergen or autoantigen, as during peptide therapy for treatment of allergic conditions or autoimmune disease.

2. Preparation of the Fusion Molecules

When the fusion molecules are polypeptides, in which the first and second polypeptide sequences are directly fused or functionally connected by a polypeptide linker, they can be prepared by well known methods of recombinant DNA technology or traditional chemical synthesis. If the polypeptides are produced by recombinant host cells, cDNA encoding the desired polypeptide of the present invention is inserted into a replicable vector for cloning and expression. As discussed before, the nucleotide and amino acid sequences of native immunoglobulin constant regions, including native IgG and IgE constant region sequences, are well known in the art and are readily available, for example, from Kabat et al., *Sequences of Proteins of Immunological Interest*, 5th Ed. Public Health Service, National Institute of Health, Bethesda, Md. (1991).

The sequences of a large number of allergens are also well known in the art. According to a nomenclature system established for allergens by the WHO/IUIS Allergen Nomenclature Subcommittee, the designation of any particular allergen is composed of the first three letters of the genus; a space; the first letter of the species name; a space and an arabic number. In the event that two species names have identical designations, they are discriminated from one another by adding one or more letters to each species designation. Using this designation, the allergen Aln G 1 is a major pollen allergen from the genus *Alnus* and the species *glutinosa*, the sequence of which is available from the SWISS-PROT database under the entry name MPAC_ALNGL (Primary Accession number: P38948) (Breitender et al, *J. Allergy Clin. Immunol.* 90:909-917 (1992)). A list of known antigens, including their origin, entry name and Primary Accession Number in the SWISS-PROT database is provided in Table 1. The molecular weight of most food allergens is between 10,000 and 70,000 Da. Some allergens, such as Ara h 1 (63.5 kDa) and Ara h 2 (17 kDa), occur as polymers that are larger, e.g. 200 to 300 kDa.

Similarly, a list of known autoantigens implicated in human disease is provided in Table 2. This table lists the autoantigen name(s), and the disease states associated with the presence of autoantibodies to the particular autoantigen. This table lists only those autoimmune diseases for which the molecular identification of the autoantigen has been made. As can be seen in the table, the assignment of one particular autoantibody to one specific disease is frequently complex, as patients with a single autoimmune disorder often show more than one autoreactive antibody, and vice versa, a particular autoantigen may be involved on more than one autoimmune disease. It is not intended that the invention be limited to the use of only those sequences provided in Table 2. As autoantigens are identified in additional autoimmune diseases, those molecular sequences will also find use with the invention.

As noted earlier, it might be advantageous to use in the fusion molecules of the present invention a fragment of a native or variant allergen or autoantigen that contains only a single IgE-binding site or immunodominant epitope. For many of the allergen proteins listed in Tables 1 and 2, the IgE-binding sites and immunodominant epitopes have been determined. For example, the IgE-binding epitopes of Par j 2, a major allergen of *Parietaria judaica* pollen, have been determined by Costa et al., *Allergy* 55:246-50 (2000). The IgE-binding epitopes of major peanut antigens Ara h 1 (Burks et al., *Eur. J. Biochem.* 254:334-9 (1997)); Ara h 2 (Stanley et al., *Arch Biochem. Biophys.* 342:244-53 (1997)); and Ara h 3 (Rabjohn et al., *J. Clin. Invest.* 103:535-42 (1999)) are also known, just to mention a few. Also, for the CNS myelin basic protein (MBP) autoantigen, the immunodominant epitope has been mapped to a small domain encompassing approximately amino acid positions 83 through 99 (Ota et al., *Nature* 346:183-187 [1990]; Warren and Catz, *J. Neuroimmunol.*, 39:81-90 [1992]; Warren and Catz, *J. Neuroimmunol.*, 43:87-96 [1993]; and Warren et al., *Proc. Natl. Acad. Sci. USA* 92:11061-11065 [1995]). Short synthetic peptides corresponding to this epitope have been used in peptide immunotherapy for multiple sclerosis (e.g., Warren et al., *J. Neurol. Sci.*, 152:31-38 [1997]).

Suitable vectors are prepared using standard techniques of recombinant DNA technology, and are, for example, described in "Molecular Cloning: A Laboratory Manual", 2$^{nd}$ edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Handbook of Experimental Immunology", 4$^{th}$ edition (D. M. Weir & C. C. Blackwell, eds., Blackwell Science Inc., 1987); "Gene Transfer Vectors for Mammalian Cells" (J. M. Miller & M. P. Calos, eds., 1987); "Current Protocols in Molecular Biology" (F. M. Ausubel et al., eds., 1987); "PCR: The Polymerase Chain Reaction", (Mullis et al., eds., 1994); and "Current Protocols in Immunology" (J. E. Coligan et al., eds., 1991). Isolated plasmids and DNA fragments are cleaved, tailored, and ligated together in a specific order to generate the desired vectors. After ligation, the vector containing the gene to be expressed is transformed into a suitable host cell.

Host cells can be any eukaryotic or prokaryotic hosts known for expression of heterologous proteins. Accordingly, the polypeptides of the present invention can be expressed in eukaryotic hosts, such as eukaryotic microbes (yeast) or cells isolated from multicellular organisms (mammalian cell cultures), plants and insect cells. Examples of mammalian cell lines suitable for the expression of heterologous polypeptides include monkey kidney CV1 cell line transfommed by SV40 (COS-7, ATCC CRL 1651); human embryonic kidney cell line 293S (Graham et al, *J. Gen. Virol.* 36:59 [1977]); baby hamster kidney cells (BHK, ATCC CCL 10); Chinese hamster ovary (CHO) cells (Urlaub and Chasin, *Proc. Natl. Acad. Sci. USA* 77:4216 [1980]; monkey kidney cells (CV1-76, ATCC CCL 70); African green monkey cells (VERO-76, ATCC CRL-1587); human cervical carcinoma cells (HELA, ATCC CCL 2); canine kidney cells (MDCK, ATCC CCL 34); human lung cells (W138, ATCC CCL 75); and human liver cells (Hep G2, HB 8065). In general myeloma cells, in particular those not producing any endogenous antibody, e.g. the non-immunoglobulin producing myeloma cell line SP2/0, are preferred for the production of the fusion molecules herein.

Eukaryotic expression systems employing insect cell hosts may rely on either plasmid or baculoviral expression systems. The typical insect host cells are derived from the fall army worm (*Spodoptera frugiperda*). For expression of a foreign protein these cells are infected with a recombinant form of the baculovirus *Autographa californica* nuclear polyhedrosis virus which has the gene of interest expressed under the control of the viral polyhedrin promoter. Other insects infected by this virus include a cell line known commercially as "High 5" (Invitrogen) which is derived from the cabbage looper (*Trichoplusia ni*). Another baculovirus sometimes used is the *Bombyx mori* nuclear polyhedorsis virus which infect the silk worm (*Bombyx mori*). Numerous baculovirus expression systems are commercially available, for example, from Invitrogen (Bac-N-Blue™), Clontech (BacPAK™ Baculovirus Expression System), Life Technologies (BAC-TO-BAC™), Novagen (Bac Vector System™), Pharmingen and Quantum Biotechnologies). Another insect cell host is common fruit fly, *Drosophila melanogaster*, for which a transient or stable plasmid based transfection kit is offered commercially by Invitrogen (The DES™ System).

*Saccharomyces cerevisiae* is the most commonly used among lower eukaryotic hosts. However, a number of other genera, species, and strains are also available and useful herein, such as *Pichia pastoris* (EP 183,070; Sreekrishna et al., *J. Basic Microbiol.*, 28:165-278 [1988]). Yeast expression systems are commercially available, and can be purchased, for example, from Invitrogen (San Diego, Calif.). Other yeasts suitable for bi-functional protein expression include, without limitation, *Kluyveromyces* hosts (U.S. Pat. No. 4,943, 529), e.g. *Kluyveromyces lactis; Schizosaccharomyces pombe* (Beach and Nurse, *Nature* 290:140 (1981); *Aspergillus* hosts, e.g., *A. niger* (Kelly and Hynes, *EMBO J.*, 4:475-479 [1985]) and *A. nidulans* (Ballance et al., *Biochem. Biophys. Res. Commun.*, 112:284-289 [1983]), and *Hansenula* hosts, e.g., *Hansenula polymorpha*. Yeasts rapidly growth on inexpensive (minimal) media, the recombinant can be easily selected by complementation, expressed proteins can be specifically engineered for cytoplasmic localization or for extracellular export, and are well suited for large-scale fermentation.

Prokaryotes are the preferred hosts for the initial cloning steps, and are particularly useful for rapid production of large amounts of DNA, for production of single-stranded DNA templates used for site-directed mutagenesis, for screening many mutants simultaneously, and for DNA sequencing of the mutants generated. *E. coli* strains suitable for the production of the peptides of the present invention include, for example, BL21 carrying an inducible T7 RNA polymerase gene (Studier et al., *Methods Enzymol.*, 185:60-98 [1990]); AD494 (DE3); EB105; and CB (*E. coli* B) and their derivatives; K12 strain 214 (ATCC 31,446); W3110 (ATCC 27,325); X1776 (ATCC 31,537); HB101 (ATCC 33,694); JM101 (ATCC 33,876); NM522 (ATCC 47,000); NM538 (ATCC 35,638); NM539 (ATCC 35,639), etc. Many other species and genera of prokaryotes may be used as well. Indeed, the peptides of the present invention can be readily produced in large amounts by utilizing recombinant protein expression in bacteria, where the peptide is fused to a cleavable ligand used for affinity purification.

Suitable promoters, vectors and other components for expression in various host cells are well known in the art and are disclosed, for example, in the textbooks listed above.

Whether a particular cell or cell line is suitable for the production of the polypeptides herein in a functionally active form, can be determined by empirical analysis. For example, an expression construct comprising the coding sequence of the desired molecule may be used to transfect a candidate cell line. The transfected cells are then growth in culture, the medium collected, and assayed for the presence of secreted polypeptide. The product can then be quantitated by methods known in the art, such as by ELISA with an antibody specifically binding the IgG, IgE, or allergen portion of the molecule.

In certain instances, particularly when two polypeptide sequences making up the bifunctional molecule of the present invention are connected with a non-polypeptide linker, it may be advantageous to individually synthesize the first and second polypeptide sequences, e.g. by any of the recombinant approaches discussed above, followed by functionally linking the two sequences.

Alternatively, the two polypeptide sequences, or the entire molecule, may be prepared by chemical synthesis, such as solid phase peptide synthesis. Such methods are well known to those skilled in the art. In general, these methods employ either solid or solution phase synthesis methods, described in basic textbooks, such as, for example, J. M. Stewart and J. D. Young, Solid Phase Peptide Synthesis, 2nd Ed., Pierce Chemical Co., Rockford, Ill. (1984) and G. Barany and R. B. Merrifield, The Peptide: Analysis Synthesis, Biology, editors E. Gross and J. Meienhofer, Vol. 2, Academic Press, New York, (1980), pp. 3-254, for solid phase peptide synthesis techniques; and M. Bodansky, Principles of Peptide Synthesis, Springer-Verlag, Berlin (1984) and E. Gross and J. Meienhofer, Eds., The Peptides: Analysis, Synthesis, Biology, supra, Vol. 1, for classical solution synthesis.

The fusion molecules of the present invention may include amino acid sequence variants of native immunoglobulin (e.g., IgG and/or IgE), allergen (e.g., Ara h 2 sequences) or autoantigen (e.g., myelin basic protein). Such amino acid sequence variants can be produced by expressing the underlying DNA sequence in a suitable recombinant host cell, or by in vitro synthesis of the desired polypeptide, as discussed above. The nucleic acid sequence encoding a polypeptide variant is preferably prepared by site-directed mutagenesis of the nucleic acid sequence encoding the corresponding native (e.g. human) polypeptide. Particularly preferred is site-directed mutagenesis using polymerase chain reaction (PCR) amplification (see, for example, U.S. Pat. No. 4,683,195 issued 28 Jul. 1987; and *Current Protocols In Molecular Biology*, Chapter 15 (Ausubel et al., ed., 1991). Other site-directed mutagenesis techniques are also well known in the art and are described, for example, in the following publications: *Current Protocols In Molecular Biology*, supra, Chapter 8; Molecular Cloning: A Laboratory Manual., $2^{nd}$ edition (Sambrook et al., 1989); Zoller et al., *Methods Enzmmol.* 100:468-500 (1983); Zoller & Smith, *DNA* 3:479-488 (1984); Zoller et al., *Nucl. Acids Res.*, 10:6487 (1987); Brake et al., *Proc. Natl. Acad. Sci. USA* 81:4642-4646 (1984); Botstein et al., *Science* 229:1193 (1985); Kunkel et al., *Methods Enzymol.* 154:367-82 (1987); Adelman et al., *DNA* 2:183 (1983); and Carter et al., *Nucl. Acids Res.*, 13:4331 (1986). Cassette mutagenesis (Wells et al., *Gene*, 34:315 [1985]), and restriction selection mutagenesis (Wells et al., *Philos. Trans. R. Soc. London Ser A*, 317:415 [1986]) may also be used.

Amino acid sequence variants with more than one amino acid substitution may be generated in one of several ways. If the amino acids are located close together in the polypeptide chain, they may be mutated simultaneously, using one oligonucleotide that codes for all of the desired amino acid substitutions. If, however, the amino acids are located some distance from one another (e.g., separated by more than ten amino acids), it is more difficult to generate a single oligonucleotide that encodes all of the desired changes. Instead, one of two alternative methods may be employed. In the first method, a separate oligonucleotide is generated for each amino acid to be substituted. The oligonucleotides are then annealed to the single-stranded template DNA simultaneously, and the second strand of DNA that is synthesized from the template will encode all of the desired amino acid substitutions. The alternative method involves two or more rounds of mutagenesis to produce the desired mutant.

The polypeptides of the invention can also be prepared by the combinatorial peptide library method disclosed, for example, in International Patent Publication PCT WO 92/09300. This method is particularly suitable for preparing and analyzing a plurality of molecules, that are variants of a given predetermined sequences, and is, therefore, particularly useful in identifying polypeptides with improved biological properties, which can then be produced by any technique known in the art, including recombinant DNA technology and/or chemical synthesis.

3. Therapeutic Uses of the Fusion Molecules of the Invention

The present invention provides new therapeutic strategies for treating immune diseases resulting from excess or inappropriate immune response, as well as methods for the prevention of anaphylactic response. Specifically, the invention provides compounds and methods for the treatment of type I hypersensitivity diseases mediated through the high-affinity IgE receptor, as well as for the treatment of autoimmune diseases (e.g., autoimmune diabetes mellitus, rheumatoid arthritis, and multiple sclerosis). The invention provides advantages over existing methods for treating immune diseases. The methods described herein find use in the treatment of any mammalian subject, however, humans are a preferred subject.

Nature of the Diseases Targeted

Allergic reactions are classified following the Gell and Coombs Classification, depending on the type of immune response induced and the resulting tissue damage that develops as a result of reactivity to an antigen. A Type I reaction (immediate hypersensitivity) occurs when an antigen (called an allergen in this case) enters the body and encounters mast cells or basophils that are sensitized to the allergen as a result of IgE specific to the allergen being attached to its high-affinity receptor, FcεRI. Upon reaching the sensitized cell, the allergen cross-links IgE molecules bound to FcεRI, causing an increase in intracellular calcium ($Ca^{2+}$) that triggers the rapid release of pre-formed mediators, such as histamine and proteases, and newly synthesized, lipid-derived mediators such as leukotrienes and prostaglandins (i.e., degranulation). Excessive release of these autocoids produces the acute clinical symptoms of allergy. Stimulated basophils and mast cells will also produce and release proinflammatory mediators, which participate in the acute and delayed phase of allergic reactions.

As discussed before and shown in Table 1 above, a large variety of allergens has been identified so far, and new allergens are identified, cloned and sequenced practically every day.

Ingestion of an allergen results in gastrointestinal and systemic allergic reactions. The most common food allergens involved are peanuts, shellfish, milk, fish, soy, wheat, egg and tree nuts such as walnuts. In susceptible people, these foods can trigger a variety of allergic symptoms, such as nausea, vomiting, diarrhea, urticaria, angioedema, asthma and full-blown anaphylaxis.

Inhalation of airborne allergens results in allergic rhinitis and allergic asthma, which can be acute or chronic depending on the nature of the exposure(s). Exposure to airborne allergens in the eye results in allergic conjunctivitis. Common airborne allergens includes pollens, mold spores, dust mites and other insect proteins. Cat, dust mite and cockroach allergens are the most common cause of perrenial allergic rhinitis while grass and weed and tree pollens are the most common cause of seasonal hay fever and allergic asthma.

Cutaneous exposure to an allergen, e.g. natural rubber latex proteins as found in latex gloves, may result in local allergic reactions manifest as hives (urticaria) at the places of contact with the allergen. Absoprtion of the allergen via the skin may also cause systemic symptoms.

Systemic exposure to an allergen such as occurs with a bee sting, the injection of penicillin, or the use of natural rubber latex (NRL) gloves inside a patient during surgery may result in, cutaneous, gastrointestinal and respiratory reactions up to and including airway obstruction and full blown anaphylaxis. *Hymenoptera* insect stings are commonly cause allergic reactions, often leading the anaphylactic shock. Examples include various stinging insects including honeybees, yellow jackets, yellow hornets, wasps and white-faced hornets. Certain ants that also sting known as fire ants (*Solenopsis invicta*) are an increasing cause of serious allergy in the US as they expand their range in this country. Proteins in NRL gloves have become an increasing concern to health care workers and patients and at present, there is no successful form of therapy for this problem except avoidance.

A large number of autoimmune diseases have also been identified, as well as the autoantigens recognized by the autoantibodies implicated in the pathology of autoimmune diseases, as shown in Table 2, and known in the art (see, e.g., van Venrooij and Maini (Eds.), *Manual of Biological Markers of Disease*, Kluwer Academic Publishers [1996]; Rose and MacKay (Eds.), *The Autoimmune Diseases*, Third Edition, Academic Press [1998]; and Lydyard and Brostoff (Eds.), *Autoimmune Disease Aetiopathogenesis, Diagnosis and Treatment*, Blackwell Science Ltd. [1994]). The list of autoantigens and autoimmune diseases in Table 2 is not exhaustive and is not intended to be limiting, as it is contemplated that new autoantigens and diseases with autoimmune etiologies will be identified in the future. It is not intended that the invention be limited to the treatment of the diseases taught in Table 2, and it is not intended that autoantigen sequences finding use with the invention be limited to those sequences provided in Table 2. Examples of autoimmune diseases for which the autoantigen is not currently known, but may be identified in the future, includes but are not limited to Behcet's disease, Crohn's disease, Kawasaki's disease, autoimmune male infertility, Raynauds disease, Takayasu's arteritis and Giant cell arteritis.

Uses of Compounds for Targeted Diseases

The compounds disclosed herein can be used to treat or prevent a large number of immune diseases, such as allergic diseases, autoimmune diseases, and anaphylactic shock response. The present invention provides new therapeutic strategies for treating immune diseases resulting from excess or inappropriate immune response. Specifically, the invention provides compositions and methods finding the uses described below. The uses itemized herein are not intended to be limiting, as modification of these uses will be apparent to one familiar with the art.

(a) The invention finds use in the treatment of type I hypersensitivity diseases mediated through the high-affinity IgE receptor (e.g., allergic diseases, such as allergic asthma). In these methods, the FcεR receptors are crosslinked to inhibitory FcγR receptors via the fusion polypeptides of the present invention, resulting in a downregulation of the IgE and FcεR activity. The compounds disclosed herein can be used to inhibit or prevent acute or chronic IgE mediated reactions to major environmental and occupational allergens.

When the fusion polypeptide compositions of the present invention comprise IgG heavy chain constant region sequences and allergen sequences, the immune suppression will be specific for the particular allergen. When the fusion polypeptide compositions of the present invention comprise IgG heavy chain constant region sequences and IgE heavy chain constant region sequences, the suppression of the type I hypersensitivity response will be global, and not specific for a particular allergen.

(b) Some fusion polypeptide compositions of the invention can be used to provide vaccination material suitable for allergy immunotherapy to induce a state of non-allergic reactivity (i.e., desensitisation or allergic tolerance) to specific allergens. When used in this capacity, the fusion polypeptide material comprises IgG heavy chain constant region sequences and allergen sequences. It is contemplated that in this case, the fusion polypeptide is internalized, processed and presented on the surface of cells (e.g., but not limited to APCs). Use of the fusion polypeptides in this manner provide an advantage over existing vaccination materials, as the fusion polypeptide has intrinsic ability to prevent or downregulate any acute type I hypersensitivity response (e.g., an anaphylactic reaction) that may result from response to the allergen sequence component of the fusion polypeptide. It is contemplated that this prevention or downregulation occurs through crosslinking of the stimulatory Fcε receptors with inhibitory Fcγ receptors via the fusion polypeptide and endogenous IgE specific for the allergen sequence. However, it is not necessary to understand the mechanism responsible for the downregulation in order to make or use the present invention. In this embodiment, the fusion polypeptide may or may not comprise particular amino acid sequences that promote targetting and proteolytic processing that facilitate copresentation of the antigen sequence with MHC I or MHC II for the induction of tolerance.

(c) Some fusion polypeptide compositions of the invention comprising IgG heavy chain constant region sequences and autoantigen sequences (e.g., myelin basic protein) find use in the treatment of autoimmune diseases (e.g., multiple sclerosis) as vaccination material suitable for use in immunotherapy. When used in this capacity, it is contemplated that the polypeptide material is processed and presented on antigen presenting cells (APCs). In this embodiment, the fusion polypeptide may or may not comprise particular amino acid sequences that promote targetting and proteolytic processing that facilitate copresentation of the autoantigen sequence with MHC I or MHC II for the induction of tolerance. The fusion polypeptide material used in this mode of therapy has the additional benefit of having the intrinsic ability to prevent or downregulate any acute type I hypersensitivity response (e.g., an anaphylactic reaction) that may result from reactivity directed against the autoantigen component on the fusion polypeptide. It is contemplated that this downregulation occurs through crosslinking the stimulatory Fcε receptors with inhibitory Fcγ receptors via the fusion polypeptide and endogenous IgE specific for the autoantigen sequence. However, it is not necessary to understand the mechanism responsible for the downregulation in order to make or use the present invention.

(d) The fusion polypeptides of the present invention can be used in conjunction with traditional whole antigen desensitization or peptide immunotherapies in the treatment of allergies or autoimmune disorders, for the purpose of preventing the dangerous anaphylactic reactions frequently observed in response to traditional immunotherapies. When used in this capacity, the fusion polypeptide compositions of the invention will comprise IgG heavy chain constant region sequences, as well as either IgE heavy chain constant region sequences, allergen peptide sequences, or autoantigen peptide sequences. It is contemplated that the fusion polypeptide can be delivered to a subject before, during or after the delivery of other traditional peptide therapies in the treatment of allergic or autoimmune diseases to prevent anaphylactic reaction in response to the immunotherapy material. In a preferred embodiment, the fusion polypeptide composition can be given to a subject who has previously displayed type I hypersensitivity to a particular whole antigen or peptide during immunotherapy, and thus, is at risk for hypersensitivity responses to future immunotherapies with that same antigen. This use of the fusion polypeptides of the invention will provide a platform for the reinstitution of traditional peptide therapies that were previously abandoned due to their induction of systemic hypersensitivity effects (e.g., causing anaphylactic reactions).

(e) The compositions and methods of the invention can provide a prophylactic effect against allergic disease by preventing allergic sensitization to environmental and occupational allergens when administered to at-risk individuals (e.g., those at genetic risk of asthma and those exposed to occupational allergens in the workplace).

(f) It is contemplated that the methods for treating a subject using the fusion polypeptides of the invention may comprise the simultaneous delivery of more than one fusion polypeptide to achieve a desired curative or prophylactic effect. For example, an allergen or autoantigen may not have a single immunodominant epitope, and alternatively, may have multiple epitopes recognized by native IgE molecules. In that case, multiple fusion polypeptides, each comprising a different epitope, can be delivered to a subject.

In another example, patients who demonstrate an autoimmune disorder frequently test positive for the presence of more than one type of autoantibody, and thus, have more than one physiological autoantigen. In that case, it is contemplated that the methods for treating that patient may comprise the simultaneous delivery of more than one fusion polypeptide to achieve the desired immunosuppressive effect, where each fusion polypeptide comprises a different suitable autoantigen sequence. In this case, the fusion polypeptide(s) can also be given prophylactically, for the purpose of preventing the anaphylactic responses that may occur during autoantigen tolerance therapy.

(g) It is also contemplated that in some embodiments of the invention, the fusion polypeptides are used in combination with other treatments, e.g., co-delivery with biological modifiers (e.g., antagonists of inflammatory response mediators, including tumor necrosis factor α (TNFα), IL-1, IL-2, interferon-α (INF-α), and INF-β), immuno-suppressive therapy (e.g., methotrexate, calcineurin inhibitors or steroids), or various adjuvants, as known in the art.

Advantages of the Invention

The bifunctional gamma-epsilon compounds (i.e., the fusion polypeptides) described can be used to prevent allergic reactions to any specific allergen or group of allergens. By occupying a critical number of FcεRI receptors, these molecules will inhibit the ability of basophils and mast cells to react to any allergen so as to prevent including, without limitation, asthma, allergic rhinitis, atopic dermatitis, food allergies, forms of autoimmune urticaria and angioedema, up to and including anaphylactic shock. Thus these compounds could be used acutely to desensitize a patient so that the administration of a therapeutic agent (e.g., penicillin) can be given safely. Similarly, they can be used to desensitize a patient so that standard allergen vaccination may be given with greater safety, e.g., peanut or latex treatment. They can also be used as chronic therapy to prevent clinical reactivity to prevent environmental allergens such as foods or inhalant allergens.

The present invention provides gamma-allergen bifunctional fusion molecules for use in a novel form of allergy vaccination that will be safer and more effective in the treatment of a variety of IgE-mediated allergic reactivity, including, without limitation, asthma, allergic rhinitis, atopic dermatitis, food allergies, urticaria and angioedema, up to and including anaphylactic shock. Having the allergen fused to a molecule that will bind to FcγRIIb on mast cells and basophils will prevent the allergen from inducing local or systemic allergic reactions. Such local or systemic allergic reactions are major problem in allergen vaccination as currently practiced. The gamma-allergen fusion proteins will be able to be given in higher doses over a shorter interval and with greater safety than standard allergen therapy. These benefits of the invention are equally applicable to the situation where delivery of a traditional vaccine for the treatment of an autoimmune disease may cause a severe IgE-mediated (i.e., allergic) immune response, including anaphylactic shock.

In addition, use of the gamma-allergen compounds will cause antigen specific desensitization to that specific allergen. Thus the gamma-allergen compounds will give a window of safe exposure to the allergen be it as an acute or recurring treatment as would be needed in using a therapeutic monoclonal antibody to which a patient has developed an allergic (IgE) response or as chronic treatment for prevention of unintentional exposures such as occurs with peanut allergens.

The importance of being able to suppress a hypersensitivity response is expected to increase with the development of recombinant DNA and protein technologies. As an increasing number of recombinant polypeptide products find their way into therapeutic applications in the near future, there is an increased likelihood that these recombinant products will trigger hyperimmune responses. The gamma-allergen compounds can even be used along with conventional allergen vaccination so as to provide an extra margin of safety while large doses of standard allergen are given. Similarly, the fusion polypeptides of the present invention can be used in conjunction with recombinant polypeptide therapeutics so as to diminish the risk of hyperimmune response to the recombinant therapeutic.

The bifunctional autoantigen-Fcγ fusion polypeptides described can be used prophylactically to prevent type-I hypersensitivity reactions to autoantigen sequences used in autoantigen tolerance therapy for the treatment of autoimmune disease. It is contemplated that a critical number of Fcε and inhibitory Fcγ receptors will be crosslinked via the formation of a bridge comprising the fusion polypeptide and endogenous IgE specific for the autoantigen sequence (however, it is not necessary to understand the mechanisms of immune suppression to make or use the invention). Thus, these fusion polypeptides will inhibit the ability of basophils and mast cells to react to exogenously supplied autoantigen, as would be encountered during tolerance therapy, so as to prevent type-I hypersensitivity reactions, up to and including anaphylactic shock. These fusion polypeptides could be used to desensitize a patient so that the therapeutic administration of autoantigen peptide (i.e., the tolerance therapy) can take place with greater safety.

The present invention provides autoantigen-Fcγ fusion polypeptides for use in a novel form of autoimmune vaccination that will be safer and more effective in the treatment of autoimmune disease. The fusion polypeptide can be coadminstered with isolated autoantigen, or alternatively, no supplemental autoantigen is administered. Having the autoantigen sequence fused to a molecule that will bind to FcγRIIb on mast cells and basophils will prevent the autoantigen sequence (either by itself or as part of the fusion polypeptide) being able to induce local or systemic type I hypersensitivity reactions. Such local or systemic allergic reactions are a major concern in vaccination therapies as currently practiced. The fusion polypeptides comprising autoantigen and Fcγ will permit the administration of autoantigen sequences in higher doses over a shorter interval and with greater safety than standard autoantigen-alone peptide therapy.

Alternatively, when used in conjunction with free autoantigen, a fusion polypeptide comprising Fcϵ and Fcγ can be used during the desensitization therapy, for the purpose of suppressing type-I hypersensitivity reactions. This Fcϵ-Fcγ fusion polypeptide has the added advantage that it can be used to suppress any IgE-mediated type-I hypersensitivity response, and not only the response solicited from a particular autoantigen sequence.

Furthermore, use of the autoantigen-Fcγ fusion compounds will result in antigen specific suppression (i.e., desensitization) to that specific autoantigen. This antigen-specific immune suppression is strongly preferable to generalized immune suppression, as broad suppression leaves the patient susceptible to possibly life-threatening infections (in addition to the side effects of the potent immunosuppressive drugs, such as cyclosporine A and methotrexate).

In addition, the chimeric gamma-epsilon compounds herein hold great promise for the treatment of autoimmune chronic urticaria and angioedema. Urticaria is a skin symptom that may accompany allergies but often is idiopathic. It is a relatively common disorder caused by localized cutaneous mast cell degranulation, with resultant increased dermal vascular permeability culminating in pruritic wheals. Angioedema is a vascular reaction involving the deep dermis or subcutaneous or submucosal tissues caused by localized mast cell degranulation. This results in tissue swelling that is pruritic or painful. Chronic urticaria and angioedema often occur together although they occur individually as well. These conditions are common and once present for more than six months, they often last a decade or more. Although not fatal, they are very troubling to patients, as the frequency of recurring attacks disrupts daily activities and thereby results in significant morbidity. Standard therapy is often unsuccessful in these conditions, and is distressing to the point that chemotherapy with cyclosporine A and other potent immunosuppressive drugs has recently been advocated. Increasing evidence suggests that as many as 60% of patients with these conditions actually have an autoimmune disease, in which they make functional antibodies against the FcϵRI receptor. For further details, see Hide et al., *N. Engl. J. Med.* 328:1599-1604 (1993); Fiebiger et al., *J. Clin. Invest.* 96:2606-12 (1995); Fiebiger eta., *J. Clin. Invest.* 101:243-51 (1998); Kaplan, A. P., Urticaria and Angioedema, In: *Inflammation: Basic Principles and Clinical Correlates* (Galliin and Snyderman eds.), 3rd Edition, Lippincott & Wilkins, Philadelphia, 1999, pp. 915-928. The fusion molecules of the present invention are believed to form the basis for a novel and effective treatment of these diseases by safely blocking access to the FcϵRI.

Compositions and Formulations of the Invention

For therapeutic uses, including prevention, the compounds of the invention can be formulated as pharmaceutical compositions in admixture with pharmaceutically acceptable carriers or diluents. Methods for making pharmaceutical formulations are well known in the art. Techniques and formulations generally may be found in *Remington's Pharmaceutical Sciences,* 18th Edition, Mack Publishing Co., Easton, Pa. 1990. See, also, Wang and Hanson "*Parenteral Formulations of Proteins and Peptides: Stability and Stabilizers", Journal of Parenteral Science and Technology*, Technical Report No. 10, Supp. 42-2S (1988). A suitable administration format can best be determined by a medical practitioner for each patient individually.

Pharmaceutical compositions of the present invention can comprise a fusion molecule of the present invention along with conventional carriers and optionally other ingredients.

Suitable forms, in part, depend upon the use or the route of entry, for example oral, transdermal, inhalation, or by injection. Such forms should allow the agent or composition to reach a target cell whether the target cell is present in a multicellular host or in culture. For example, pharmacological agents or compositions injected into the blood stream should be soluble. Other factors are known in the art, and include considerations such as toxicity and forms that prevent the agent or composition from exerting its effect.

Carriers or excipients can also be used to facilitate administration of the compound. Examples of carriers and excipients include calcium carbonate, calcium phosphate, various sugars such as lactose, glucose, or sucrose, or types of starch, cellulose derivatives, gelatin, vegetable oils, polyethylene glycols and physiologically compatible solvents. The compositions or pharmaceutical composition can be administered by different routes including, but not limited to, oral, intravenous, intra-arterial, intraperitoneal, subcutaneous, intranasal or intrapulmonary routes.

The desired isotonicity of the compositions can be accomplished using sodium chloride or other pharmaceutically acceptable agents such as dextrose, boric acid, sodium tartrate, propylene glycol, polyols (such as mannitol and sorbitol), or other inorganic or organic solutes.

For systemic administration, injection is preferred, e.g., intramuscular, intravenous, intra-arterial, etc. For injection, the compounds of the invention are formulated in liquid solutions, preferably in physiologically compatible buffers such as Hank's solution or Ringer's solution. Alternatively, the compounds of the invention are formulated in one or more excipients (e.g., propylene glycol) that are generally accepted as safe as defined by USP standards. They can, for example, be suspended in an inert oil, suitably a vegetable oil such as sesame, peanut, olive oil, or other acceptable carrier. Preferably, they are suspended in an aqueous carrier, for example, in an isotonic buffer solution at pH of about 5.6 to 7.4. These compositions can be sterilized by conventional sterilization techniques, or can be sterile filtered. The compositions can contain pharmaceutically acceptable auxiliary substances as required to approximate physiological conditions, such as pH buffering agents. Useful buffers include for example, sodium acetate/acetic acid buffers. A form of repository or "depot" slow release preparation can be used so that therapeutically effective amounts of the preparation are delivered into the bloodstream over many hours or days following transdermal injection or delivery. In addition, the compounds can be formulated in solid form and redissolved or suspended immediately prior to use. Lyophilized forms are also included.

Alternatively, certain molecules identified in accordance with the present invention can be administered orally. For oral administration, the compounds are formulated into conventional oral dosage forms such as capsules, tablets and tonics.

Systemic administration can also be by transmucosal or transdermal. For transmucosal or transdermal administration, penetrants appropriate to the barrier to be permeated are used in the formulation. Such penetrants are generally known in the art, and include, for example, for transmucosal administration, bile salts and fusidic acid derivatives. In addition, detergents can be used to facilitate permeation. Transmucosal administration can be, for example, through nasal sprays or using suppositories.

A preferred route for administration of the compounds of the invention may be inhalation for intranasal and/or intrapulmonary delivery. For administration by inhalation, usually inhalable dry power compositions or aerosol compositions are used, where the size of the particles or droplets is selected to ensure deposition of the active ingredient in the desired part of the respiratory tract, e.g. throat, upper respiratory tract or lungs. Inhalable compositions and devices for their administration are well known in the art. For example, devices for the delivery of aerosol medications for inspiration are known. One such device is a metered dose inhaler that delivers the same dosage of medication to the patient upon each actuation of the device. Metered dose inhalers typically include a canister containing a reservoir of medication and propellant under pressure and a fixed volume metered dose chamber. The canister is inserted into a receptacle in a body or base having a mouthpiece or nosepiece for delivering medication to the patient. The patient uses the device by manually pressing the canister into the body to close a filling valve and capture a metered dose of medication inside the chamber and to open a release valve which releases the captured, fixed volume of medication in the dose chamber to the atmosphere as an aerosol mist. Simultaneously, the patient inhales through the mouthpiece to entrain the mist into the airway. The patient then releases the canister so that the release valve closes and the filling valve opens to refill the dose chamber for the next administration of medication. See, for example, U.S. Pat. No. 4,896,832 and a product available from 3M Healthcare known as Aerosol Sheathed Actuator and Cap.

Another device is the breath actuated metered dose inhaler that operates to provide automatically a metered dose in response to the patient's inspiratory effort. One style of breath actuated device releases a dose when the inspiratory effort moves a mechanical lever to trigger the release valve. Another style releases the dose when the detected flow rises above a preset threshold, as detected by a hot wire anemometer. See, for example, U.S. Pat. Nos. 3,187,748; 3,565,070; 3,814,297; 3,826,413; 4,592,348; 4,648,393; 4,803,978.

Devices also exist to deliver dry powdered drugs to the patient's airways (see, e.g. U.S. Pat. No. 4,527,769) and to deliver an aerosol by heating a solid aerosol precursor material (see, e.g. U.S. Pat. No. 4,922,901). These devices typically operate to deliver the drug during the early stages of the patient's inspiration by relying on the patient's inspiratory flow to draw the drug out of the reservoir into the airway or to actuate a heating element to vaporize the solid aerosol precursor.

Devices for controlling particle size of an aerosol are also known, see, for example, U.S. Pat. Nos. 4,790,305; 4,926,852; 4,677,975; and 3,658,059.

For topical administration, the compounds of the invention are formulated into ointments, salves, gels, or creams, as is generally known in the art.

If desired, solutions of the above compositions can be thickened with a thickening agent such as methyl cellulose. They can be prepared in emulsified form, either water in oil or oil in water. Any of a wide variety of pharmaceutically acceptable emulsifying agents can be employed including, for example, acacia powder, a non-ionic surfactant (such as a Tween), or an ionic surfactant (such as alkali polyether alcohol sulfates or sulfonates, e.g., a Triton).

Compositions useful in the invention are prepared by mixing the ingredients following generally accepted procedures. For example, the selected components can be mixed simply in a blender or other standard device to produce a concentrated mixture which can then be adjusted to the final concentration and viscosity by the addition of water or thickening agent and possibly a buffer to control pH or an additional solute to control tonicity.

The amounts of various compounds for use in the methods of the invention to be administered can be determined by standard procedures. Generally, a therapeutically effective amount is between about 100 mg/kg and $10^{-12}$ mg/kg depending on the age and size of the patient, and the disease or disorder associated with the patient. Generally, it is an amount between about 0.05 and 50 mg/kg, more preferably between about 1.0 and 10 mg/kg for the individual to be treated. The determination of the actual dose is well within the skill of an ordinary physician.

The compounds of the present invention may be administered in combination with one or more farther therapeutic agent for the treatment of IgE-mediated allergic diseases or conditions. Such further therapeutic agents include, without limitation, corticosteroids, β-antagonists, theophylline, leukotriene inhibitors, allergen vaccination, soluble recombinant human soluble IL-4 receptors (Immunogen), anti-IL-4 monoclonal antibodies (Protein Design Labs), and anti-IgE antibodies, such as the recombinant human anti-IgE monoclonal antibody rhuMAb-E25 (Genentech, Inc.) which is currently in advanced clinical trials for the treatment of patients with atopic asthma, and other allergic diseases, such as allergic rhinitis and atopic dermatitis (see, e.g. Barnes, *The New England Journal of Medicine* 341:2006-2008 (1999)). Thus the compounds of the present invention can be used to supplement traditional allergy therapy, such as corticosteroid therapy performed with inhaled or oral corticosteroids.

4. Articles of Manufacture

The invention also provides articles of manufacture comprising the single-chain fusion compounds herein. The article of manufacture comprises a container and a label or package insert on or associated with the container. Suitable containers include, for example, bottles, vials, syringes, etc. The containers may be formed from a variety of materials such as glass or plastic. The container holds a composition which is effective for treating the condition and may have a sterile access port (for example the container may be an intravenous solution bag or a vial having a stopper pierceable by a hypodermic injection needle). The container may also be an inhalation device such as those discussed above. At least one active agent in the composition is a fusion compound of the invention. The label or package insert indicates that the composition is used for treating the condition of choice, such as an allergic condition, e.g., asthma or any of the IgE-mediated allergies discussed above. The article of manufacture may further comprise a further container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

Further details of the invention are illustrated by the following non-limiting Examples.

Example 1

Construction and Expression of a Chimeric Human Fcγ-Fcε Fusion Protein

Materials and Methods

Plasmids, vectors and cells—Plasmid pAG 4447 containing genomic DNA encoding human IgE constant region and expression vector pAN 1872 containing human genomic DNA encoding the hinge-CH2-CH$_3$ portion of IgG$_1$ constant region were obtained from the laboratory of Dr. Morrison. pAN 1872 is derived from the pDisplay vector (Invitrogen). pAG 4447 was developed and used as a cloning intermediate in the construction of a human IgE expression vector disclosed in *J. Biol. Chem.* 271:3428-3436 (1996). To construct the chimeric gene, a pair of primers were designed to amplify the human IgE constant region (CH2-CH3-CH4).

```
5'-end primer:
                                      (SEQ ID NO: 8)
5'GCTCGAGGGTGGAGGCGGTTCAGGCGGAGGTGGCTCTGGCGGTGGCGG
ATCGTTCACCCCGCCCACCGTGAAG3',
containing a flexible linker sequence and an XhoI
site.

3'end primer:
                                      (SEQ ID NO: 9)
5'GGCGGCCGCTCATTTACCGGGATTTACAGACAC3',
``` containing a NotI site.

After amplification, the PCR products were cloned into pCR2.1 vector (Invitrogen). The sequences of the products were confirmed. Then, the ZhoI-NotI fragment was inserted into the 1782 pAN vector, following the IgG$_1$ CH3 domain in the same reading frame by a (Gly$_4$Ser)$_3$ flexible linker. SP2.0 murine myeloma cell line was selected as host for expression because it does not secrete any antibody.

Expression and Purification—The expression vector containing chimeric Fcγ-Fcε gene was linearized at the PvuI site and transfected into SP2/0 cells by electroporation (Bio-Rad). Stable transfectants were selected for growth in medium containing 1 mg/ml geneticin. Clones producing the fusion protein were identified by ELISA using plates coating anti-human IgE (CIA7.12) or IgG (Sigma) antibody. Supernatants from clones were added to wells, and bound protein was detected using goat anti-human IgE or IgG conjugated to alkaline phosphatase (KPL). The fusion protein was purified from the supernatants and ascites by using rProtein A column (Pharmacia).

Western Blotting—The purified protein was run on 7.5% SDS polyacrylamide gel. After transfer, the nylon membrane was blocked by 4% bovine serum albumin/PBS/Tween overnight at 4° C. For protein detection, the blot was probed with either goat anti-human IgE (ε chain specific) or goat anti-human IgG (γ chain-specific) conjugated to alkaline phosphatase (KPL). Color development was performed with an alkaline phosphatase conjugated substrate kit (Bio-Rad).

Binding Test—In order to confirm the binding, FcεRI transfected cells (CHO 3D10) or human HMC-1 cells that express FcγRIIb but not FcεRI were stained with purified fusion protein and then analyzed by flow cytometry. Briefly, cells were collected and washed. The cells were then incubated with 5 μl of 1 mg/ml GE2, PS IgE or human IgG at 4° C. for 60 minutes. After two washes, the cells were stained with FITC conjugated anti-human IgE or IgG at 4° C. for 60 minutes, and visualized by flow cytometry.

Inhibition of Basophil Histamine Release—Acid-stripped Percoll-enriched human blood basophils were primed with 1-10 μg/ml of chimeric human anti-NP IgE at 37° C. in a 5% CO$_2$ incubator and one hour later, challenged with 30 ng of NP-BSA (Kepley, *J. Allergy Clin. Immunol.* 106:337-348 (2000)). Histamine release was measured in the supernatants 30 minutes later. GE2 or control human myeloma IgE was added at various doses and times to test the effects on histamine release.

Passive Cutaneous Anaphylaxis Model—Transgenic mice expressing the human FcεR1α chain and with the murine FcεR1α chain knocked out (provided by Dr. Jean-Pierre Kinet, Harvard Medical School, Boston, Mass., Dombrowicz, et al, *J. Immunol.* 157:1645-1654. (1996)) were primed cutaneously with either recombinant human anti-dansyl or anti-NP IgE. Individual sites were then injected with saline, GE2 or IgE myeloma protein. Four hours later, mice were given a systemic challenge with dansyl-OVA or NP-BSA plus Evans blue, and the resulting area of reaction was measured.

Results

Western blotting showed that the chimeric protein (designated GE2) was expressed as the predicted dimer of approximately 140 kD. The GE2 protein reacted with both anti-human ε and anti-human γ chain-specific antibodies.

GE2 showed the ability to inhibit IgE-mediated release of histamine from fresh human basophils. The results of the dose-dependent inhibition of basophil histamine release using the fusion protein GE2 (±SEM; n+3 separate donors, each in duplicate) are shown in FIG. 8. The data show that, when added to fresh human basophils along with the sensitizing anti-NP IgE antibody, GE2 inhibited subsequent NP-induced release of histamine in a dose-dependent manner, more effectively than an equivalent amount of native human IgE protein. This was time dependent as expected with the greatest effect being observed when the GE2 was added with the sensitizing anti-NP IgE antibody. No effect was observed if the GE2 was given simultaneously with the antigen challenge.

Figure 9:
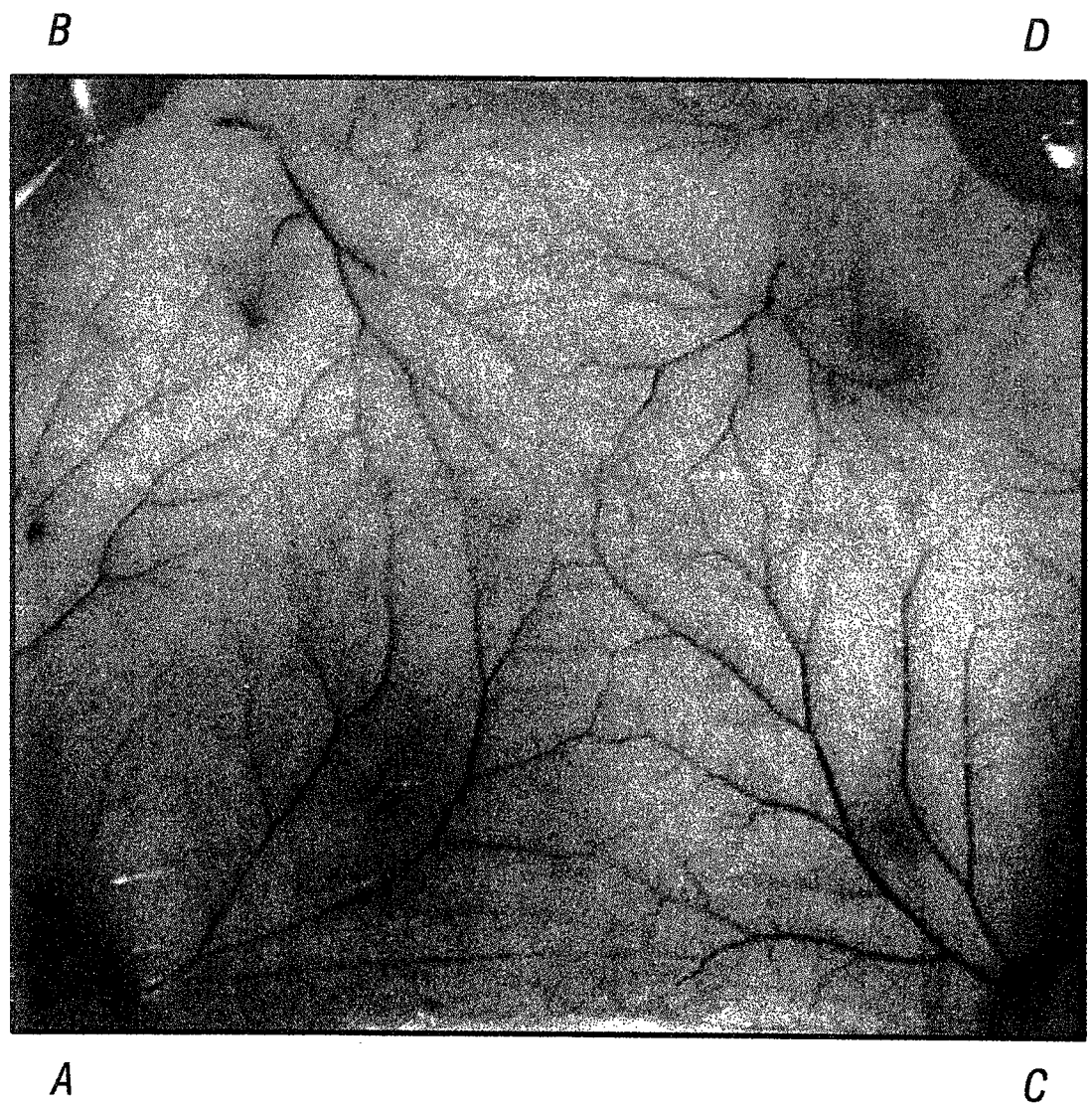
FIG. 9 shows results obtained in the transgenic passive cutaneous anaphylaxis (PCA) model described in the Example. Sites were injected with 250 ng of human anti-IgE NP along with the indicated amounts of PS (non-specific human IgE) or GE2 chimeric fusion protein. Four hours later, the animals were challenged intravenously (IV) with 500 μg of NP-BSA.

To test the in vivo function of GE2, the transgenic passive cutaneous anaphylaxis described above was used. The results are shown in FIG. 9. The size and color of the reaction at the sites of GE2 injection were decreased compared to those injected with comparable amount of human IgE. These results demonstrate that the GE2 protein is able to inhibit mast cell/basophil function greater than an equivalent amount of IgE and implicates binding to both FcεRI and FCγR.

Analysis of binding using flow cytometry showed that the GE2 protein bound in a fashion similar to native IgE to the human FcγRII expressed on HMC-1 cells. The data are shown in FIG. 10. Similar results were obtained for the FcεRI on 3D 10 cells, as shown in FIG. 11.

Example 2

Construction and Expression of Chimeric Human Fcγ-autoantigen Fusion Proteins for Use in Treating Subjects with Multiple Sclerosis Two human $F_c\gamma$-autoantigen fusion polypeptides are produced using recombinant DNA techniques and a mammalian protein overexpression system. The resulting recombinant fusion proteins are purified using immunoprecipitation techniques and analyzed, as described below. Two forms of the fusion polypeptide are described. Both forms of the fusion polypeptide contain the hinge-CH2-CH3 portion of the $IgG_1$ constant region, as provided in SEQ ID NO:1. One form of the fusion polypeptide comprises a full length myelin-basic-protein (MBP) amino acid sequence (as provided in SEQ ID NO:12), while an alternative version of the fusion polypeptide comprises a portion of MBP containing essentially the minimal, immunodominant autoimmune epitope, i.e., $MBP_{83-99}$. (Warren et al., *Proc. Natl. Acad. Sci. USA* 92:11061-11065 [1995] and Wucherpfennig et al., *J. Clin. Invest.*, 100(5):1114-1122 [1997]). This minimal MBP epitope has the amino acid sequence:

$E_{83}$NPVVHFFKNIVTPRTP$_{99}$ (SEQ ID NO: 13)

The resulting fusion polypeptides find use in the treatment of autoimmune multiple sclerosis, as well as for the prevention of anaphylactic response which may result from exposure to exogenous MBP polypeptide, as would be encountered during tolerance therapy.

Vectors—Mammalian expression vectors encoding the fusion polypeptides are constructed by subcloning the IgG and MBP autoantigen sequences into a suitable vector. In this Example, a modified form of the pDisplay vector (Invitrogen) is used as the backbone, called pAN1872, which uses the constitutively active $P_{CMV}$ promoter to transcribe subcloned sequences, and produces these sequences with an in-frame hemagglutinin (HA) epitope tag. The modified vector encodes a secreted form of the subcloned sequences. The pAN1872 vector contains human genomic DNA encoding the hinge-CH2-CH3 portion of $IgG_1$ constant region, as described in Example 1 and SEQ ID NO:1.

To construct the chimeric IgG-autoantigen expression vector, myelin-basic-protein (MBP) sequences are amplified from an MBP cDNA vector using PCR protocols. Any vector containing MBP cDNA sequence can be a suitable template for the PCR reaction. The PCR primers are designed to permit the amplification of the full length MBP cDNA, or alternatively, any suitable portion of the MBP cDNA. The PCR primers used are not limited to a particular nucleotide sequence, as various primers can be used dependent on variations in the template backbone and the desired MBP portion(s) for amplification.

The resulting double stranded PCR products are then subcloned into the pAN1872 vector, in such a way that the coding sequences of IgG heavy chain constant region and the MBP sequences are in frame to produce a single translation product. The suitable PCR primers can also be designed to incorporate a flexible linker sequence (e.g., [Gly$_4$Ser]$_3$) and terminal endonuclease restriction sites to facilitate the in-frame subcloning, and are further designed to permit the subcloning of the MBP sequences at the carboxy-terminus (C-terminus) of the IgG heavy chain constant region.

A portion of MBP as small as the $MBP_{83-99}$ immunodominant epitope also finds use with the present invention. In this case, a suitable double-stranded oligonucleotide can be generated using synthetic means for use in the subcloning step. The nucleotide sequence of the engineered fusion construct coding sequences is confirmed by DNA sequencing.

Expression and Purification—Following construction of the mammalian expression vectors above, these vectors are linearized by single-site cleavage with a suitable restriction enzyme (e.g., PvuI). These linearized nucleic acids are then transfected in the SP2.0 cell line (a murine myeloma) using an electroporation apparatus and reagents (Bio-Rad). The SP2.0 cell line is used, as it does not secrete antibody, and will not contaminate the purified antibody encoded by the transfected expression vector.

Following the electroporation, stable transfectants are selected in Iscove's modified Dulbecco's growth medium supplemented with 1 mg/ml geneticin. Supernatants from surviving clones are collected and analyzed for fusion molecule production by ELISA, using plates coated with rabbit anti-IgG antibody (Sigma). The fusion molecules are then specifically detected using a goat anti-human IgG conjugated to alkaline phosphatase (KPL) detection antibody. SP2.0 clones producing the fusion molecule are thus identified.

Purification—The fusion polypeptide contained in the SP2.0 cell culture supernatants is purified using rProtein A column purification (Pharmacia). Alternatively, as a source of starting material for the purification, the SP2.0 cell lines is used to produce ascites fluid in nude mice. The ascites fluid is collected and purified using rProtein A column purification. Alternatively still, the fusion polypeptide is purified from cell culture supernatants or ascites fluids using an anti-HA immunoaffinity purification, as the fusion polypeptides are translated with an in-frame hemagglutinin tag encoded by the pDisplay vector. Such purification methods are well known in the art.

Western Blotting—The fusion polypeptide is analyzed by Western immunoblotting analysis. The purified polypeptide material is run on a 7.5% SDS polyacrylamide gel. Following transfer to nylon membrane, the blot is blocked using 4% bovine serum albumin/PBS/Tween overnight at 4° C. For protein detection, the blot is probed with goat anti-human IgG (γ chain-specific) conjugated to alkaline phosphatase (KPL). Color development is performed with an alkaline phosphatase-conjugated substrate kit (Bio-Rad). Alternatively, anti-HA antibodies can be used as the primary detection antibody in the Western blot.

Binding Test—In order to confirm the binding of the fusion polypeptide to Fcγ receptors, human HMC-1 cells that express FcγRIIb are contacted with purified fusion protein and then analyzed by flow cytometry. Briefly, cells are collected, washed, then incubated with 5 μl of 1 mg/ml fusion polypeptide, or alternatively, with human IgG at 4° C. for 60 minutes. After two washes, the cells are stained with FITC-conjugated anti-human IgG at 4° C. for 60 minutes, and visualized by flow cytometry.

Inhibition of Basophil Histamine Release—The ability of the fusion polypeptide to suppress histamine release is assessed using a histamine release assay. Acid-stripped Percoll-enriched human blood basophils are primed with 1-10 μg/ml of chimeric human-anti-NP IgE at 37° C. in a 5% $CO_2$ incubator and one hour later, and challenged with 30 ng of NP-BSA (Kepley, *J. Allergy Clin. Immunol.* 106:337-348 (2000)). Histamine release is measured in the supernatants 30 minutes later. Fusion polypeptide or control human myeloma IgE are added at various doses and times to test the effects on histamine release.

Passive Cutaneous Anaphylaxis Model—The ability of the fusion polypeptide to suppress anaphylaxis is assessed using a mouse model assay. Transgenic mice expressing the human FcεR1α chain and with the murine FCεR1α chain knocked out (provided by Dr. Jean-Pierre Kinet, Harvard Medical School, Boston, Mass., Dombrowicz, et al, *J. Immunol.* 157: 1645-1654. (1996)) are primed cutaneously with either recombinant human anti-dansyl or anti-NP IgE. Individual sites are then injected with saline, fusion polypeptide or IgE myeloma protein. Four hours later, mice are given a systemic challenge with dansyl-OVA or NP-BSA plus Evans blue, and the resulting area of reaction is measured.

All references cited throughout the specification are hereby expressly incorporated by reference. It is understood that the application of the teachings of the present invention to a specific problem or situation will be within the capabilities of one having ordinary skill in the art in light of the teachings contained herein. Examples of the products of the present invention and representative processes for their production and use should not be construed to limit the invention.

What is claimed is:

1. A method for inhibiting symptoms resulting from a type I hypersensitivity reaction in a subject, comprising administering at least one fusion molecule to said subject, wherein said fusion molecule comprises a first polypeptide sequence consisting of a native human IgG immunoglobulin heavy chain constant region of SEQ ID NO: 2 or SEQ ID NO: 3, and is covalently linked via a polypeptide linker to a second polypeptide sequence capable of binding indirectly to a native IgE receptor (FcεR), wherein said second polypeptide is an allergen, wherein said type I hypersensitivity reaction comprises a type I hypersensitivity reaction to said allergen, and wherein said symptoms are inhibited.

2. The method of claim 1, wherein said symptoms resulting from a type I hypersensitivity reaction are due to an anaphylactic response.

3. The method of claim 1, wherein said subject receives immunotherapy for a type I hypersensitivity-mediated disease.

4. The method of claim 3, wherein said fusion molecule is administered to said subject prior to said subject receiving immunotherapy.

5. The method of claim 3, wherein said fusion molecule is co-administered to said subject with said immunotherapy.

6. The method of claim 3, wherein said fusion molecule is administered after said subject receives immunotherapy.

7. A method for inhibiting IgE release or the symptoms resulting from a type I hypersensitivity disease in a subject, comprising administering at least one fusion molecule to said subject, wherein said fusion molecule comprises a first polypeptide and a second polypeptide, wherein said first polypeptide consists of a native human IgG heavy chain constant region sequence, wherein said native human IgG heavy chain constant region sequence is the native human IgG heavy chain constant region of SEQ ID NO: 2 or SEQ ID NO: 3, and wherein said first polypeptide is directly functionally connected to the N-terminus of a said second polypeptide, wherein the second polypeptide is an allergen, wherein said fusion molecule is not capable of T cell interaction prior to internalization, wherein said type I hypersensitivity reaction comprises a type I hypersensitivity reaction to said allergen, and wherein said IgE release or symptoms are inhibited.

8. The method of claim 1, wherein said portion of a native human IgG immunoglobulin heavy chain constant region is the native human IgG heavy chain constant region of SEQ ID NO: 2 or SEQ ID NO: 3, and is directly functionally connected to the N-terminus of said second polypeptide sequence.

9. The method of claim 1, wherein said fusion molecule is capable of cross-linking a native IgG inhibitory receptor with a native IgE receptor.

10. The method of claim 7, wherein said fusion molecule is capable of cross-linking a native human IgG inhibitory receptor with a native IgE receptor (FcεR).

11. The method of claim 8, wherein said fusion molecule is capable of cross-linking a native human IgG inhibitory receptor with a native IgE receptor (FcεR).

12. The method of claim 1, wherein said polypeptide linker consists of about 5 amino acids to 25 amino acid residues.

* * * * *